(12) United States Patent
Li et al.

(10) Patent No.: US 9,150,453 B1
(45) Date of Patent: Oct. 6, 2015

(54) ANTIMICROBIAL EXFOLIATED VERMICULITE COMPOSITE MATERIAL AND METHODS FOR PREPARING THE SAME

(76) Inventors: Bowen Li, Chassell, MI (US); Jiann-Yang Hwang, Chassell, MI (US)

( * ) Notice: Subject to any disclaimer, the term of this patent is extended or adjusted under 35 U.S.C. 154(b) by 954 days.

(21) Appl. No.: 12/928,101

(22) Filed: Dec. 3, 2010

Related U.S. Application Data

(60) Provisional application No. 61/266,372, filed on Dec. 3, 2009.

(51) Int. Cl.
| | | |
|---|---|---|
| C04B 20/06 | (2006.01) | |
| C04B 20/04 | (2006.01) | |
| A01N 59/16 | (2006.01) | |

(52) U.S. Cl.
CPC ............. *C04B 20/06* (2013.01); *A01N 59/16* (2013.01)

(58) Field of Classification Search
CPC .................................. C04B 20/06; A01N 59/16
See application file for complete search history.

(56) References Cited

U.S. PATENT DOCUMENTS

| | | | |
|---|---|---|---|
| 4,210,530 A * | 7/1980 | Etzel et al. .................... | 210/668 |
| 4,497,869 A | 2/1985 | Kamigaito et al. | |
| 5,009,898 A | 4/1991 | Sakuma et al. | |
| 5,298,253 A | 3/1994 | LeFiles et al. | |
| 5,441,717 A | 8/1995 | Ohsumi et al. | |
| 5,503,840 A | 4/1996 | Jacobson et al. | |
| 6,143,318 A | 11/2000 | Gilchrist et al. | |

OTHER PUBLICATIONS

Bowen, PhD dissertation: Characteristics and antimicrobial activity of copper-based materials, 2008, 86 pages.*
Stylianou et al., Desalination, 2007, 215, 133-142.*
Journal: Journal of Minerals & Materials Characterization & Engineering, vol. 1, No. 1, pp. 61-68, 2002, U.S.A.

* cited by examiner

*Primary Examiner* — Kyle Purdy

(57) ABSTRACT

An antimicrobial exfoliated vermiculite composite material is synthesized by impregnating the interlayers of exfoliated vermiculite through cation exchange and surface absorption with at least one of the following metal species: copper, silver, zinc, and manganese. Alternately, the antimicrobial material is synthesized by impregnating interlayers of unexfoliated vermiculite with said metal species and exfoliating the product thereafter. The metal species can be in ionic state, nanometer particles, and in the form of metal oxides, metal hydroxides, metal nitrides, metal carbides, metal phosphates, metal silicates, metal borides, metal sulfides, metal halides, metal hydrides, metal nitrates, metal carbonates, and metal sulfadiazines. Any mixture of these metal species in the exfoliated vermiculite can provide protection against a broad spectrum of pathogens. This antimicrobial material in any desired form, in whole or as an additive, can effectively self-decontaminate various materials or products as the antimicrobial metal ions slowly diffuse to the surface of the products.

15 Claims, 46 Drawing Sheets

Fig. 12 (1)
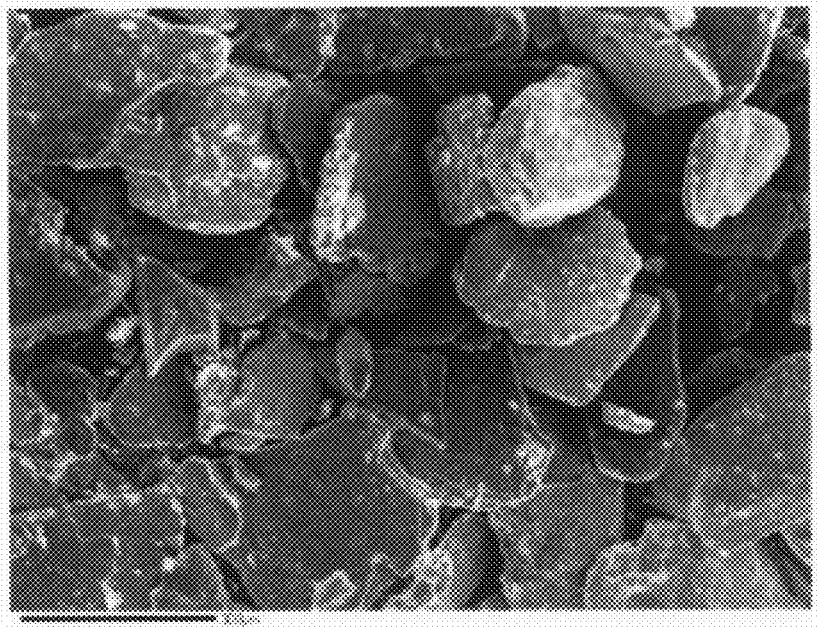
Fig. 12 (2)

Fig. 12 (3)

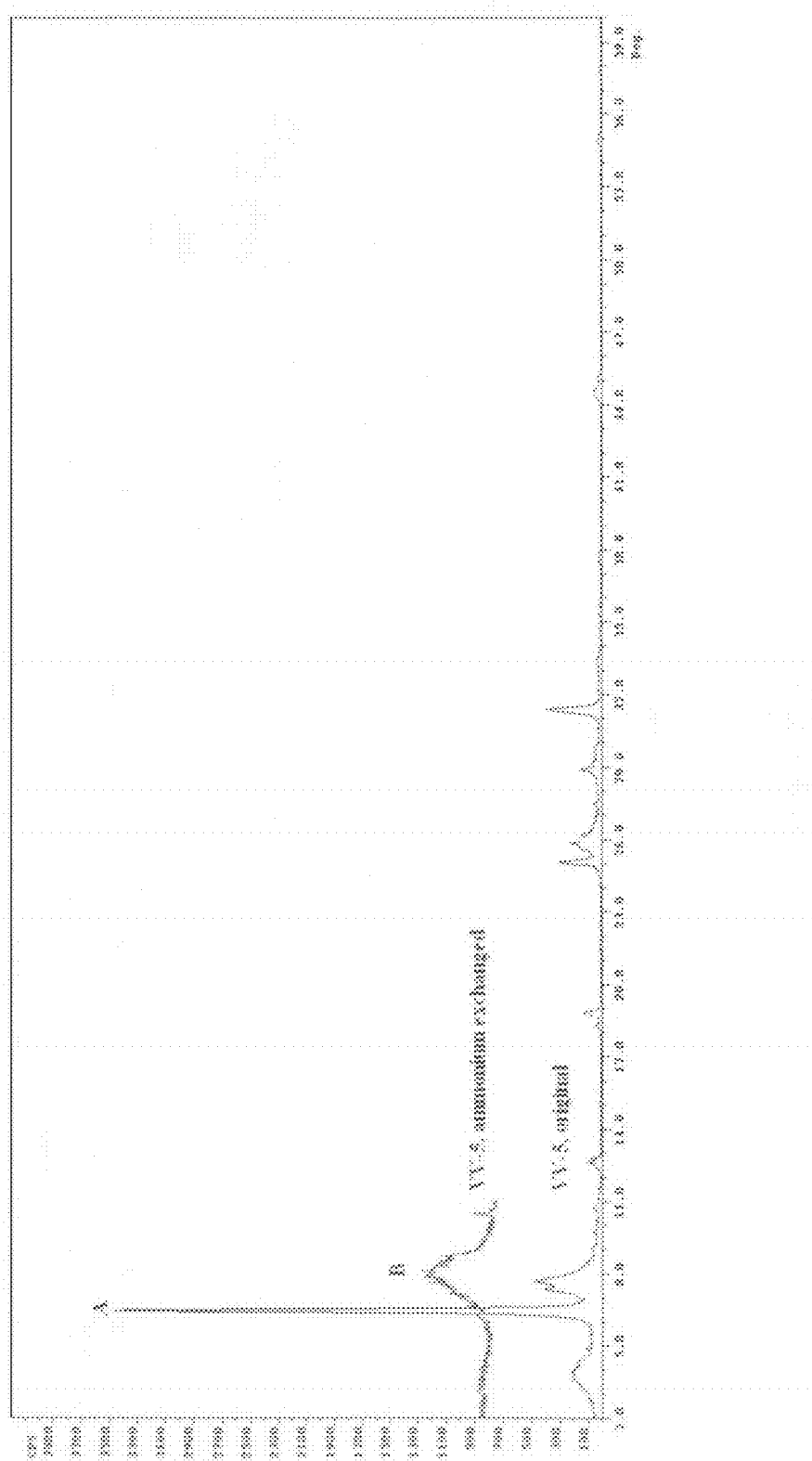

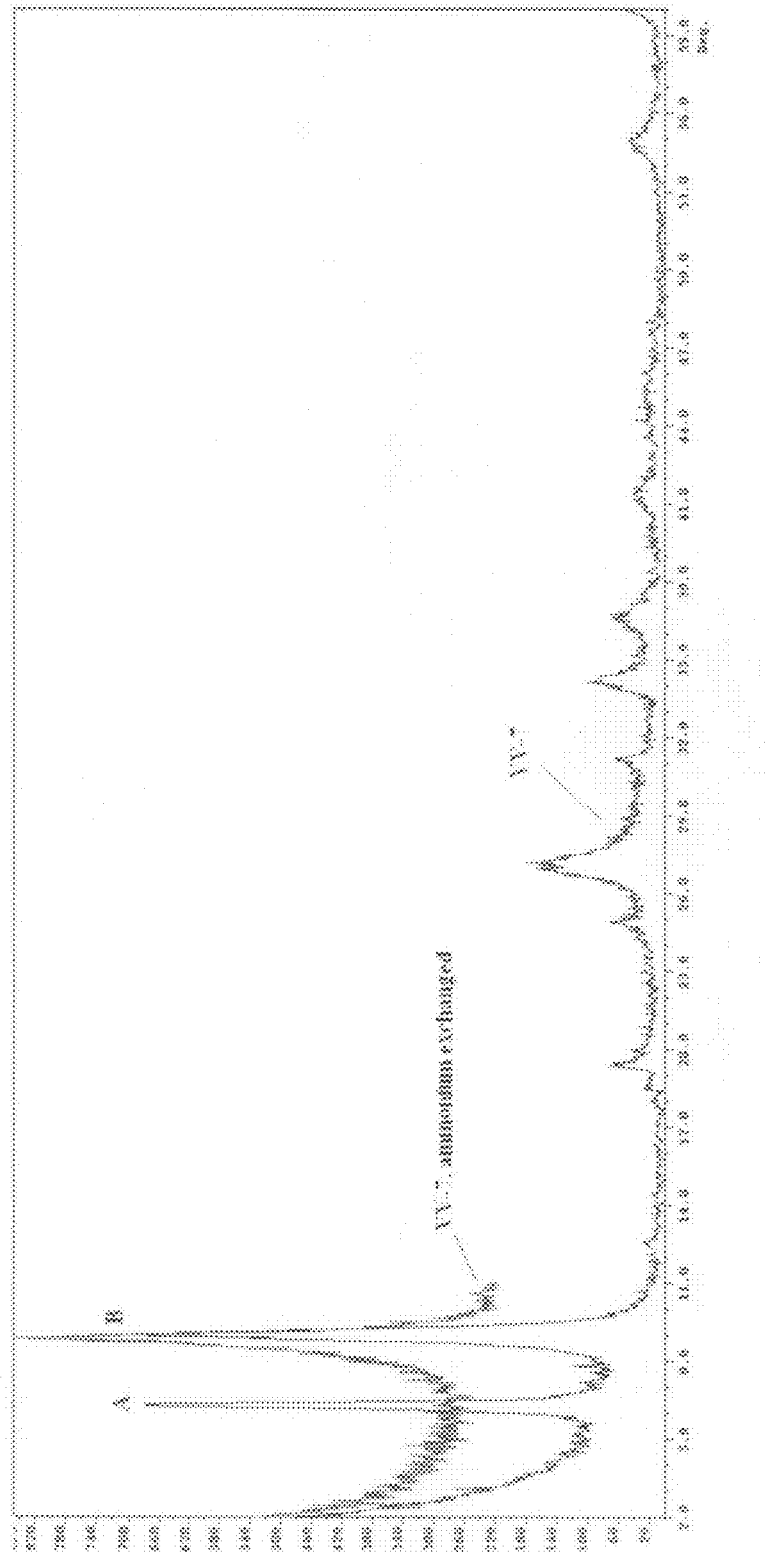

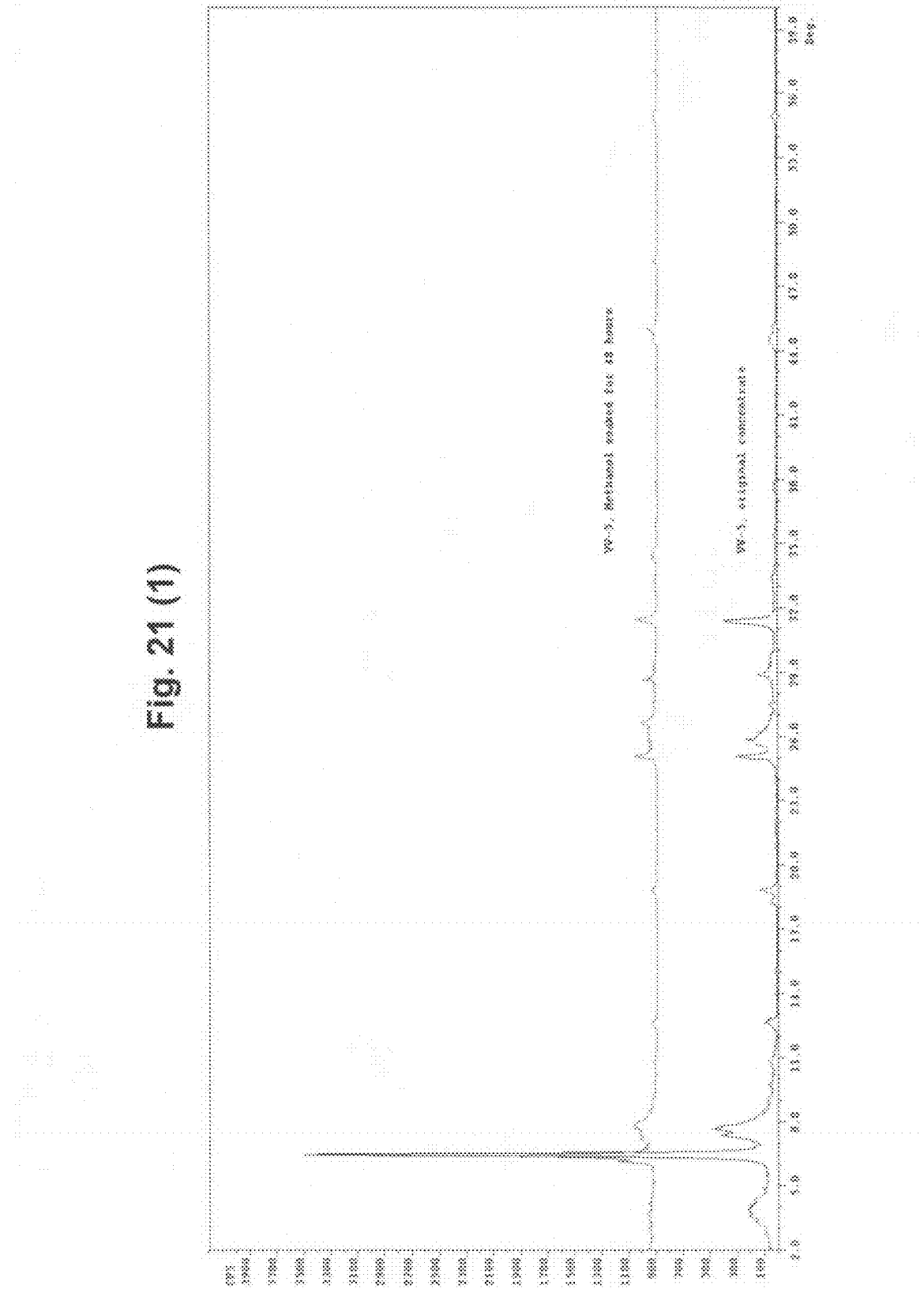

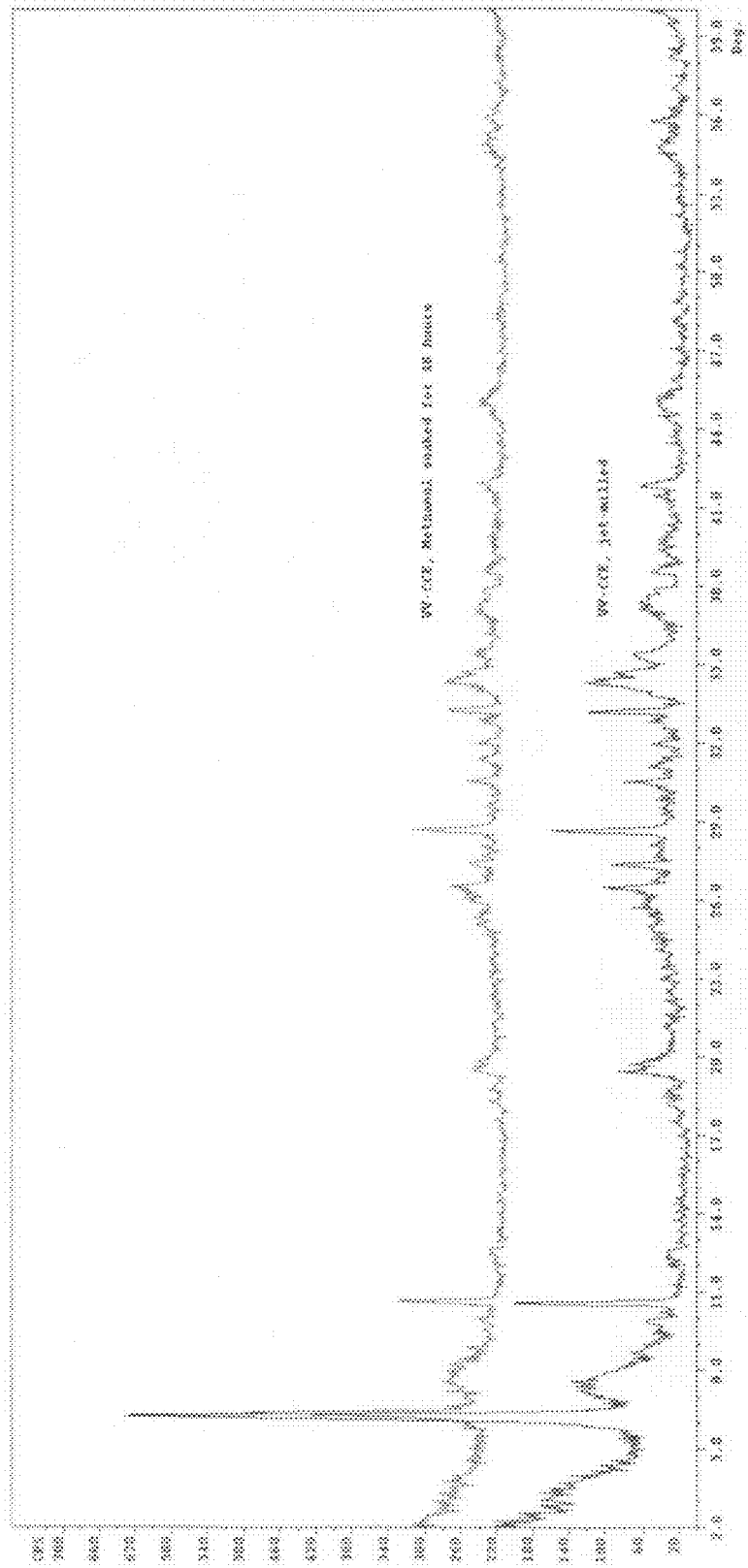
Fig. 21 (2)

Fig. 22 (1)
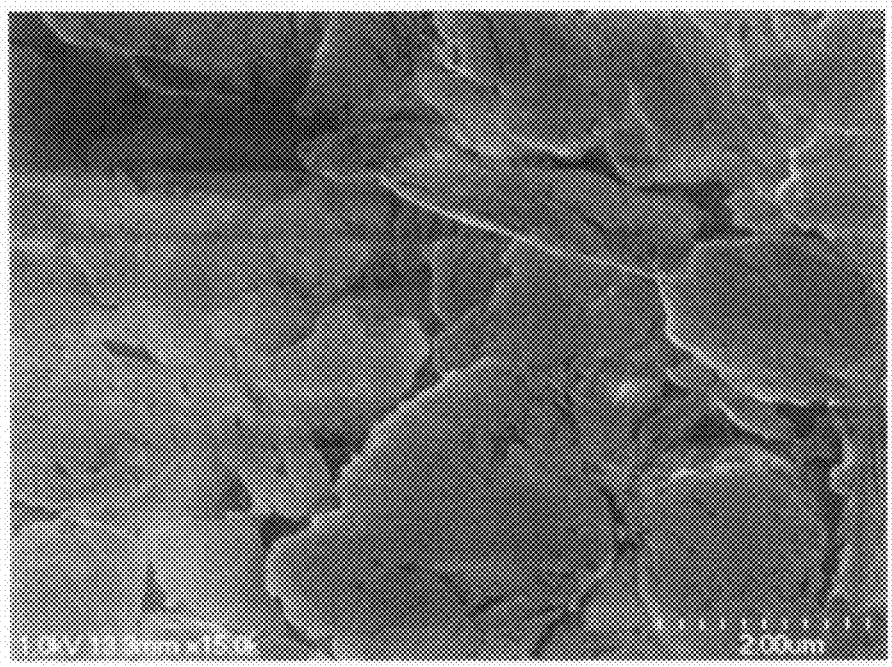
Fig. 22 (2)
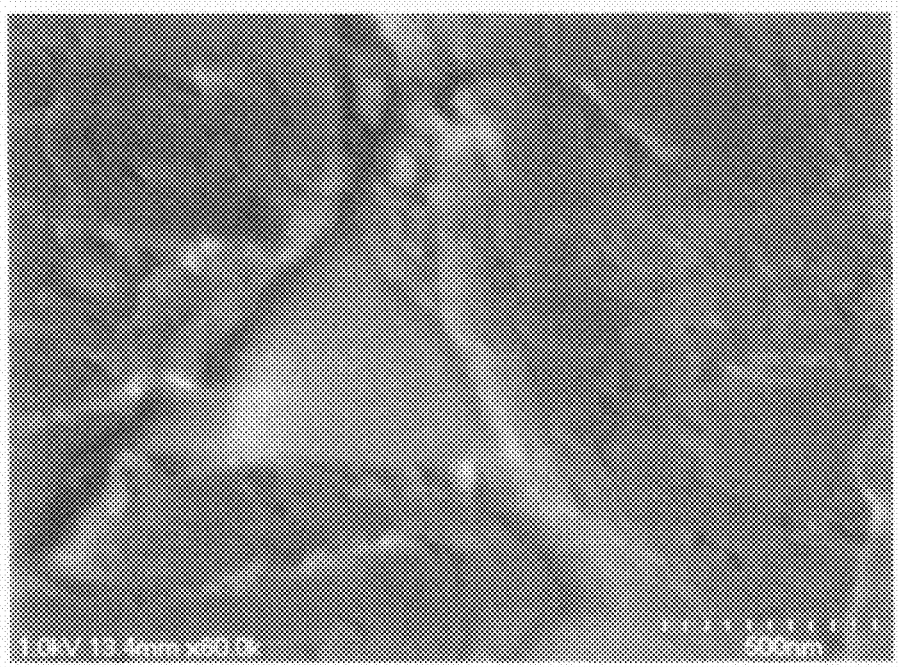

Fig. 23 (1)
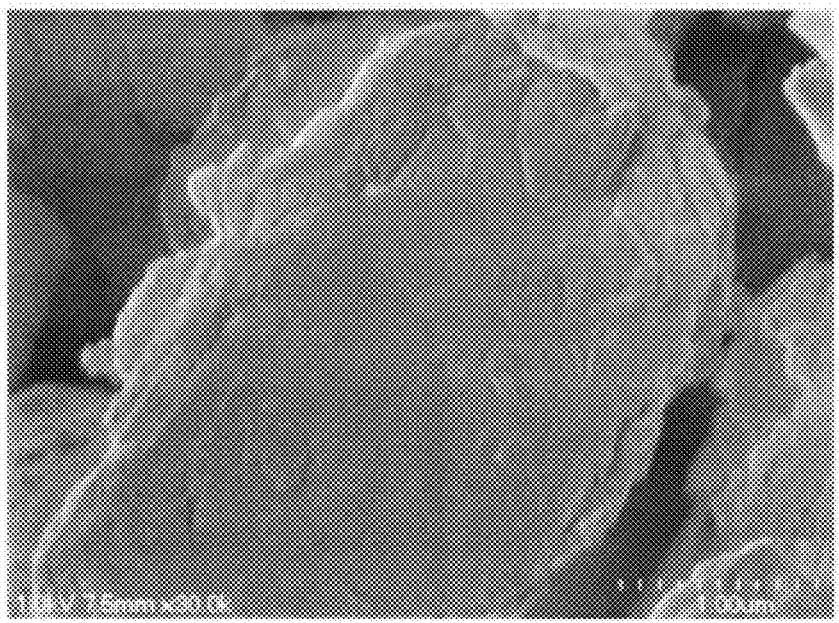
Fig. 23 (2)
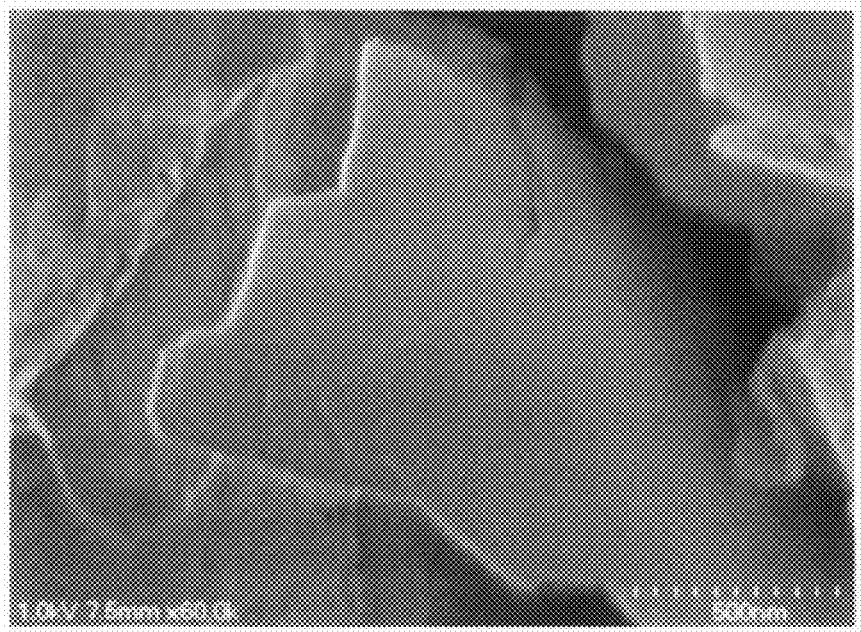

Fig. 24 (1)
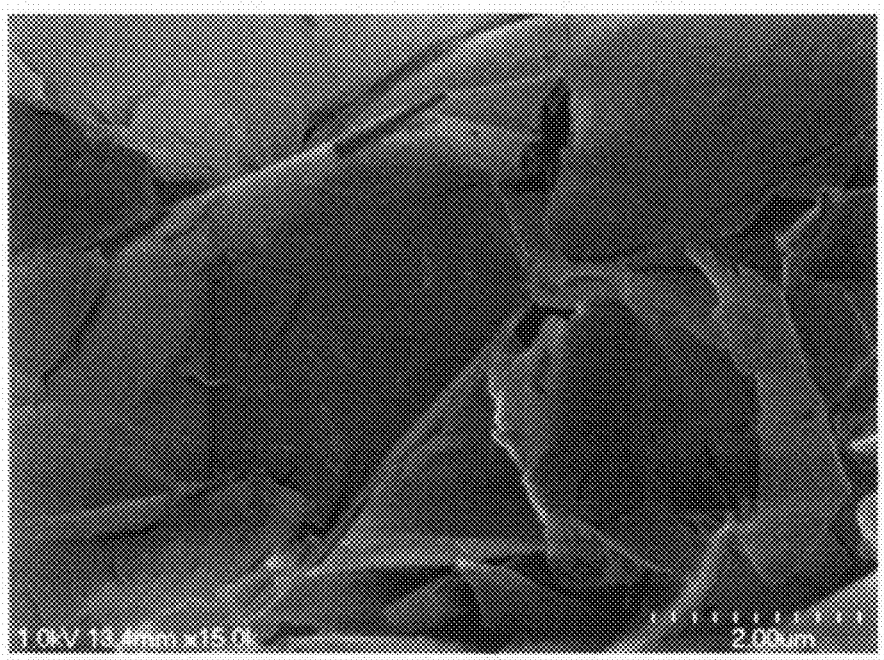
Fig. 24 (2)

Fig. 25 (1)
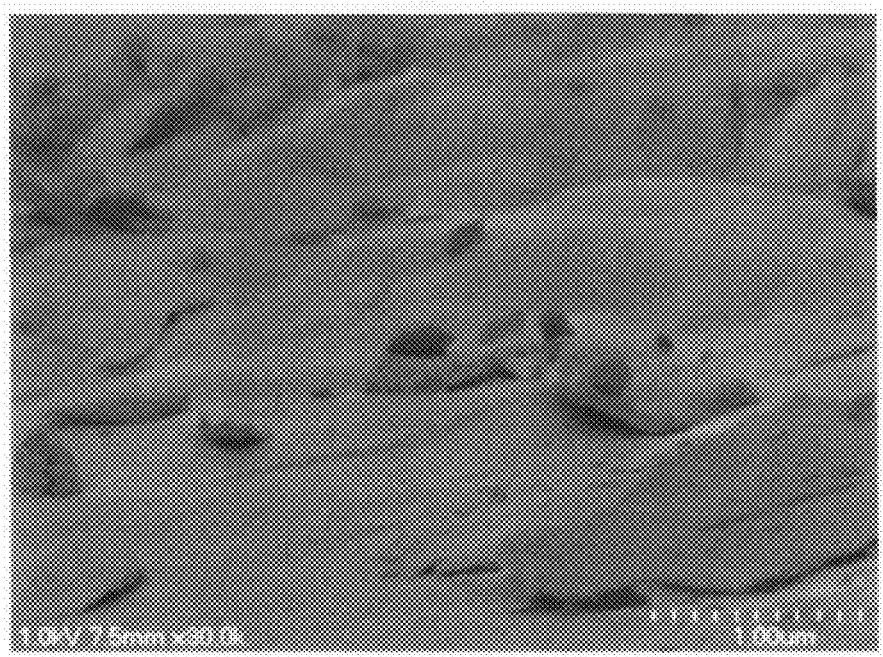
Fig. 25 (2)
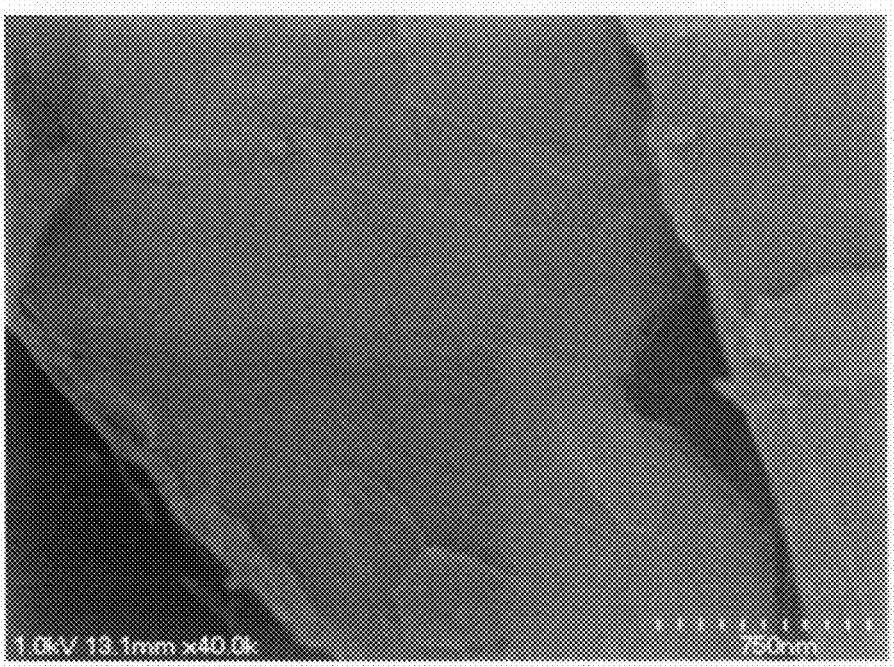

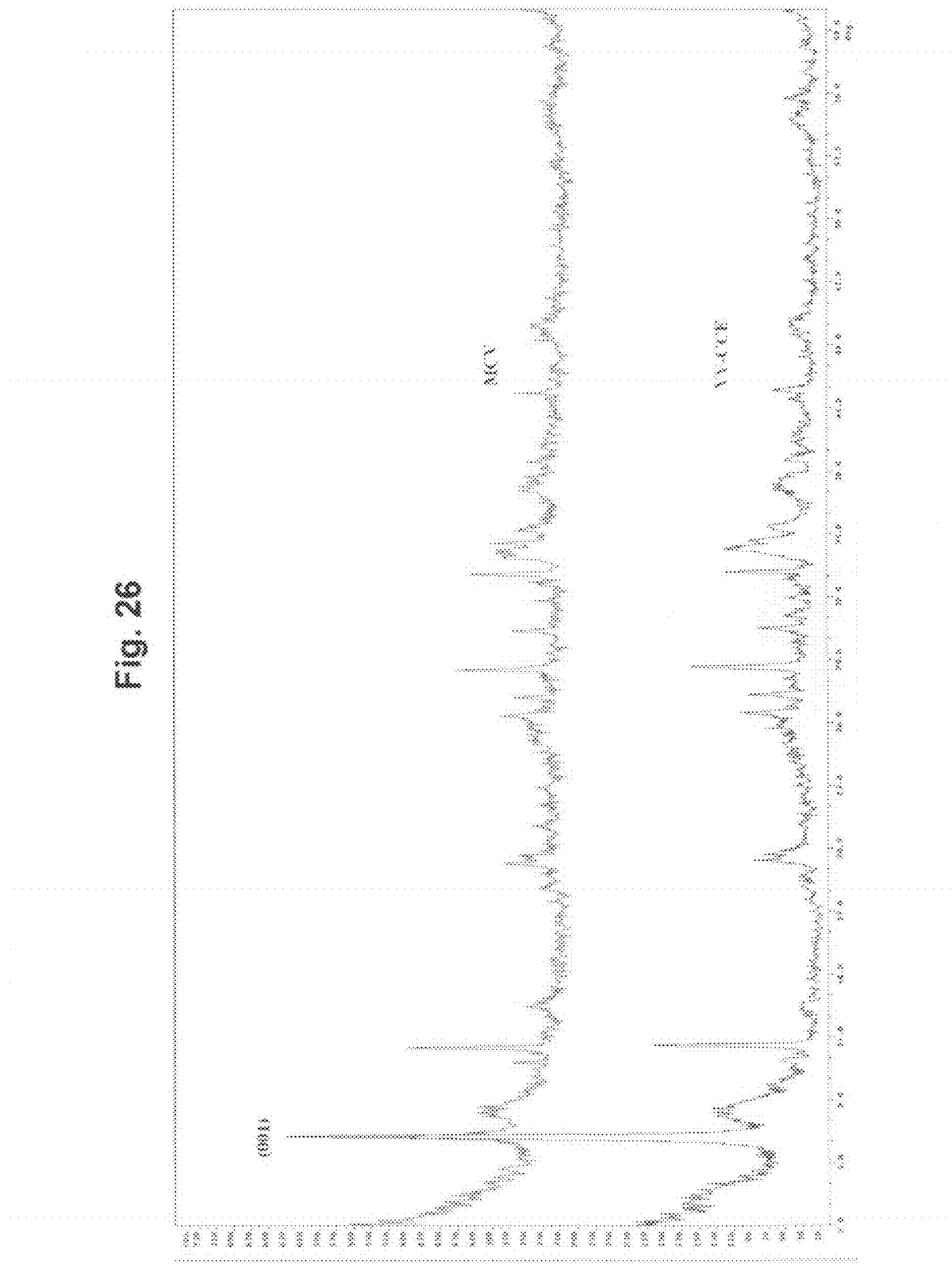

Fig. 43 (1)
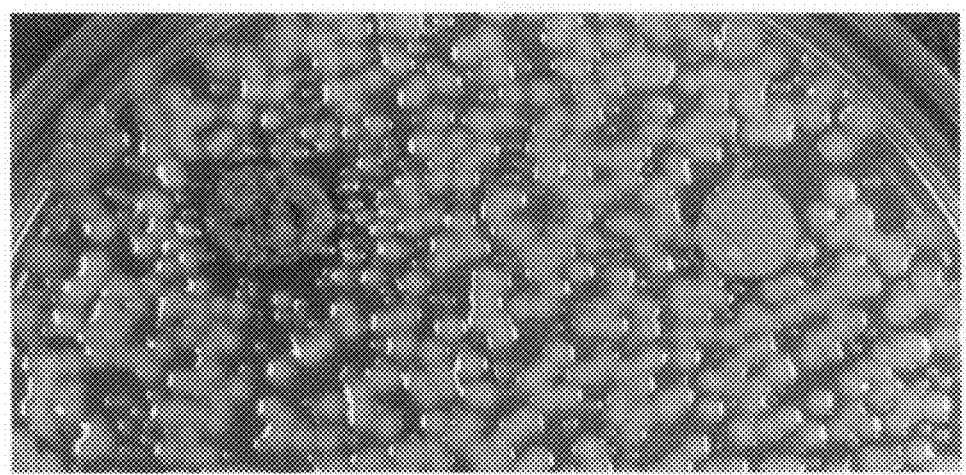
Fig. 43 (2)
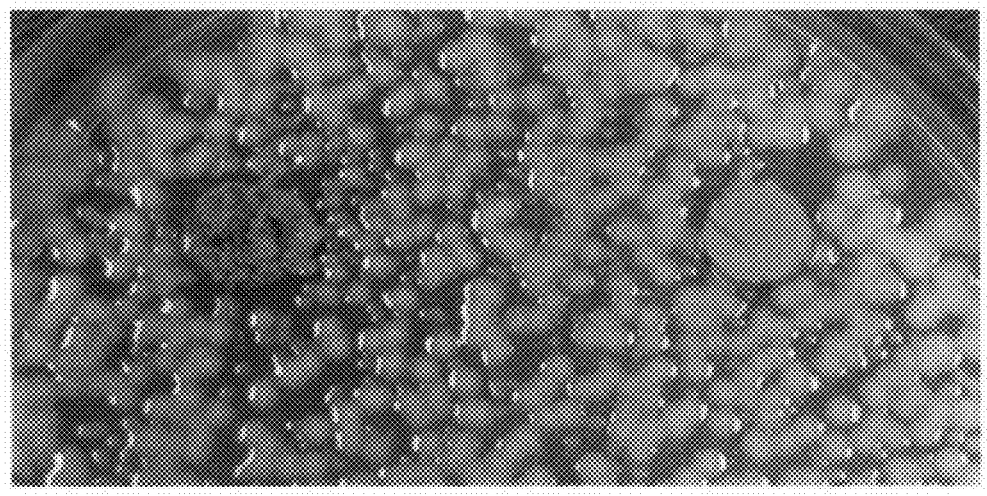

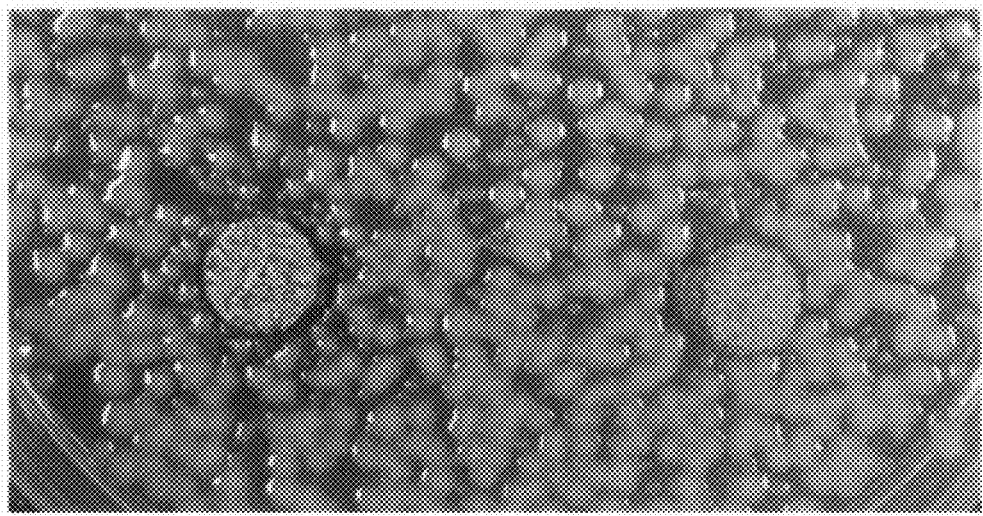
Fig. 44 (1)
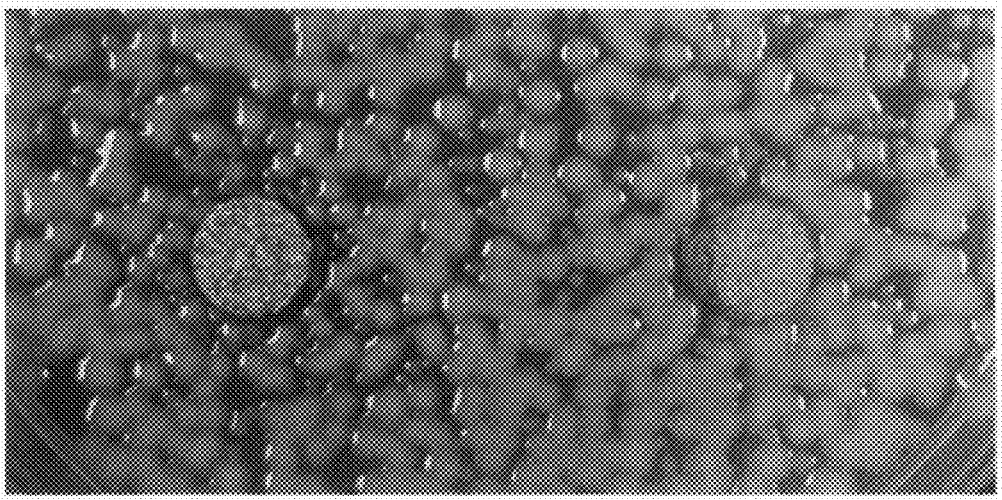
Fig. 44 (2)

Fig. 50 (1)
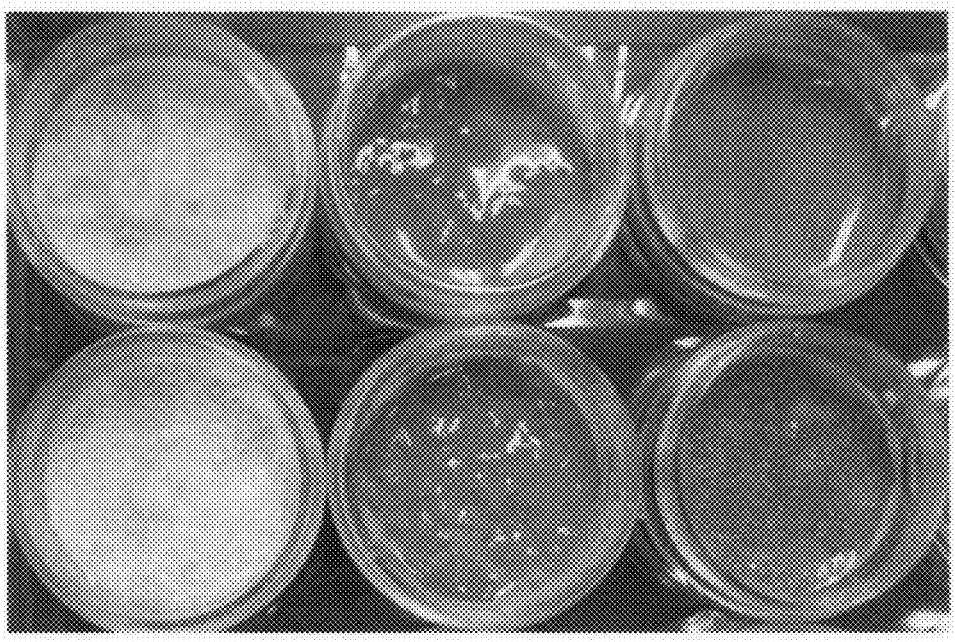
Fig. 50 (2)
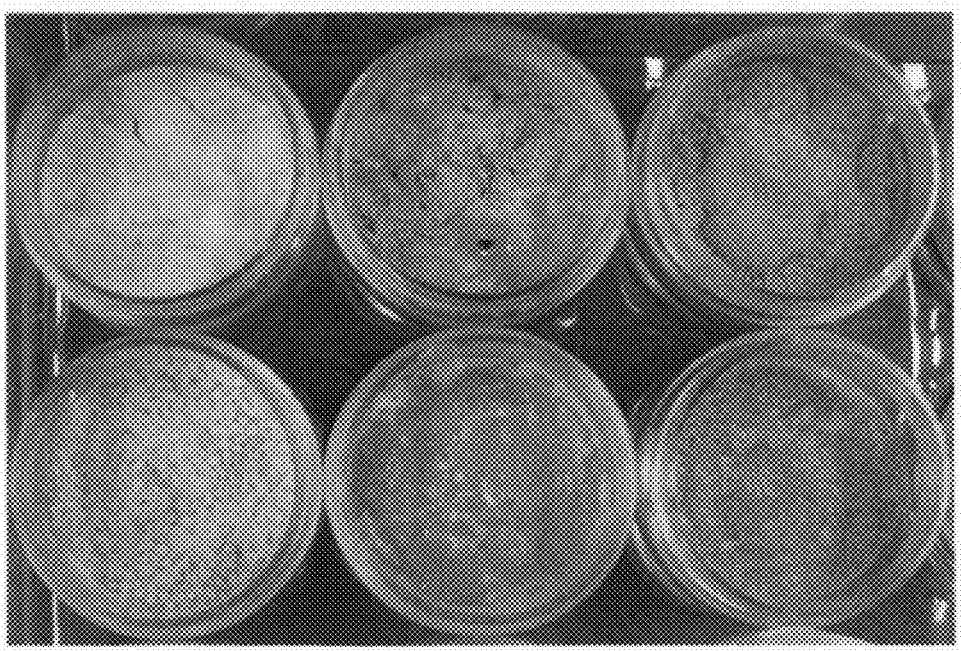

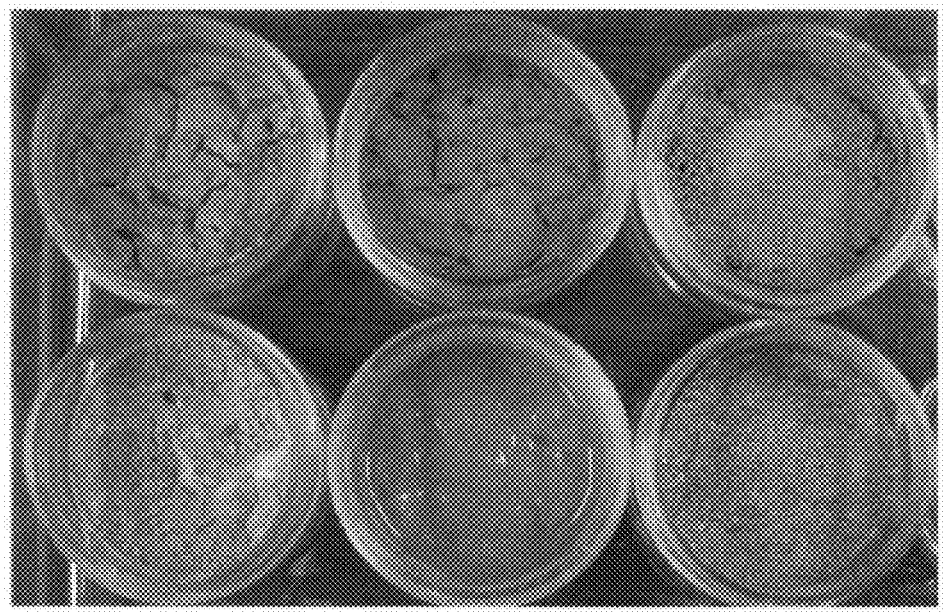
Fig. 50 (3)

ANTIMICROBIAL EXFOLIATED VERMICULITE COMPOSITE MATERIAL AND METHODS FOR PREPARING THE SAME

CROSS-REFERENCE TO RELATED APPLICATIONS

This application claims the benefit of PPA Serial No. 61/266,372, filed Dec. 3, 2009 by the present inventors.

BACKGROUND OF THE INVENTION

1. Field of Invention

The present invention relates to an antimicrobial composite material and a method for producing the same. More particularly, the present invention relates to a single or multiple metal vermiculite composite material having antibacterial/antifungal activities, and to the method of making and using the same.

2. Discussion of Prior Art

Vermiculite is a naturally occurring layer-structured mineral, which is in the size of 0.1 mm to several centimeters, and composed of alternative aluminum silicate sheets and hydrate cation sheets. The cations in the interlayer region are exchangeable and can be easily replaced in the laboratory by cation exchange reaction. Within the interlayer regions of vermiculite, water molecules will transform into steam when rapidly heated to high temperature (around 850° C. or higher), causing the dramatic increase of volume of vermiculite particles (expansion, usually called exfoliation). Exfoliated vermiculite has very unique properties, such as high porosity, high specific surface area, high aspect ratio of laminates, low density, and high cation exchange capacity. Typically, the cation exchange capacity of vermiculite reach 50-150 mmol/100 g.

Vermiculite is extensively distributed in the United States and worldwide. Annually, over 100 thousand tons of vermiculite was produced, and over 150 thousand tons of vermiculite was consumed in the United States. Vermiculite has been extensively used in various industrial products and applications. Most vermiculite is consumed in thermally exfoliated form. These applications include agricultural growth media, lightweight aggregates, building boards, insulations, additives in coatings, plastics, fertilizers, papers, and wood products, etc. However, there is no report on the making of antimicrobial exfoliated vermiculite.

Currently, there have been some reports on making antimicrobial additive with clay minerals, such as montmorillonite, bentonite, kaolinite. Clay minerals have similar silicate sheets and cation exchange property with vermiculite. However, vermiculite is significantly distinguished itself from clay minerals by its natures, such as unique interlayer cations, high layer charge that results in a high cation exchange capacity, unique exfoliation function, and a larger particle size. Further, exfoliated vermiculite has unique properties, such as lightweight, high porosity, and high surface absorption.

It has been found that some transition metals, such as silver, copper, zinc, nickel, and manganese, exhibit antimicrobial activities. Numerous attempts have been made to utilize this property to various applications. For example, U.S. Pat. No. 5,009,898 describes antimicrobial hydroxyapatite powders containing hydroxyapatite powder and metal ions selected from silver, copper and zinc ions.

U.S. Pat. No. 5,441,717 describes process for producing antimicrobial compounds by forming metal salts of silver, copper, zinc, tin, mercury, lead, iron, cobalt, nickel, manganese, arsenic, antimony, bismuth, barium, cadmium and chromium.

U.S. Pat. No. 5,503,840 exposures an antimicrobial composition containing titanium dioxide, barium sulfate, zinc oxide particles, and mixtures thereof having successive coatings of silver, in some cases a coating of zinc and/or copper compounds such as zinc oxide, copper (II) oxide and zinc silicate; silicon dioxide; alumina. This composition made up of polymer, which also is the host of metals.

U.S. Pat. No. 6,143,318 describes an antimicrobial composition containing copper, silver, magnesium, zinc, cerium, manganese bismuth, selenium and boron. In this composition, antimicrobial metals were held by glass.

U.S. Pat. No. 5,298,253, disclosed a granular copper hydroxide dry flowable bactericide/fungicide. In this process, copper hydroxide was admixed with bontonite, and dried granules were formed by spray drying method.

U.S. Pat. No. 4,497,869 describes formed product of vermiculite (bulk density of from 0.9 to 2.5 (g/cm.sup.3)) containing metal salts by mixing process, to improve the water resistance and strength of products.

U.S. Pat. No. 4,210,530 describes the treatment of metal plating wastes with an unexpanded vermiculite cation exchange column, which employs unexfoliated vermiculite as an absorption to filter heavy metals such as copper.

Summarily, there is no report on preparation and application of exfoliated vermiculite antimicrobial compound. In addition, only ionic metals and their nanoparticles perform antimicrobial activity. These metallic ions also need an effective carrier for their loading, desirable release rate, chemical stability, and durability for their appropriate uses. How to hold and release the ionic metals appropriately is a significant issue to the development and applications of metal ion-typed antimicrobial materials. Vermiculite can provide a consistent and effective delivery vehicle for antimicrobial agents. Metal ions in the interlayer of vermiculite can be slowly released via cation exchange and delivered to the surface of particles by diffusion.

OBJECTS AND ADVANTAGES

Accordingly, it is an object of this invention to provide a safe, wide-spectrum, efficient, very durable, inexpensive single-metal or multi-metal antimicrobial compound that can be used as an additive for self-decontamination of various materials and products.

SUMMARY OF THE INVENTION

Briefly, the present invention provides a novel antimicrobial exfoliated vermiculite compound comprising exfoliated vermiculite and metal ions having antimicrobial properties.

The antimicrobial exfoliated vermiculite compound is prepared by implanting antimicrobial metallic ions into the structure of exfoliated vermiculite through cation exchange reaction and surface absorption.

This antimicrobial exfoliated vermiculite compound can be in powder form, applicable as an additive to mix in diverse products, such as plastics, paints, wood products, papers, leather, textiles, concretes, etc. This exfoliated vermiculite antimicrobial additive slowly releases antimicrobial cations, thus providing the products with antimicrobial properties.

DRAWINGS

FIG. 1—Sketch of unexfoliated copper vermiculite (left) and exfoliated copper vermiculite (right). Lines represent aluminum silicate sheets and dots represent copper cations.

FIG. 2—Scanning Electron Microscopy (SEM) images of laminates of unexfoliated vermiculite (left) and a grain of exfoliated vermiculite (right).

FIG. 3—Bactericide activity of unexfoliated copper vermiculite [incubated time (hrs.) vs viable bacteria ($\log_{10}$CFU/ml)].

FIG. 4—Bactericide activity of exfoliated copper vermiculite [incubated time (hrs.) vs survivors ($\log_{10}$CFU/ml)].

FIG. 5—Differential thermal analysis of unexfoliated vermiculite.

FIG. 6—Differential thermal analysis of exfoliated vermiculite.

FIG. 7—shows the general spread approaches of infectious bacteria from infectious sources to potential hosts.

FIG. 8—shows the major determination methods for removing microbes. Left part is physical as right part is chemical.

FIG. 9—shows the crystal structure of Mg-vermiculite projected on (010) plane.

FIG. 10—shows the concept of copper vermiculite using as antimicrobial materials. Top: preparation of copper vermiculite; lower: applications of copper vermiculite.

FIG. 11—shows particle size distribution of jet-milled vermiculite powder (VV-CCE).

FIG. 12—shows the SEM images of vermiculite particles. (1) VV-5; (2) VV-CCE; (3) VV-7.

FIG. 13—shows XRD patterns of VV-5, VV-CCE and VV-7. V(001)—(001) peak of vermiculite; B—new (001) peak of vermiculite after exfoliation; M—magnesiohonblende.

FIG. 14—shows a new peak (Site B, $d_{001}$=0.9818 nm) only occurs after calcining VV-CCE at 950° C. A—(001) peak of vermiculite.

FIG. 15—shows a new peak (Site B, $d_{001}$=0.9818 nm) resulted from calcining VV-5 at 950° C. A—(001) peak of vermiculite.

FIG. 16—shows a flowchart of CEC sampling of ammonium-vermiculite.

FIG. 17—shows a flowchart of ammonium measurement of vermiculite.

FIG. 18—shows interlayer spacing of vermiculite (VV-CCE) reduced after cation exchange with ammonium. (A)—original (001) peak; (B)—new (001) peak after cation exchange.

FIG. 19—shows interlayer spacing of vermiculite (VV-5) reduced after cation exchange with ammonium. (A)—original (001) peak; (B)—new (001) peak after cation exchange.

FIG. 20—shows interlayer spacing of vermiculite (VV-7) reduced after cation exchange with ammonium. (A)—original (001) peak; (B)—new (001) peak after cation exchange.

FIG. 21—shows structure comparison of vermiculite before and after soaking using methanol concentrate. (1)—coarse ammonium-vermiculite (from VV-5) vs. VV-5; (2) micron-sized ammonium-vermiculite vs. VV-CCE.

FIG. 22—shows SEM images of jet-milled Virginia vermiculite (VV-CCE).

FIG. 23—shows SEM images of copper vermiculite (MCV).

FIG. 24—shows SEM image of exfoliated vermiculite (VV-7).

FIG. 25—shows SEM images of exfoliated copper vermiculite (MECV).

FIG. 26—shows comparison of XRD patterns of copper vermiculite (MCV) and Jet-milled vermiculite (VV-CCE).

FIG. 27—shows comparison of XRD patterns of exfoliated copper vermiculite (MECV) and exfoliated vermiculite (VV-7).

FIG. 28—shows layered structure model of copper vermiculite. Cu (hydrated form) is located in the interlayer regions of aluminosilicate sheets, enabling the slow-release of Cu when added in materials. (Projection normal to ac plane).

FIG. 29—shows relation of absorption versus bacterial density of S. aureus.

FIG. 30—shows relation of absorbance vs. bacteria density of E. coli (CFU/ml) at 600 nm.

FIG. 31—shows procedure for determining presence of antimicrobial activity—liquid diffusion method (for supernatant). (Modified from ASTM 2149 term 12).

FIG. 32—shows procedure for determining presence of antimicrobial activity—solid diffusion method (for powder disc).

FIG. 33—shows antibacterial efficiency of supernatants of jet-milled vermiculite and copper vermiculite against S. aureus. Left-jet-milled vermiculite, boiled at 80° C. for 3 hour; right-copper vermiculite, leached with shaking for 1 hour. Picture was taken after plates incubated at 37° C. for 24 hours.

FIG. 34—shows antibacterial efficiency of supernatants of coarse vermiculite (VV-5) and coarse copper vermiculite against S. aureus. Left—leaching solution of coarse vermiculite (shaked for 1 hour); right—coarse copper vermiculite (shaked for 1 hour). Picture was taken after incubated at 37° C. for 24 hours.

FIG. 35—shows antibacterial efficiency of supernatants of copper vermiculite (MCV) and exfoliated copper vermiculite (MECV) against S. aureus. Left-leaching solution of MCV; right-leaching solution of MECV. Solutions were shaked for 1 hour while leaching. Pictures were taken after plates incubated at 37° C. for 14 hours.

FIG. 36—shows antibacterial efficiency of supernatants (28 days shaking) of copper vermiculite (MCV) and exfoliated copper vermiculite (MECV) against S. aureus. Upper-MCV; lower-left-MECV; lower-right-distilled water. Test sample were leaching for 28 days with shaking. Pictures were taken after plates incubated at 37° C. for 14 hours.

FIG. 37—shows antibacterial efficiency of supernatants of copper vermiculite (MCV) and exfoliated copper vermiculite (MECV) against K. pneumoniae. Left-MCV; right-MECV, leaching solution after shaking for 1 hour. Picture was taken after incubated for 18 hours.

FIG. 38—shows antibacterial efficiency of supernatants of copper vermiculite (MCV) and exfoliated copper vermiculite (MECV) against E. coli. (Incubated at 37° C. for 24 hours; left-MCV; right-MECV).

FIG. 39—shows antibacterial efficiency of supernatants (28 days leached) of copper vermiculite (MCV) and exfoliated copper vermiculite (MECV) against E. coli. Upper-MCV; lower-left—MECV; lower-right—distilled water. Test solutions were leached for 28 days with shaking (Incubated at 37° C. for 24 hours).

FIG. 40—shows antibacterial effect of copper vermiculite (MCV) disc against S. aureus. Left-VV-CCE (control, 0.05 g); right-MCV (0.05 g). Media used was TGEA. Pictures were taken after plates incubated at 37° C. for 24 hours.

FIG. 41—shows antibacterial effect of copper vermiculite (MCV) disc against S. aureus on TSA. Left—MCV, dried powder (0.05 g); right—VV-CCE, dried powder (0.05 g, control). Pictures were taken after incubated at 37° C. for 14 hours.

FIG. 42—shows antibacterial effect of exfoliated copper vermiculite (MECV) disc against S. aureus on TSA. Left—MECV (0.02 g); right—VV-7 (0.02 g, control). Pictures were taken after incubated at 37° C. for 14 hours.

FIG. 43—shows antibacterial effect of copper vermiculite (MCV) disc against *K. pneumoniae* on TSA. Left—copper vermiculite (MCV); right—microsized vermiculite (VV-CCE, control); samples were dried powder (0.04 g).

FIG. 44—shows antibacterial effect of exfoliated copper vermiculite (MECV) disc against *K. pneumoniae*. Left—MECV (0.03 g); right—VV-7 (0.03 g, control) (Media: TSA).

FIG. 45—shows antibacterial effect of copper vermiculite (MCV) disc against *E. coli* on TSA. Upper-left—MCV (0.05 g); upper-right—VV-CCE (0.05 g, control). Lower-left—MECV (0.02 g); lower-right—VV-7 (0.02 g, control). Samples were incubated at 37° C. for 14 hours.

FIG. 46—shows the model of antibacterial effects of copper vermiculite by solid diffusion method. Cv—copper concentration in vermiculite; CI—copper concentration to effectively inhibit bacterial growth on agar surface.

FIG. 47—is the model of antibacterial effects of copper vermiculite (and exfoliated copper vermiculite) by liquid diffusion method. Cv—copper concentration in vermiculite; Cs—copper concentration in solution; CB—copper concentration at the edge of vermiculite particles; CI—copper concentration to effectively inhibit bacterial growth on agar surface.

FIG. 48—shows the copper vermiculite impacts on *E. coli*. Control—inoculum only in buffer solution; VVCCE—vermiculite (control 2) 10.0 mg, without Cu; content of Cu-vermiculite (Cu concentration) in solution: 1.0 mg=10 ppm (0.255 ppm); 5.0 mg=50 ppm (1.275 ppm); 10.0 mg=100 ppm (2.55 ppm); 20.0 mg=200 ppm (5.10 ppm).

FIG. 49—shows the exfoliated copper vermiculite impacts on *E. coli*. Control—inoculum only in buffer solution; content of exfoliated copper vermiculite (Cu concentration) in solution: 1.0 mg=10 ppm (0.23 ppm); 2.5 mg=25 ppm (0.59 ppm); 5.0 mg=50 ppm (1.17 ppm); 10.0 mg=100 ppm (2.34 ppm); 20.0 mg=200 ppm (4.68 ppm).

FIG. 50—shows the antifungal effect of copper vermiculite. From left to right: upper: white bentonite, VV-CCE, VV-7; lower: kaolin, copper vermiculite, exfoliated copper vermiculite. (1) at initial time (o hour); (2) incubated for 48 hours; (3) incubated for 21 days.

FIG. 51—shows absorption mechanism between copper vermiculite particle and microbial cell.

FIG. 52—shows leaching rate of major metals in copper vermiculite in water solution.

FIG. 53—shows soaking rate of major metals in copper vermiculite in water solution FIG. 54—shows leaching rate of major metals in copper vermiculite in water solution FIG. 55—shows soaking rate of major metals in exfoliated copper vermiculite in water solution FIG. 56—shows leaching and soaking methods for determining release rate of copper. Cv—metal concentration in vermiculite; Cs—metal concentration in solution; CB—metal concentration at the edge of vermiculite particles.

FIG. 57—shows the comparison of release rates of copper ions from different samples. LMCV-leached solution of MCV; LMECV-leached solution of MECV; SMCV-soaked solution of MCV; SMECV-soaked solution of MECV.

DETAILED DESCRIPTION OF THE PREFERRED EMBODIMENTS

Vermiculite is a naturally occurring layer-structured mineral, which is composed of alternative aluminum silicate sheets and hydrate cation sheets. The aluminum silicate sheet of vermiculite is further made up of two silicon-oxygen octahedral layers and one aluminum-oxygen tetrahedral layer. Since the silicon ions in silicon-oxygen tetrahedral layer are often substituted by trivalent cations such as $Al^{3+}$, $Fe^{3+}$, and the aluminum ions in the aluminum-oxygen octahedral layer are substituted by bivalent cations such as $Mg^{2+}$, $Fe^{2+}$, $Ca^{2+}$, the aluminum silicate sheets of vermiculite thus are usually negatively charged. This requires extra cations in the interlayer regions to maintain chemical equilibrium. Naturally, the cations in the interlayer regions of vermiculite are generally magnesium ions (may contain few calcium or potassium, etc.), which hydrated and combined with the silicate sheet by water molecules. The cations in the interlayer region are exchangeable and can be easily replaced in the laboratory by cation exchange reaction. Vermiculite has excellent cation exchange capacity. Typically, bulk density of vermiculite is 800-1120 kg/m³ (50-70 lb/ft³). The cation exchange capacity of vermiculite concentrates reach 50-150 mmol/100 g, which depends on impurity of vermiculite and particle size.

Within the interlayer regions of vermiculite, water molecules will transform into steam when rapidly heated to high temperature (around 850° C. or higher). The pressure of the steam forces the silicate sheets apart from each other, causing the dramatic increase of volume of vermiculite particles (expansion, usually called exfoliation). Thermally exfoliated vermiculite has very unique properties, such as lightweight (low density), high porosity, specific surface area, high aspect ratio of laminates, and high cation exchange capacity. For example, the commercial products of exfoliated vermiculite of the Virginia Vermiculite LLC, Louisa, Va., "Milled No. 7" has a bulk density of 96-160 kg/m³ (6-10 lb/ft³), aspect ratio up to 20,000, and cation exchange capacity of 50-150 mmol/100 g.

Clay minerals have similar silicate sheets and exchangeable ions in the structures with vermiculite. However, vermiculite is significantly distinguished from clay minerals due to its high layer charge that results in a high cation exchange capacity, unique exfoliation function, special interlayer cations, and a larger particle size. It was therefore classified to different mineralogical groups by mineralogists. Furthermore, exfoliated vermiculite has unique properties, such as lightweight, high porosity, and high cation exchange capacity.

It has been known that some transition metals exhibit antimicrobial activities. These metals include silver, copper, zinc, nickel, manganese, lead, cadmium, and cobalt, etc. Because of the toxicity of some of these metals to human and animals, and antimicrobial efficiency, only copper, silver, zinc, and manganese are suitable to be utilized in the products directly contacting with human and animals. Among these metals, silver and copper are the most effective elements. Other metals such as lead, arsenic, mercury, and cadmium also have strong antimicrobial properties, but are difficult to deploy safely.

Metallic ions on the surface of a product that are in contact with microorganisms disrupt the metabolism and replication functions of the cells, which inhibits the growth of microorganisms. In general, the antimicrobial mechanism of transition metals is believed to result from their strong ionic nature. Once the metallic ion of transition metals diffuse across the cell membrane of pathogenic microbes by various pathways, it inhibits the enzymatic activity by substituting native metal ions within an enzyme. The antimicrobial activity may be explained by one or more different mechanisms. Ionic metals have stronger antimicrobial efficiency than their pure bulk metals, alloys, or nano-scaled particles. Nano-scaled metallic particles usually consist of a metallic core which is surrounded by metal oxide. This affects the release of metallic ions, and increases product costs due to excessive metals added.

The current invention provides novel antimicrobial exfoliated vermiculite compound and corresponding synthetic production thereof. This antimicrobial compound is composed of exfoliated vermiculite and metal ions having antimicrobial property, which includes copper, silver, zinc, manganese, and nickel. The exfoliated vermiculite antimicrobial compound is prepared by implanting antimicrobial metallic ions into the structure of exfoliated vermiculite through cation exchange reactions and surface absorption. The target metals can be implanted into or absorbed on vermiculite particles by at least one or more of the following simplified reactions:

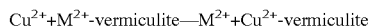
$$Cu^{2+}+M^{2+}\text{-vermiculite}—M^{2+}+Cu^{2+}\text{-vermiculite}$$

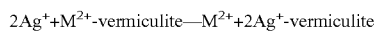
$$2Ag^{+}+M^{2+}\text{-vermiculite}—M^{2+}+2Ag^{+}\text{-vermiculite}$$

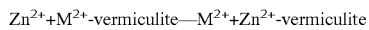
$$Zn^{2+}+M^{2+}\text{-vermiculite}—M^{2+}+Zn^{2+}\text{-vermiculite}$$

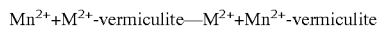
$$Mn^{2+}+M^{2+}\text{-vermiculite}—M^{2+}+Mn^{2+}\text{-vermiculite}$$

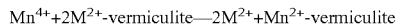
$$Mn^{4+}+2M^{2+}\text{-vermiculite}—2M^{2+}+Mn^{2+}\text{-vermiculite}$$

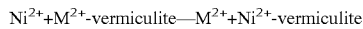
$$Ni^{2+}+M^{2+}\text{-vermiculite}—M^{2+}+Ni^{2+}\text{-vermiculite}$$

where M represents the exchangeable ions within the interlayer regions of exfoliated vermiculite. Usually, the exchangeable ions are magnesium ions even though the vermiculite from some ore deposits partially contain calcium and potassium. Therefore, copper is the best metal for making exfoliated vermiculite antimicrobial compound, since copper has same equivalent charge and the closest ionic radius with magnesium [the ionic radius of magnesium ($Mg^{2+}$) is 0.075 nm, copper ($Cu^{2+}$) is 0.072 nm]. However, when the single species of antimicrobial metals loaded in the exfoliated vermiculite is replaced by a combination of multiple elements, the exfoliated vermiculite can exhibit a broader antimicrobial spectrum, and a smaller amount of individual metal needed.

As used herein, an antimicrobial material herein refers to a material that has sufficient antimicrobial activity to have a beneficial effect. The antimicrobial activity of this invention includes antibacterial, antifungal, antialgal, antiviral, anti-biofilm, anti-inflammatory, bactericidal, fungicide, microbicide, germicide, bacteriostatic, fungistatic, decontamination, degerm, disinfectant, sanitize.

This invention features an exfoliated vermiculite that contains at least one of the individual metals, copper, silver, zinc, nickel, or manganese through a synthetic process.

The metal element implanted into vermiculite structure and surface can be individual or complex of two or more of these elements. These metal elements are ionic state in vermiculite, but can contain a part of nanometer particles of these metals. In some embodiments, this exfoliated vermiculite can include at most about 20% weight percent of the metal elements. In addition to one or more metal elements, such exfoliated vermiculite can contain metal oxides, metal hydroxides, metal nitrides, metal carbides, metal phosphates, metal silicates, metal borides, metal sulfides, metal halides, metal hydrides, metal nitrates, metal carbonates, metal sulfadiazines of these elements.

Generally, the method of making this said exfoliated vermiculite of the present invention is cation exchange process, which includes steps:

(1) Preparing the initial exfoliated vermiculite. The preferred grain size of exfoliated vermiculite is smaller than 75 microns.

(2) Preparing the metal solution, which contains 0.01-1.0M metals descried above (0.01-1.0 mole metal in a liter of water). The optimistic metal concentration is between 0.1-0.2M.

(3) Dissolving the initial exfoliated vermiculite into above metal solution in a desired ratio between approximately 1:5 and 1:100 [based on the ratio of grams of exfoliated vermiculite (in dry ingredient) vs. metal solution (ml)], depending on the specific metal to be solved and reaction conditions. The optimistic ratio is between approximate 1:10-1:30.

(4) Adjusting the pH value of the solution to 1-6 with acid and alkaline solutions.

(5) Heating above solution (suspension) to 40° C.-90° C. with a conventional heater, and maintaining the temperature for 1-8 hours, while continuously blending the solution with a common mechanic blender, magnetic stirrer, or by hand. This step can also been carried out at room temperature, while it last for over 4 hours.

(6) Filtering the suspension (slurry) after reaction with filter paper or a pressure filter. Washing the residue with distilled water, and then dries the vermiculite cake in a drying processor such as furnace and oven at 100° C.-110° C. for at least 0.5 hours.

(7) Grinding the dried exfoliated vermiculite cake in a grinding processor such as mill into the form of powder.

This dried powder is said antimicrobial exfoliated vermiculite compound.

In present invention, exfoliated vermiculite is used as the carrier of the metals having antimicrobial property. The initial exfoliated vermiculite can be naturally commercial products of exfoliated vermiculite or ground products after exfoliation of vermiculite. The particle size can vary, depending upon the application requirement.

In step (2), the metals used should be one or more of following elements: copper, silver, zinc, nickel, or manganese. The metals can be obtained from any types of solvable metal oxides, metal hydroxides, metal sulfides, metal sulfates, metal chlorides, metal nitrates, metal carbonates, metal phosphates, metal hydrides, and metal sulfadiazines of these elements. It also can be waste water containing ions of these metals, such as copper mine drains, electrowinning wastewaters.

When silver was included in the metal solution, this making procedure should be taken in a dark room. Otherwise, all the containers to treat silver solution, suspension, and cake should be non-transparent or brown, and covered to prevent the affect of ultraviolent.

In step (3), the process should be carried out in a reactor. The reactor can be made from glass, ceramic, plastic, metals or alloy such as stainless steel.

In step (4), the pH value can be adjusted by general solution of chemical reagents, such as HCl and NaOH. The optimistic pH value for the reaction is 2.5-4.

In step (5), the optimistic reaction temperature is 55° C.-85° C. For example, 85° C.-90° C. for metal nitrates, 70° C.-80° C. for metal chloride, 90° C.-95° C. for metal carbonates. The optimistic reaction duration is 2-3 hours. This step can also been carried out at room temperature, while it last for over 4 hours.

In step (6), the drying process can be performed in any conventional furnace, oven, or spraying dryer having an inlet temperature of 190° C. and an outlet temperature of 105° C.

An alternative method to prepare exfoliated vermiculite is to carry out cation exchange reaction of vermiculite to obtain unexfoliated vermiculite containing desired metal(s), then fire unexfoliated vermiculite at certain temperature so that obtain exfoliated vermiculite antimicrobial additive. Generally, the method of making such exfoliated vermiculite includes steps:

(a) Preparation of initial vermiculite concentrate (unexfoliated). This vermiculite concentrate can be obtained from vermiculite producers in various specifications. It can be further processed to get desired particle size distribution of vermiculite.

(b) Preparation of metal solution, which contains 0.01-1.0M metals descried above (0.01-1.0 mole metal in a liter of water). The optimistic metal concentration is between 0.1-0.2M.

(c) Dissolving the initial vermiculite concentrate into above metal solution in a desired ratio between approximately 1:5 and 1:100 [based on the ratio of grams of vermiculite concentrate (in dry ingredient) vs. metal solution (ml)], depending on the specific metal to be solved and reaction conditions. The optimistic ratio is between approximate 1:10-1:25.

(d) Adjust the pH value of the solution to 1-6 with acid and alkaline solutions.

(e) Heating above solution (suspension) to 40° C.-90° C. with a conventional heater, and maintain the temperature for at least 0.5 hours, while continuously blending the solution with a common mechanic blender, magnetic stirrer, or by hand.

(f) Filter the suspension (slurry) after reaction with filter paper or pressure filter. Washing the residue with distilled water, and then dries the vermiculite cake to reduce the moisture to approximate 5-15 weight percent (prefer to 8-12 weight percent). Grind the cake into the form of powder or granules in a mill.

(g) Exfoliation of vermiculite powder or granule. Fire the vermiculite powder or granule at 850° C.-1000° C. in a furnace. This process can be carried out by any current industry process for exfoliation of vermiculite.

This powder is said antimicrobial exfoliated vermiculite compound.

In step (b), the metals used should be one or more of following elements: copper, silver, zinc, nickel, or manganese. The metals can be obtained from any types of solvable metal oxides, metal hydroxides, metal sulfides, metal sulfates, metal chlorides, metal nitrates, metal carbonates, metal phosphates, metal hydrides, and metal sulfadiazines of these elements. It also can be waste water containing ions of these metals, such as copper mine drains, electrowinning wastewaters.

When silver was included in the metal solution, this making procedure should be taken in a dark room. Otherwise, all the containers to treat silver solution, suspension, and cake should be non-transparent or brown, and covered to prevent the affect of ultraviolent.

In step (c), the process should be carried out in a reactor. The reactor can be made from glass, ceramic, plastic, metals or alloy such as stainless steel.

In step (d), the pH value can be adjusted by general solution of chemical reagents, such as HCl and NaOH. The optimistic pH value for the reaction is 2.5-4.

In step (e), the optimistic reaction temperature is 55° C.-95° C. For example, 85° C.-90° C. for metal nitrates, 70° C.-80° C. for metal chloride, 90° C.-95° C. for metal carbonates. The optimistic reaction duration is 2-3 hours.

In step (f), the drying process can be carried out by using a spray dryer, or by heating the vermiculite cake in a drying equipment such as furnace or oven at 100° C.-110° C. for at least 0.5 hours, and then use a mill to get the cake into the form of powder or granules. When spray drying process is employed, the vermiculite cake should be previously mixed deionized water and uniformly blended in a ratio of 1.0 gram vermiculite (in dry ingredient) vs. 0.5 gram water. The working temperature of the spray dryer can be approximately controlled at an inlet temperature of 190° C. and an outlet temperature of 105° C.

The following examples are illustrative of the present invention and are not intended to restrict the scope of the invention as set forth in the appended claims.

Example 1

Prepared 0.1M copper solution by dissolving 25 grams of pentahydrated copper sulfate, $CuSO_4.5H_2O$ into 1000 ml of deionized water. Weighed and placed 100 grams of dried exfoliated vermiculite (commercially product, "Milled No. 7", available from Virginia Vermiculite LLC, Louisa, Va.) into a 5 liter of stainless steel reactor, then poured 3000 ml 0.1M copper solution into the reactor, adjusted pH value of the solution to 3-4 with 1M NaOH solution and 10% HCl solution. Heated the solution and maintained the temperature at around 80° C. Gently blended the suspension for 2 hours for complete reaction. The suspension after reaction was filtered with filter paper or pressure filter. The residue was washed with distilled water, and then dried at 100° C. for 2 hours. The dried powder was said antimicrobial exfoliated vermiculite composite material.

By chemical analysis, this dried antimicrobial exfoliated vermiculite contains 3.6 weight percent of metal copper.

Example 2

Prepared 0.2M silver solution by dissolving 34 grams of silver nitrate, $AgNO_3$ into 1000 ml of deionized water. Weighed and placed 10 grams of dried exfoliated vermiculite (commercially product, "Milled No. 7", available from Virginia Vermiculite LLC, Louisa, Va.) into a 500 ml brown glass flask, then poured 250 ml 0.2M silver solution into a chemical reactor, placed a magnetic stirrer which 0.5 inches in length and covered with Teflon, adjusted pH value of the suspension to 3-4 with 10% HCl solution. Put the suspension onto a hotplate, heated the suspension and maintained the temperature at around 85° C. Blended the suspension with the magnetic stirrer for 2 hours for complete reaction. The suspension after reaction was filtered with filter paper. The residue was washed with deionized water, and then dried at 100° C. for 2 hours. The dried powder was said antimicrobial exfoliated vermiculite composite material.

This procedure was completed in a dark room. All the containers to treat silver solution, suspension, and cake were non-transparent and covered to prevent the affect of ultraviolent.

By chemical analysis, this dried antimicrobial exfoliated vermiculite contains 6.2 weight percent of metal silver.

Example 3

0.1M copper solution was prepared by dissolving 14 grams of copper chloride, $CuCl_2$ into 1000 ml of deionized water. Weighed and placed 50 grams of exfoliated vermiculite (commercially product, "Milled No. 7", from Virginia Vermiculite LLC, Louisa, Va.) into a 3 liter of stainless steel reactor, then poured 1500 ml 0.1M copper solution into the reactor, adjusted pH value of the solution to 3-4 with 1M NaOH solution and 10% HCl solution. Gently blended the suspension for 8 hours for complete reaction. Filtered the suspension with filter paper. The residue was washed with distilled water, and then dried at 100° C. for 2 hours.

The dried powder was said antimicrobial exfoliated vermiculite composite material. According to chemical analysis, this dried antimicrobial exfoliated vermiculite contents 3.2 weight percent of metal copper.

Example 4

Exfoliated vermiculite (commercially product of Virginia Vermiculite LLC, Louisa, Va., "Milled No. 7") were ground into micron-sized powder through a jet mill. This process provided micron-sized exfoliated vermiculite. All the particles in this powder were less than 10 microns.

Prepared 0.1M copper solution by dissolving 24 grams of trihydrated copper nitrate, $Cu(NO_3)_2.3H_2O$ into 1000 ml of deionized water. Weighed and placed 100 grams of dried micron-sized exfoliated vermiculite into a 5 liter of stainless steel reactor, then poured 3000 ml 0.1M copper solution into the reactor, adjusted pH value of the solution to 3-4 with 1M NaOH solution and 10% HCl solution. Heated the solution and maintained the temperature at around 85° C. The suspension was gently blended for 2 hours for complete reaction. The suspension after reaction was filtered with a pressure filter. The residue was washed with distilled water, and then dried at 100° C. for 2 hours.

The dried powder was said antimicrobial exfoliated vermiculite composite material. By chemical analysis, this dried antimicrobial exfoliated vermiculite contents 3.5 weight percent of metal copper.

Example 5

Exfoliated vermiculite (commercially product of Virginia Vermiculite LLC, Louisa, Va., "Milled No. 7") were ground into down 325 meshes (45 microns) via a ball mill. This process provided fine exfoliated vermiculite powder. All the particles in this powder were less than 45 microns.

The following ingredients were combined and mixed together to form a substantially homogeneous multi-metal solution, which contains ions of 0.05M copper, 0.04M silver, 0.04M Zinc and 0.01M Manganese:
$CuSO_4.5H_2O$, chemical reagent, 13 grams
AgNO3, chemical reagent, 7 grams
$ZnSO_4.7H_2O$, chemical reagent, 12 grams
$MnSO_4$—$H_2O$, chemical reagent, 1.7 grams In a traditional dark room without ultraviolent, mixed and placed above compound in a 2000 ml glass flask, brought to 1000 ml with deionized water to form multi-metal solution. Weighed and placed 100 grams of dried fine exfoliated vermiculite into a 5 liter of conventional stainless steel reactor with electricity heater, then poured 3000 ml multi-metal solution into the reactor, adjusted pH value of the solution to 3-4 with 10% HCl solution. Heated the suspension and maintained the temperature at approximate 85° C. The suspension was gently blended for 2 hours while being heating. The suspension after reaction was filtered with a pressure filter. The residual wetcake was washed with distilled water, and then dried at 100° C. for 2 hours.

The dried powder was said antimicrobial multi-metal exfoliated vermiculite composite material. According to chemical analysis, this dried multi-metal exfoliated vermiculite contains metals in weight percent: Ag 1.1, Cu 2.6, Zn 0.8, and Mn 0.3.

Example 6

Taken 1.0 lbs of exfoliated vermiculite (commercially product of Virginia Vermiculite LLC, Louisa, Va., "Milled No. 7") into a 2 gallon stainless steel reactor, then poured 5000 ml copper mining draining into the reactor, adjusted pH value of the solution to 3 with 10% HCl solution. The suspension was blended with a stainless blender at room temperature for 24 hours. The suspension after reaction was filtered with a pressure filter. The residual wetcake was washed with distilled water, and then dissolved to form a slurry with 200 ml additional water. The slurry was then spray dried in a conventional spray dryer equipped with a single fluid nozzle and having an inlet temperature of 190° C. and an outlet temperature of 105° C. The resulting granular product was dry and has an average particle size of approximately 200 microns.

The resulting granular product was said antimicrobial exfoliated vermiculite composite material. This dried exfoliated vermiculite contains 1.3 weight percent of metal copper.

Example 7

The following ingredients were combined and mixed together to form a substantially homogeneous multi-metal solution, which contains ions of 0.1M copper and 0.04M silver:
$Cu(NO_3)_2.3H_2O$, 24 grams
$AgNO_3$, 7 grams In a traditional dark room without ultraviolent, mixed and placed above compound in a 2000 ml glass flask, brought to 1000 ml with deionized water to form multi-metal solution. Weighed and placed 10 grams of dried exfoliated vermiculite (commercially product of Virginia Vermiculite LLC, Louisa, Va., "Milled No. 7") into a 500 ml glass flask, then poured 300 ml multi-metal solution into the reactor, adjusted pH value of the solution to 3.5 with 10% HCl solution. Heated the suspension on a conventional hotplate and maintained the temperature at approximate 85° C. The suspension was gently blended for 1.5 hours while being heating. The suspension after reaction was filtered with filter paper. The residual wet cake was washed with distilled water, and then dried at 100° C. for 2 hours.

The resulting dried powder was said antimicrobial multi-metal exfoliated vermiculite composite material. According to chemical analysis, this dried multi-metal exfoliated vermiculite contains metals in weight percent: Ag 1.2, Cu 2.9.

Example 8

Prepared 0.12M copper solution in a 2000 ml glass flask by dissolving 30 grams of pentahydrated copper sulfate, $CuSO_4.5H_2O$ into 1000 ml of deionized water. Weighed and placed 100 grams of vermiculite concentrate (commercially product of the Paladora America Ltd., Kennesaw, Ga., USA. "Grade Fine", which has particle size of 0.7-2.0 mm, bulk density of 850-1050 kg/m3) into a 1 gallon glass reactor, then poured 2000 ml of 0.12M copper solution into the reactor, adjusted pH value of the suspension to around 3.5 with 1M NaOH solution and 10% HCl solution. Put the suspension with reactor onto a conventional hotplate, heated the suspension and maintained the temperature at 83° C. for 3.5 hours. Gently blended the suspension with a stainless steel blender during the heating for complete reaction. The suspension after reaction was filtered with a pressure filter with filter paper. The residual wetcake was washed with deionized water, and then dried at 100° C. in an electricity oven for 2 hours to reduce the moisture to approximate 10 weight percent. The dried cake was milled into the form of powder. Placed the dried vermiculite powder with a stainless steel trap in an electricity furnace (previously heated to 900° C.) for exfoliation, and kept for 20 seconds, then took off the vermiculite powder to cool to room temperature.

This fired powder was this said antimicrobial exfoliated vermiculite composite material. This fired powder can also be milled into various specifications of particle size distribution, depending onto the application demands. By chemical analysis, this exfoliated vermiculite contains 4.2 wt % metallic copper.

Research Study Results

The advantages of antimicrobial exfoliated copper vermiculite over antimicrobial unexfoliated copper vermiculite is strongly supported by the results of a research study by the inventors. The most relevant figures from the study comprise the figures in this application and are for illustration purposes only and should not be construed as a limitation on the scope of the present invention.

FIG. 1 shows a sketch of cross sections of unexfoliated vermiculite (left) and exfoliated vermiculite (right). The lines represent aluminum silicate sheets while the dots represent copper cations.

Unexfoliated vermiculite consists of infinitely alternative cell units, each cell made up of an aluminum silicate layer (sheet) and an interlayer region containing hydrated copper cations. During synthetic reaction, copper ions replaced magnesium in the interlayer regions to form copper vermiculite.

Exfoliated vermiculite has macro-interlayer regions resulting from the blasting off of the interlayer water molecules during exfoliation. Most of the aluminum silicate sheets were distorted and moved away from each other. The result is a product with high porosity and high specific surface area, thus providing high absorption of copper and other metals. During the cation exchange reaction, some copper ions substituted magnesium ions into the interlayer regions, while a major part of copper ions were absorbed on the surface of aluminum silicate sheets. This greatly improved the cation exchange capacity of exfoliated vermiculite as well as the release speed of copper from the vermiculite carrier.

On the other hand, the interlayer region of unexfoliated vermiculite can only be implanted by ionic copper. Nanometer copper particles remain on the surface of the silicate sheets. Because of this, exfoliated vermiculite can contain more metal nanometer particles.

Figure 1:
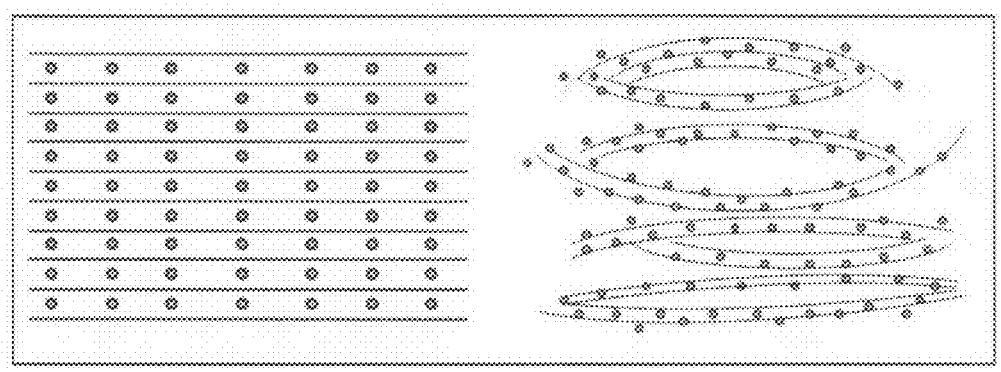
Figure 2:
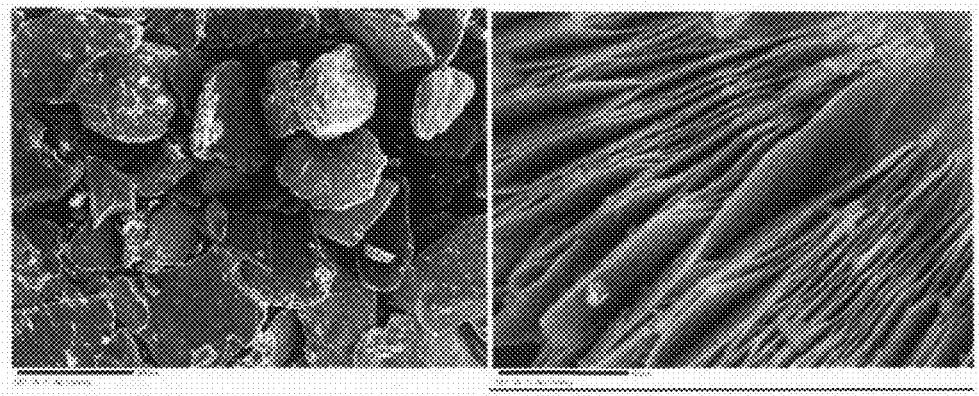
FIG. 2 shows Scanning Electron Microscopy (SEM) images of laminates of unexfoliated (left) and a grain of exfoliated vermiculite (right). Exfoliation exploded the laminate sheets splitting them into thin layers.
Figure 3:
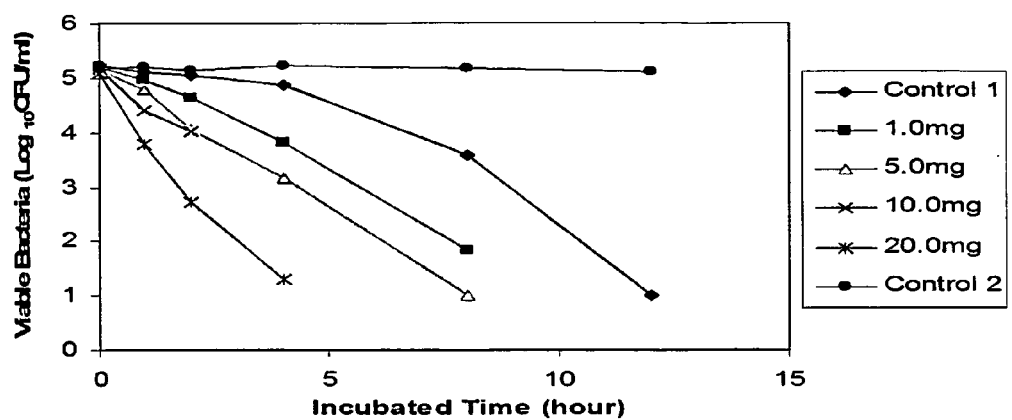
FIG. 3 shows the bactericide activity of unexfoliated vermiculite. With 20.0 mg copper vermiculite in 100.0 ml bacteria dilution (containing 200 ppm copper vermiculite, or 5.10 ppm of copper atoms), the reductions of viable bacteria are 94.8% at 1 hour, 99.6% at 2 hours, and >99.9% at 4 hours.
Figure 4:
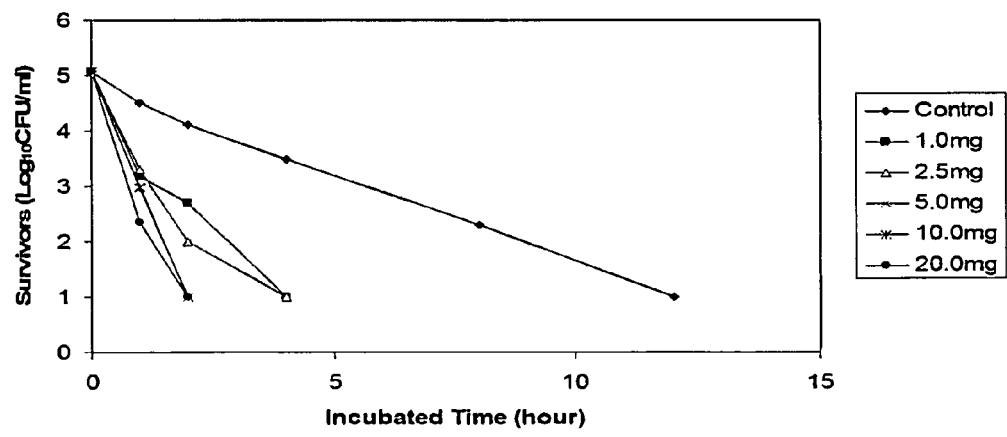

FIG. 4 shows the bactericide activity of exfoliated vermiculite. With 20.0 mg exfoliated copper cermiculite in 100.0 ml bacteria dilution (containing 200 ppm copper vermiculite, or 4.68 ppm of copper atoms), the reduction of viable bacteria are 99.8% at 1 hour and >99.9% at 2 hours. With 1.0 mg exfoliated copper vermiculite in 100.0 ml bacteria dilution (containing 10 pp. copper vermiculite, or 0.234 ppm of copper atoms), the reduction of viable *E. coli* reached 98.7% at 1 hour and 0.95.6% at 2 hours.

Figure 5:
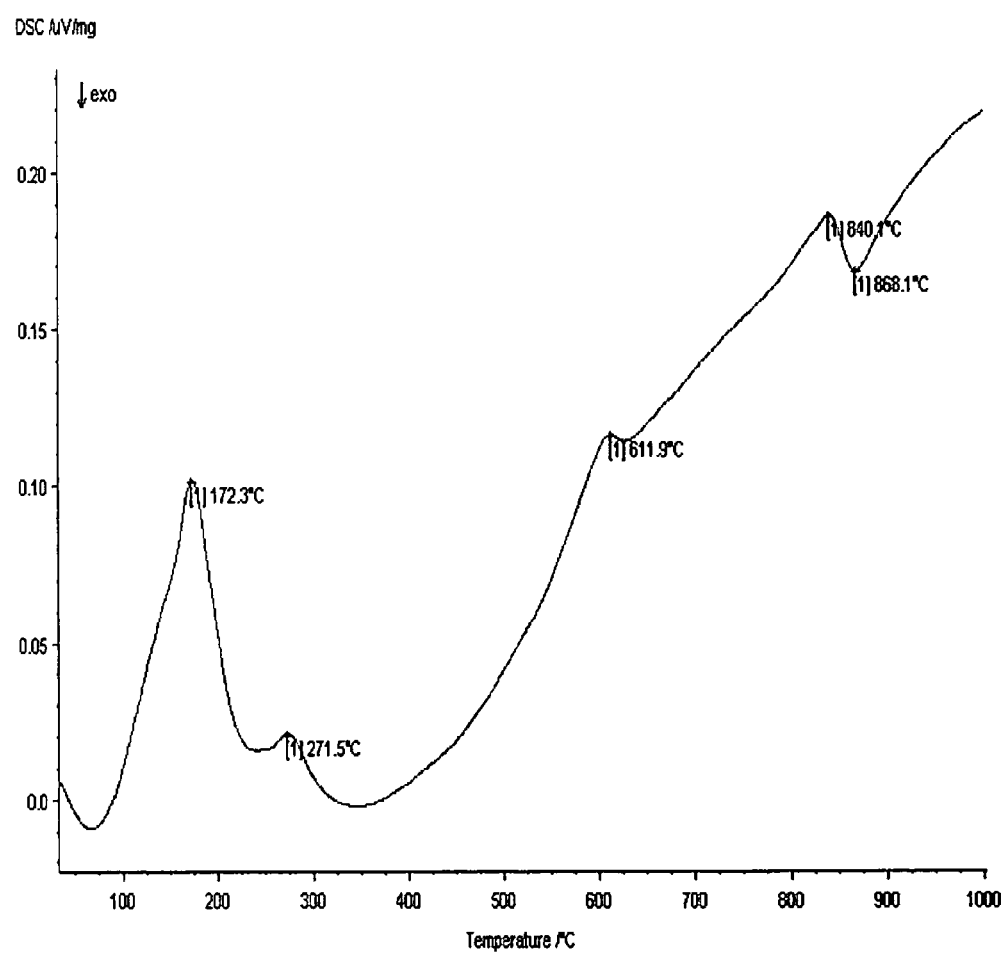

FIG. 5 shows a differential thermal analysis of unexfoliated vermiculite. Unexfoliated vermiculite contains interlayer water molecules. Once the temperature is elevated, it will absorb heat for its early dehydration and phase transformation at 173° C.

Figure 6:
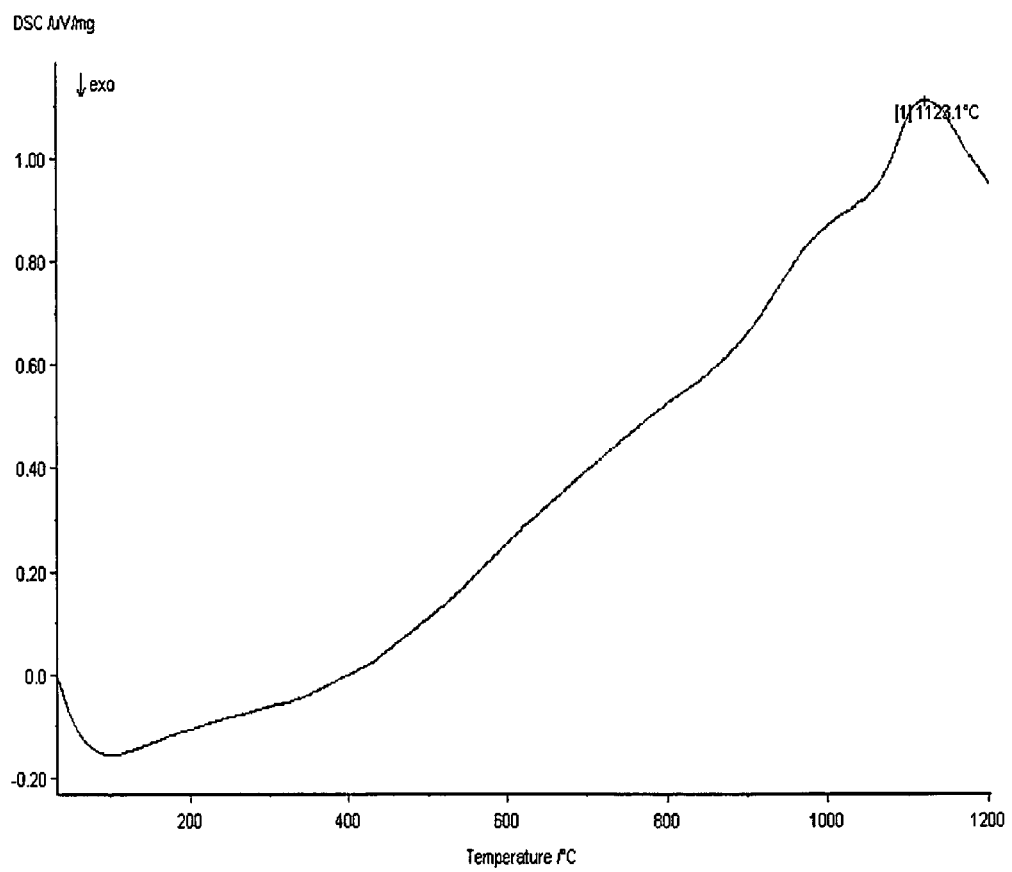

FIG. 6 shows the differential thermal analysis of exfoliated vermiculite. Exfoliated vermiculite absorbs heat only gradually.

The entirety of the research work (85 pages) is disclosed following. Figures of X-ray diffraction (XRD) patterns generated understandably may not show very legible coordinates but nonetheless serve their purpose of showing relevant trends or behavior of the vermiculite material and are explained in the text. For convenient referencing, please adjust the page nos. in the Table of Contents section accordingly.

CHARACTERISTICS AND ANTIMICROBIAL ACTIVITY OF COPPER-BASED MATERIALS

By

BOWEN LI

A DISSERTATION

Submitted in partial fulfillment of the requirements for the degree of

DOCTOR OF PHILOSOPHY (Materials Science and Engineering)

MICHIGAN TECHNOLOGICAL UNIVERSITY

2008

Copyright © Bowen Li 2008

This dissertation, "Characteristics and Antimicrobial Activity of Copper-based Materials," is hereby approved in partial fulfillment of the requirements for the degree of DOCTOR OF PHILOSOPHY in the field of Materials Science and Engineering.

DEPARTMENT: Materials Science and Engineering

Signatures:

Dissertation Advisor _____
_ Jiann-Yang Hwang _

Committee _____
_ Susan T. Bagley_ ___

_____
__Xiaodi Huang_____

_____
_S._Douglas McDowell

Department Chair _____
___Mark R. Plichta_____

Date _____

Abstract

[00133] Along with globalization, more outbreaks of mass infectious incidents caused by pathogenic microbes have increasingly occurred. This has resulted in enormous market demand and intensive world efforts for antimicrobial materials that can be used to protect the public health with surface self-decontamination ability and long durability.

[00134] The antimicrobial products developed so far are mostly organic and/or liquid, which were limited by problems such as chemical stability and low thermal resistance. Some metallic ions, such as silver, copper, zinc, nickel, and manganese, exhibited strong antimicrobial activities. Among these, silver and copper are the most effective elements. Metallic ions on the surface of an appliance that may come in contact with bacteria and other microbes disrupt the normal metabolism and replication functions of these cells. This typically results in microbial death. However, only ionic metals perform antimicrobial activity. How to hold and release the ionic metals appropriately is a significant issue to the development and applications of metal ion-typed antimicrobial materials.

[00135] Application of antimicrobial materials for surface decontamination must meet a series of criteria, such as performance, wide spectrum on pathogens, pre-applied on various kinds of surfaces, safe to human and animals, blendable with various coating materials, long durability and stability, low cost, heat resistance, and environmental friendly, etc. However, currently developed antimicrobial materials could not completely satisfy the above criteria. Although silver-based materials have been well-recognized, their stability, durability, and cost are still issues.

[00136] Copper vermiculite is proposed as the antimicrobial material for this study. Copper has both antibacterial and antifungal properties. It has even better antifungal activity than silver. Vermiculite is a naturally occurring magnesium-based layer-structured mineral. It is an excellent absorber of heavy metal ions. The interlayer regions of vermiculite are negatively charged and mainly filled with exchangeable magnesium ions. Since copper has equivalent charge and an atomic radius similar to magnesium [the ionic radius of magnesium ($Mg^{2+}$) is 0.075 nm, copper ($Cu^{2+}$) is 0.072 nm], the magnesium atoms in the interlayer regions of vermiculite can be easily replaced by copper via a cation exchange process. The copper vermiculite consequently may have the structural and chemical stability that is similar to naturally occurring magnesium vermiculite. The principal advantage of a vermiculite carrier is that the structure is stable under industrial and environmental conditions. Vermiculite can provide a consistent and effective delivery vehicle for antimicrobial agents. Copper ions in the interlayer of vermiculite may be slowly released via cation exchange and delivery to the surface by diffusion. Vermiculite has been extensively used as fillers of fireproof materials, plastics, paints, fertilizers, and environmental remediation material. All of these applications have been proved safe to human contact. Therefore, vermiculite has the potential to be the ideal host for copper ions. The combination of copper ions and vermiculite may generate excellent antimicrobial activities.

[00137] In this study, the proposed copper vermiculite was synthesized, and the characteristics, antimicrobial effects, and chemical stability of copper vermiculite were investigated. Two types of copper vermiculite materials, micron-sized copper vermiculite (MCV) and exfoliated copper vermiculite (MECV), are selected for this research. Since most of the functional fillers used in industry products, such as plastics, paints, rubbers, papers, and textiles prefer micron-scaled particles, micron-sized copper vermiculite was prepared by jet-milling vermiculite. Meanwhile, since the exfoliated vermiculite has very unique properties, such as high porosity, specific surface area, high aspect ratio of laminates, and low density, and has been extensively utilized as a functional additives, exfoliated copper vermiculite also was synthesized and investigated.

[00138] In this study, copper vermiculite was synthesized by a cation exchange process at 80°C, using jet-milled and exfoliated Virginia vermiculite. The resulting atomic content of copper (as $Cu^{2+}$) was 2.55 wt% and 2.34 wt% in copper vermiculite, and exfoliated copper vermiculite, respectively. Copper vermiculite inherited the structure of magnesium vermiculite. Based on field emission scanning electron microscopy images, the copper atoms were homogeneously dispersed in the vermiculite structure.

[00139] The antibacterial efficiency of copper vermiculite was qualitatively evaluated by the diffusion methods (both liquid diffusion and solid diffusion) against the most common pathogenic species: *Escherichia coli (E. coli)*, *Staphylococcus aureus (S. aureus)*, and *Klebsiella pneumoniae (K. pneumoniae)*. Among these microorganisms, *E. coli* and *K. pnemoniae* represent gram-negative bacteria, while *S. aureus* present gram-positive bacteria. The result showed that the release velocity of copper from copper vermiculite is very slow. However, copper vermiculite clearly has excellent antibacterial efficiency to *S. aureus*, *K. pneumoniae* and *E. coli*. The strongest antibacterial ability of copper vermiculite is its action on *S. aureus*. Exfoliated copper vermiculite demonstrated more efficient antibacterial ability than un-exfoliated copper vermiculite, even when less sample amounts were utilized.

[00140] The antibacterial efficiency of copper vermiculite was also quantitatively evaluated by determining the reduction rate (death rate) of *E. coli* versus various levels of copper vermiculite. Overnight (at 37°C) *E. coli* suspensions of $1\sim2\times10^7$ CFU/ml were used. Copper levels of 10 ppm to 200 ppm copper vermiculite (as 0.255 to 5.10 ppm in metal copper) were examined with all experiments repeated three times. In the control vermiculite suspensions, *E. coli* densities remained constant during the 12 hour contact time; in contrast, bacteria levels with copper vermiculite significantly decreased. In the experiment with 200 ppm copper vermiculite (5.10 ppm Cu), viable *E. coli* levels were reduced by 94.8% at 1 hour, 99.6% at 2 hours, and >99.9% at 4 hours. 10 ppm of copper vermiculite in solution is sufficient to reduce the cell population of *E. coli*, while the untreated vermiculite had no antibacterial activity. The slow release of copper revealed that the antimicrobial effect of copper vermiculite was due to the strong interactions between copper ions and bacteria cells.

[00141] Exfoliated copper vermiculite has even stronger antibacterial activity than copper vermiculite against *E. coli*. With 200 ppm exfoliated copper vermiculite in bacteria suspension (4.68 ppm of metal copper), the reduction of viable bacteria are 99.8% at 1 hour, and >99.9% at 2 hours. With 10 ppm exfoliated copper vermiculite in bacteria dilution (0.234 ppm of copper atoms), the reduction of viable *E. coli* reached 98.7% at 1 hour, and >95.6% at 2 hours.

[00142] Molds have the potential to cause health problems, such as allergic reactions, irritations, and mycotoxins, and damage to buildings, historic relics, properties, etc. Since copper has better antifungal property, an initial antifungal activity of copper vermiculite was evaluated in this study. Fat-free milk was used to develop molds in the test samples by saturated samples. Incubated at 36°C for 48 hours, all of the surfaces of untreated control samples, including micron-sized vermiculite, exfoliated vermiculite, bentonite, and kaolin, have been covered by thick mold layers. However, there were no mold showed on copper vermiculite and exfoliated copper vermiculite. Even after the incubation was lasted for 10 days, copper vermiculite and exfoliated copper vermiculite did not show any mold on the surface. These results exhibited copper vermiculite has excellent antifungal activities against mold.

[00143] Stability of copper ions in copper vermiculite was measured by aqueous leaching process. Copper vermiculite and exfoliated copper vermiculite were put into distilled water in a ratio of 2.0g/100ml, and then implemented leaching processes by continuously shaking (leaching) and statically storing (soaking) for desired periods of time, respectively. According to the analytic result by inductively coupled plasma spectroscopy (ICP), the major metals released were copper, magnesium, iron, silicon, and aluminum. The release rate of copper depends on the environmental conditions. Under the dynamic leaching condition, all the major elements had shown linear leaching rates, and slowly increases along with the leaching time. Copper concentration in 1 hour leached solutions had sufficient concentration to inhibit *E. coli* in aqueous solution. Lasting for 1 month, 1 gram of copper vermiculite only released 185μg of copper. At this velocity, 11.5 years are required to completely exhaust the copper atoms from copper vermiculite. A soaking process provided a lower release rate than leaching process.

[00144] Comparably, exfoliated copper vermiculite had lower copper concentration, stronger antimicrobial effect, but faster release rate than copper vermiculite, due to their different structure characteristics.

[00145] Keywords: Copper, vermiculite, decontamination, antibacterial, antifungal, layer structure, stability

Acknowledgements

[00146] I would like to express my appreciations to a number of people who helped me in my research. I am particularly grateful to Professor Jiann-Yang Hwang as my advisor for his guidance and support throughout this research. I deeply appreciate Professor Susan T. Bagley in the Department of Biological Science, particularly for her generous support and guidance for my microbiological research. I am also grateful to Professor S. Douglas McDowell and Dr. Xiaodi Huang as my advisory committee member.

[00147] I want to thank Mr. Ratul Saha and Michael LaBeau in the Department of Biological Science for their kindly helps when I initiated my microbiological lab works; Mr. Ned Gumble at the Virginia Vermiculite LLC, and Ms. Francie Wyatt at the Palabora America Ltd., GA generously provided original vermiculite samples for my experiment; Mr. Tom Redman at the CCE Technologies, Inc. kindly completed the jet-mill process for preparation of micron-sized vermiculite.

[00148] I would like to express my gratitude to the following people who provided me with valuable advice and helps during my research: Professor George Robinson; Dr. Nicholas Nanninga, Dr. Zhiyong Xu, Mr. Robert Virta at the US Geological Survey, Mrs. Allison Hein, Mr. Owen Mills, Mr. Nick Popko, Mr. Shangzhao Shi, and Mr. Xiang Sun.

[00149] Finally, I am thankful to my family for continuing support and love!

Abbreviations Used in This Dissertation

AATCC: the American Association of Texile Chemists and Colorists

ASTM: ASTM International (American Society for Testing and Materials)

CEC: cation exchange capacity

Cu-V: copper vermiculite

ICP: Inductively Coupled Spectroscopy

JIM: Japanese Industrial Standards

MCCV: coarse copper vermiculite (synthezed from VV-5)

MCV: micron-sized copper vermiculite (synthezed from VV-CCE)

MECV: exfoliated copper vermiculite (prepared from VV-7)

MIC: minimum inhibitory concentration

SEM: scanning electron microscopy

TGEA: Tryptone Glucose Extract Agar

TSA: Tryptone Soy Agar

TSB: Tryptone Soy Broth

U.S. EPA: The United States Environmental Protection Agency

VV-5: concentrate product of Virginia Vermiculite, Grade No.5

VV-7: Virginia Vermiculite product, exfoliated, Milled No.7

VV-CCE: jet-milled vermiculite (micron-sized) from VV-5

XRD: X-ray diffraction Method

Table of Contents

Abstract .................................................................................................................... 27

Acknowledgements ................................................................................................ 31

Abbreviations Used in This Dissertation ............................................................ 32

Table of Contents .................................................................................................. 33

1 Introduction ........................................................................................................ 35

1.1 Background .................................................................................................. 35

1.1.1 Microbial Threats to Public Health and Properties ........................... 35

1.1.2 Surface Cleanness and Antimicrobial Materials ................................ 36

1.2. Concept and Objectives of This Research ................................................. 39

1.2.1 Applications of Metallic Copper as Antimicrobial Materials ........... 39

1.2.2 Host Material of Copper Ions .............................................................. 40

1.2.3 Research Objectives .............................................................................. 42

2 Synthesis and Characteristics of Copper Vermiculite ................................... 43

2.1 Preparation of Vermiculite Particles ........................................................... 43

2.1.1 Original Vermiculite Samples .............................................................. 43

2.1.2 Cation Exchange Capacities of Vermiculite ....................................... 45

2.2 Synthesis of Copper Vermiculite ................................................................ 48

2.3 Characterization of Copper Vermiculite .................................................... 49

2.3.1 Chemical Composition and Copper Content of Copper Vermiculite ........... 49

2.3.2 Microtopography of Copper Vermiculite .......................................... 49

2.3.3 Layer Structure of Copper Vermiculite .............................................. 50

2.4 Summary ....................................................................................................... 51

3 Antimicrobial Activities of Copper Vermiculite .............................................. 53

3.1 Test Bacteria ................................................................................................. 53

3.2 Methodology for Antibacterial Assessment ............................................... 54

3.3 Preparation of Materials and Microorganisms .......................................... 57

3.4 Antibacterial Activities of Copper Vermiculite by Diffusion Method ..... 62

3.4.1 Materials and Sampling ....................................................................... 62

3.4.2 Assay Procedures .................................................................................. 62

3.4.3 Results ............................................................................................... 63

3.5 Quantitative Assessment of Antibacterial Effects of Copper Vermiculite ............. 68

3.5.1 Test organism ..................................................................................... 68

3.5.2 Procedure ........................................................................................... 68

3.5.3 Results and Discussions ..................................................................... 69

3.6 Antifungal Activity of Copper Vermiculite ........................................................... 74

3.7 Antimicrobial Mechanism of Copper Vermiculite ................................................ 75

3.8 Summary ................................................................................................................ 77

4 Assessment of Chemical Stability of Copper Vermiculite ........................................ 80

4.1 Goals ...................................................................................................................... 80

4.2 Procedures of Measurement of Leaching Rate ..................................................... 80

4.3 Leaching Rate of Copper Vermiculite ................................................................... 81

4.4 Leaching Rate of Exfoliated Copper Vermiculite ................................................. 83

4.5 Summary ................................................................................................................ 86

5 Expected Applications and Environment Impact of Copper Vermiculite ............. 88

5.1 Potential Application of Copper Vermiculite Antimicrobial Materials ................. 88

5.2 Environmental Impact of Copper Based Antimicrobial Materials ........................ 88

6 Conclusions ................................................................................................................... 91

References ........................................................................................................................ 93

1 Introduction

[00150] The objective of this study is to develop, characterize, and assess copper-based antimicrobial additives that can be utilized as self-decontamination materials in various buildings, hospitals, appliances, tools, etc., to protect the health and properties of the general public.

1.1 Background

1.1.1 Microbial Threats to Public Health and Properties

[00151] More outbreaks of mass infectious incidents caused by pathogenic microbes have occurred in recent years as a result of mass globalization. In the past two decades, many new bacterial diseases have been recognized, such as Legionnaires' disease, toxic shock syndrome, Lyme disease, campylobacteriosis, *E. coli* O157:H7 infections, *Helicobacter* infections, and *Bartonella* infections [1, 2]. Other diseases, such as meningococcal infections, *Salmonella enteritidis* infections, listeriosis, and tuberculosis have increased in frequency in both the industrialized and developing countries [3]. The World Health Organization estimated that nearly 2 million people are killed by tuberculosis each year [4]. Diarrheal diseases kill 2 million children in developing countries each year. Neonatal tetanus is estimated to cause 490,000 deaths per year. 300 million to 500 million new cases of malaria occur worldwide annually, causing at least 2.7 million deaths [5]. The United States is a developed country. Even so, there are 76 million illnesses, 325,000 hospitalizations, and 5,200 deaths in the U.S. each year caused by bacteria alone [6]. More than 2 million people in the U.S. acquire an infection during a hospital stay each year, and an estimated 90,000 people die from them — more than the combination from AIDS, breast cancer and auto accidents [7]. According to the estimation of the U.S. Centers for Disease Control and Prevention (CDC), the annual costs of medical care for treating infectious diseases in the U. S. are about $120 billion [6].

Figure 7:
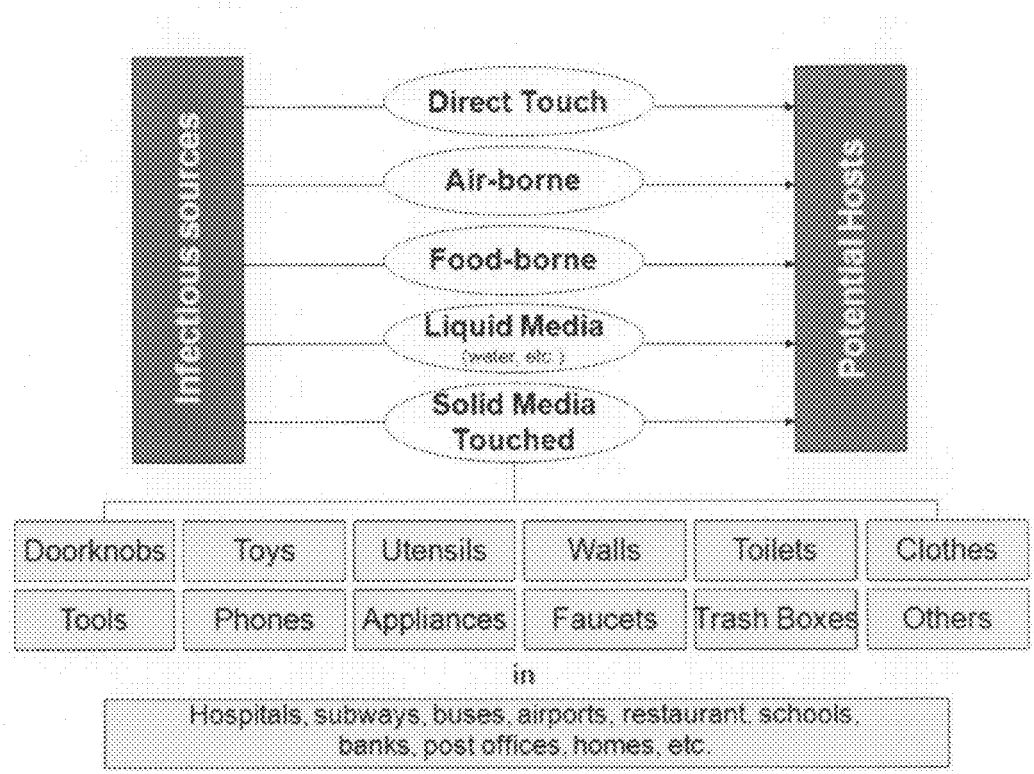

[00152] Infectious microbes are spread from infectious sources to potential hosts through the air, water, or by surface contact (Fig. 7). The survival of microbes in air is generally short in life. Surface contacts, such as touching, are considered as the major transport of infection. Research conducted by Dr. Charles Gerba at the University of Arizona, for example, indicated that the average desktop appliance such as telephone, computer mouse, keyboard, desktop surfaces and microwave door handle harbored 400 times more bacteria than any surface tested in the bathroom [7]. Several surveys have demonstrated that pathogenic microbes are present on and can be transferred by various common objects (e.g., computer keyboards, laundry machines, vacuums, purses) and in many places (e.g., schools, buses, airplanes, kitchens). These investigations have awakened worldwide public concerns and have frequently been followed and reported by the mainstream media and industries [8-14]. The danger from these microbes is potentially growing worse because many hospital-acquired infections can no longer be treated with traditional antibiotics [15].

1.1.2 Surface Cleanness and Antimicrobial Materials

Figure 8:
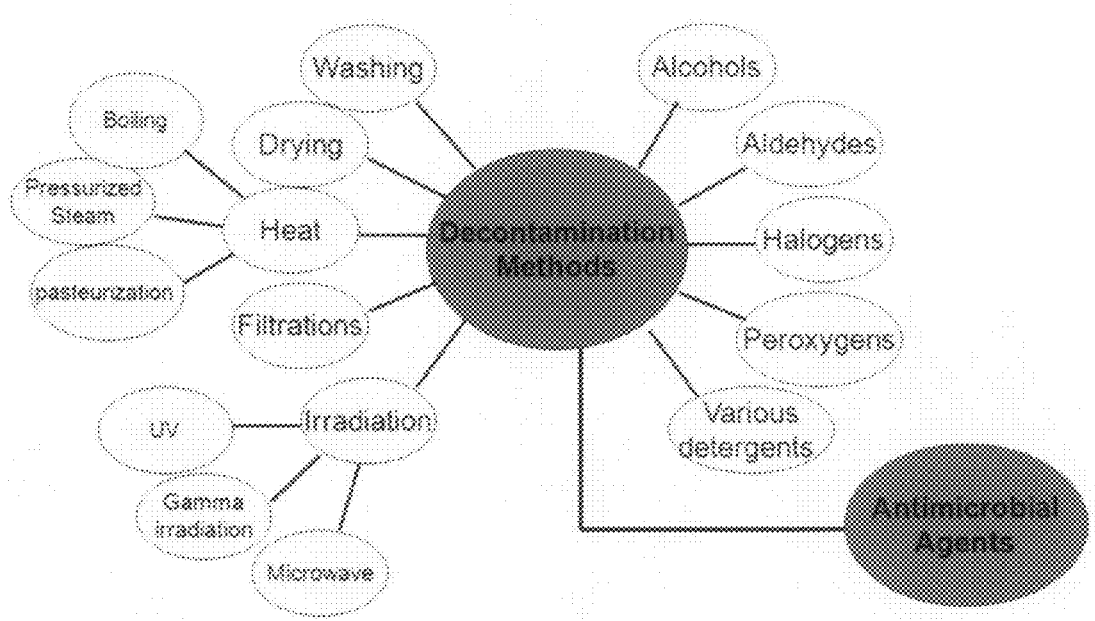

[00153] After recognizing microbiological contamination events, various techniques to control microbial growth (physical and chemical) have been developed and used, such as washing, heat (boiling, pasteurization, pressurized steam, etc), filtrations, irradiation (ultraviolet, gamma radiation, microwave, etc.), and chemicals (alcohols, aldehydes, halogens, peroxygens, various detergents, etc.) (Fig. 8). These efforts have only one-time or temporary effects. They are usually also limited in time and space. Only some of the antimicrobial agents may have long-term antimicrobial activities. Many ordinary surfaces can be adequately decontaminated with routine disinfection, but many other common surfaces and inaccessible areas can not so effectively be treated. Commonly-used disinfection techniques are incapable of eradicating reservoirs of pathogens such as methicillin-resistant *Staphylococcus aureus* (MRSA) [16]. In fact, traditional cleaning techniques – even some using alkylamines and quaternary ammonium compounds -- may do more to spread microbes than to reduce their populations. At the same time, quaternary ammonium compounds, phenols, and chlorine sanitizers are irritating to asthmatic or respiratory impaired patients and staff. Thus, there is an enormous market demand in the world for antimicrobial materials that can be used to protect the public health with surface decontamination ability and long durability.

[00154] To be used for surface decontamination, the antimicrobial material must meet criteria such as performance, wide spectrum on pathogens, pre-applied on various kinds of surfaces, safe to human and animals, blendable with various coating materials, long durability and stability versus environments, low cost, heat resistance, environmental friendly, etc.

[00155] To date, the research and development of antimicrobial materials for sanitation (hygiene) has been carried out mostly in Japan, United States, Western Europe and China. Commercial products such as antibacterial fibers, socks, underwear, sports wear, and refrigerators have been promoted [17-26]. However, most of the antimicrobial products developed so far are organic and/or liquid. They can be tailored to be very effective for certain bacteria species. A key example is triclosan (2, 4, 4'-trichloro-2'-hydroxydiphenyl ether) that has been incorporated into a wide variety of materials, often under the name Microban [27, 28]. However, organic antimicrobial agents have the disadvantages of high cost, short lifetime, low thermal resistance, low chemical stability, and lack of the ability to fight a broad range of bacterial species, even inducing toxic decomposition at certain environmental conditions [29-31]. Additionally, resistance to triclosan has been reported and there are concerns that resistant bacteria are more prone to developing antibiotic resistance [28, 32].

[00156] It has been found that some metallic ions, such as silver, copper, zinc, nickel, and manganese exhibit strong antimicrobial activities. Among these, silver and copper are the most effective elements [31-33]. For example, the concentrations of copper required for water disinfection is only 200-400 µg/L, while silver is 40-90 µg/L [34]. Other metal ions such as arsenic, mercury, and cadmium also have strong antimicrobial properties but are biologically very toxic and are more difficult to deploy safely. Metallic ions on the surface of an appliance or utensil that may come in contact with bacteria and other microbes disrupt the normal metabolism and replication functions of these cells. This typically results in microbial death.

[00157] Although some inorganic antimicrobial materials have been studied, most of them were provided in nano-sized metallic particles of silver (10-50 nm) or silver-loaded zeolite and titanium oxide ($TiO_2$) [35-45]. Nano-sized silver particles usually consist of a metallic silver core which is surrounded by silver oxide. This affects the release of silver ions. Further, a higher additive amount in the target products would lead to excessive concentration of silver and result in increased cost. Titanium oxide has a high photocatalytic activity and excellent durability. It has already been used as an antibacterial agent. However, titanium oxide can only be excited by ultraviolet light, which has limited its effectiveness under actual conditions. Zeolites incorporating silver, copper or zinc are expensive because of material costs and complex manufacturing processes.

[00158] Companies such as Sinanen Zeomic Co., Ltd (Japan), Wipak and Winpak (Finland), AgION Technologies (USA), Eldon James Corp. (USA), TOTO (Japan), Ciba Specialty Chemicals (Switzerland), Nano-Silver (Korea), Nanotech (UK), Biocera Co., Ltd. (South Korea), Microban International, Ltd (USA), Morton Grove Pharmaceuticals, Inc. (USA), Globe Machine Co. (USA), and Troy Corporation (USA) are the current suppliers of antimicrobial products [46-52].

[00159] Copper may be a better antimicrobial material than silver. Copper has both antibacterial and antifungal properties. Silver is only effective for antibacterial uses [31]. Silver has been extensively investigated for commercial applications because silver is effective at lower concentrations [16, 53]. The major issues associated with silver antibacterial materials are as follows: (1) silver is much more toxic; (2) silver is more expensive; and (3) nano-sized silver particles develop an oxide coating that retards the release of silver ions. To overcome these obstacles, a higher amount of silver in the target products is required, which leads to excessive toxicity and cost. Also, silver-loaded zeolite is an expensive material because of the complexity of manufacturing, where the exchangeable position of metallic ions in zeolite is the structural pores (holes, 0.4 nm in diameter) which are too large to hold the exchangeable ions (ionic radius of silver is only 0.113 nm). Silver also has a stability problem which affects the color and durability of the product [31, 54]. The biological activity of silver is temperature sensitive and has been shown to be negligible at temperature above 75°C [55, 56].

[00160] Thus, metallic ions of copper possess excellent potentials and priority for the development of antimicrobial materials due to its technological and economic advantages.

1.2. Concept and Objectives of This Research

1.2.1 Applications of Metallic Copper as Antimicrobial Materials

[00161] Copper has broad uses in various instruments and products, such as electrical conductors, thermal exchangers, jewelry, decorating materials, bronze sculptures and coins. Antimicrobial and antifungal attributes of copper have been known for thousands of years. The recognition of copper as an effective antimicrobial has only occurred in recent decades [57, 58]. The antimicrobial uses of copper have recently been expanded to water purification, algaecide, fungicides, pesticides, antimicrobial medicines, oral hygiene products, hygienic medical devices, antiseptics, antifouling agent, and other useful applications [59-60]. In general, the developed applications of copper related to its antibacterial properties can be classified into three types, based on its presence in the products. The first type is chemical compounds of copper such as copper sulfate ($CuSO_4 \cdot 5H_2O$) for fungal and algae control. This type of product has been facing severe durability challenge due to complete dissolution of copper compounds in water. The second type is copper complexes such as chelated copper or organic compounds (e.g., cetylpyridinium cation, acesulfame) [61-68]. This type of material is not always applicable due to sensitive processing conditions, stability of the complex, and the toxicity of some organic compounds. The third type is metallic copper. Recent studies showed that copper and copper alloys can reduce the transmission of the highly toxic *E. coli* O157:H7, *Listeria monocytogenes*, *Salmonella enterica*, *Campylobacter jejuni*, as well as serious hospital-acquired MRSA [58, 69-73]. Furthermore, copper could even help to prevent bird flu as well as other flu infections [74]. However, such copper-based materials are effective for surface decontamination only when the copper content is over 65%, since the shortage of non-ionized chemical bond of copper in the alloys [69]. Surface oxidation does remain an issue in rates of copper release.

[00162] In recent years, copper nanoparticles have been tried for antimicrobial purposes. Unfortunately, the surface oxidation and environmental lixiviation are impeding their use [75]. In addition, according to a recent investigation on bactericidal effect of silver nanoparticles, the bactericidal properties of the nanoparticles are size dependent, with smaller particles (1-10 nm) resulting in better antibacterial efficiency [76]. This feature may also apply to the application of copper nanoparticles.

[00163] Although several metallic ions have extensive applications to antimicrobial purposes and a number of antimicrobial mechanisms of metals have been developed, the detailed interaction mechanisms of microbe-metal are still unclear. In general, the antimicrobial mechanism of copper is believed to result from its strong ionic nature. Once the metallic ion of copper diffuses across cell membrane of pathogenic microbes by various pathways, it inhibits the enzymatic activity by substituting native metal ions within an enzyme. This substitution would render the enzyme nonfunctional and the metabolism of microbe is disrupted [77-82]. Consequently, the replication of microbes is terminated. Several other mechanisms have also been proposed based on ionic action of copper [83], and the antimicrobial mechanisms were considered to be inter-changeable against specific classes of microorganisms [77]. Copper may also affect the redox reaction on the exterior surface of microbial cell.

[00164] Therefore, the antimicrobial affectivity of copper depends on the chemical activity or ionized grade of copper in the carrier materials.

1.2.2 Host Material of Copper Ions

[00165] To be considered as a host (carrier) of ionic copper for antimicrobial applications, the material must be able to satisfy all the requirements of antimicrobial products, appropriately hold and release ionic copper in order to obtain the best antimicrobial efficiency, and inexpensive for manufacturers and customers.

[00166] Vermiculite has the potential to be an ideal host for copper ions [84]. Vermiculite is a naturally occurring magnesium-based layer-structured mineral. In the past decades, vermiculite has been extensively used as fillers of fireproof materials, plastics, paints, and fertilizers. Vermiculite is also an excellent absorber of heavy metal ions and radioactive atoms [85]. In addition, exfoliated vermiculite is used as filler in lightweight concrete because of its low density. All of these applications have been deeded safe to human contact. Moreover, vermiculite is used as an environmental remediation material.

Figure 9:
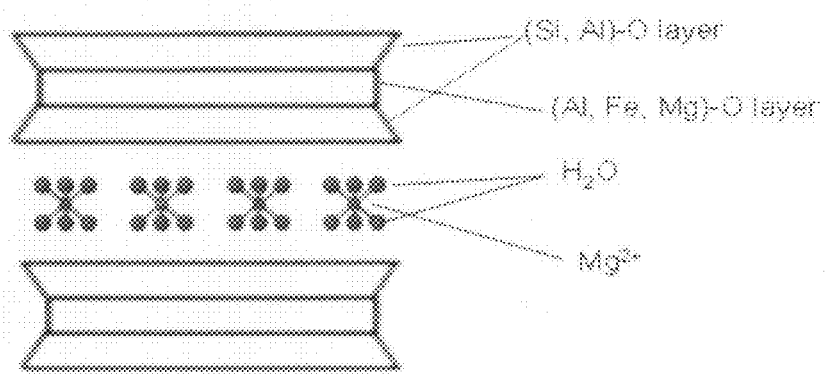

[00167] The chemical formula for Vermiculite is [86]:

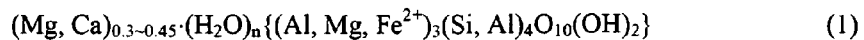

$$(Mg, Ca)_{0.3-0.45} \cdot (H_2O)_n \{(Al, Mg, Fe^{2+})_3(Si, Al)_4O_{10}(OH)_2\} \quad (1)$$

where the interlayer regions of vermiculite are negatively charged and mainly filled with exchangeable magnesium ions (Fig. 9). Since copper has equivalent charge and an atomic radius similar to magnesium [the ionic radius of magnesium ($Mg^{2+}$) is 0.075 nm, copper ($Cu^{2+}$) is 0.072 nm], the magnesium atoms in the interlayer regions of vermiculite can be easily replaced by copper via a cation exchange process. The copper vermiculite consequently has structural and chemical stability which is similar to naturally occurring magnesium vermiculite.

[00168] The principal advantage of a vermiculite carrier is that the structure is stable under industrial and environmental conditions. Vermiculite can provide a relatively stable storage, and consistent and effective delivery vehicle for antimicrobial agents. Copper ions implanted in the interlayer of vermiculite can be slowly released via cation exchange and delivery to the surface by diffusion.

[00169] The cation exchange capacity (CEC) of typical vermiculite is between 100 mmol/100g and 150 mmol/100g [85, 87]. That is, vermiculite can contain copper as high as 6.35~9.53% by weight. This amount of copper provides the potential to make vermiculite a very effective and durable antimicrobial material.

Figure 10:
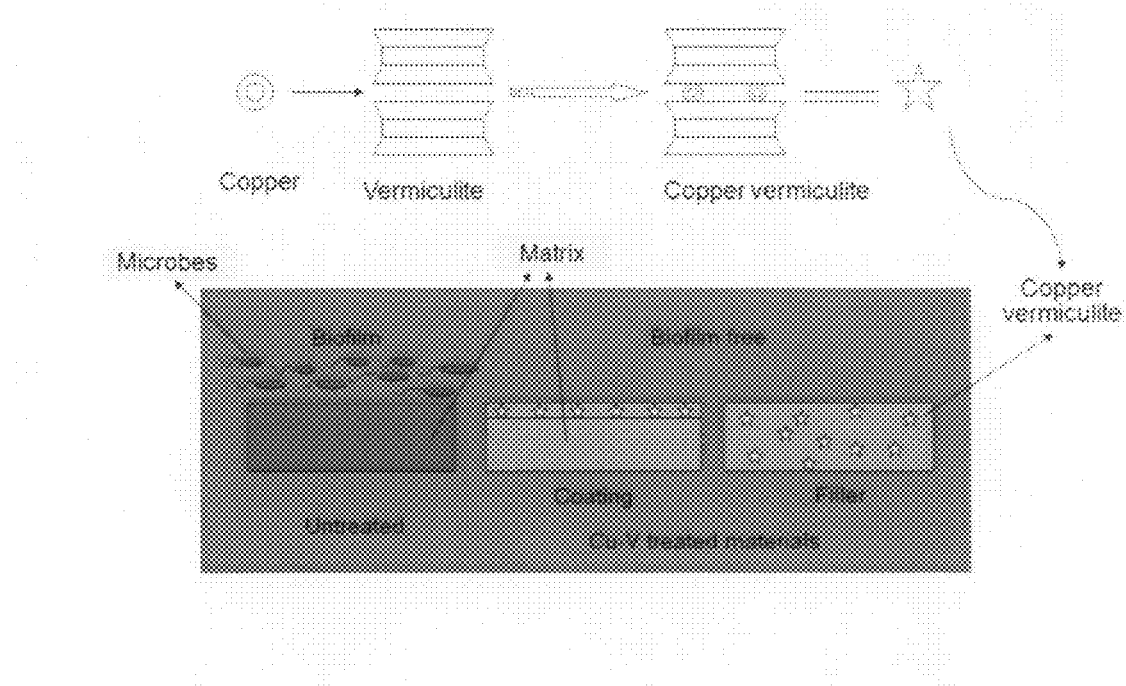

[00170] Antimicrobial copper vermiculite is expected to be applied on surfaces, where humans will have contact. These materials should resist microbial corrosion, restrict growth of pathogenic biofilms and prevent the transfer of germs. Once the copper vermiculite is used, the surface of the products is expected to be biofilm-free (Fig. 10). Since antimicrobial protection of the products containing copper vermiculite is built-in, it will not wash off or wear away, but provides continuous antimicrobial protection with self-decontamination for the life of many different types of surfaces and products. Therefore, the potential market for the material is enormous since many things involved with daily life could benefit from antibacterial properties.

1.2.3 Research Objectives

[00171] The objectives of the current research are to synthesize and characterize the proposed copper vermiculite, including micron-sized copper vermiculite (MCV) and exfoliated copper vermiculite (MECV); assess the antimicrobial effects of the two types of copper vermiculite against the most common but seriously pathogenic bacteria; and evaluate the chemical stability of copper vermiculite.

2 Synthesis and Characteristics of Copper Vermiculite

2.1 Preparation of Vermiculite Particles

2.1.1 Original Vermiculite Samples

[00172] Vermiculite is a naturally occurring magnesium-based layer-structured mineral. It is extensively distributed in the United States and worldwide. In the United States, the major vermiculite mining operations are located in South Carolina and Virginia. Annually, over 100 thousand tons of vermiculite was produced, and over 150 thousand tons of vermiculite was consumed [88]. Other major vermiculite-producing countries include South Africa, Australia, Brazil, China, Egypt, India Japan, Kenya, Russia, and Zimbabwe.

[00173] Most vermiculite is consumed in thermally exfoliated form [88]. Within the interlayer regions of vermiculite, water molecules will transform into steam when rapidly heated to high temperature (around 900°C or higher), causing the dramatic increase of volume of vermiculite particles (expansion, usually called exfoliation). Exfoliated vermiculite has very unique properties, such as high porosity, specific surface area, high aspect ratio of laminates, low density, and high cation exchange capacity, it has been extensively used in various industrial applications.

[00174] The crude vermiculite used in this study is a commercial vermiculite product produced by Virginia Vermiculite LLC. The ore was mined from Louisa, VA, and wet-processed to separate the flake-shaped vermiculite particles from the gangue (rock and clay) material. The vermiculite concentrate was then dried and sized into several different grades. Concentrates were also processed into exfoliated products. The chemical composition of vermiculite may be vary due to the weathering process from original minerals and ion-exchange. The typical range of the chemical compositions of Virginia vermiculite is (wt%): $SiO_2$ 36-44, $Al_2O_3$ 10-15, $Fe_2O_3$ 9-13, MgO 17-22, CaO 0.5-3, $Na_2O$ 0.1-0.3, $K_2O$ 3-6, $TiO_2$ 1-3, $P_2O_5$ 0.1-0.2, MnO 0.1-0.2, $Cr_2O_3$ 0.1-0.3, and LOI 7-13 (Data from the product specification sheet provide by the Virginia Vermiculite LLC).

[00175] The vermiculite concentrates used in this study include two commercial products from Virginia Vermiculite LLC, Grade No.5 Vermiculite Concentrate (VV-5) and Milled No.7 (VV-7). The micron-sized vermiculite powder was jet-milled from VV-5 (VV-CCE).

[00176] The VV-5 maintains coarse particles (sheet platelet), is medium brown to black, has a bulk density of 800-1120 kg/m$^3$ (50-70 lb/ft$^3$), and a specific gravity of 2.5-2.8. The Cation exchange capacity is 50-100 m.e./100g, pH (in distilled water) 6.0-8.0, expansion temperature 650-980°C, and melting point 1200-1350°C (Data from the product specification sheet provided by the Virginia Vermiculite LLC, 2006). The particle size shows as Table 1.

Table 1. Particle Size Distributions of VV-5 and VV-7

| Sample | Unit | Particle Size Distribution (wt %) | | | | |
|---|---|---|---|---|---|---|
| VV-5 | US mesh | +20 | 20-30 | 30-50 | 50-100 | -100 |
|  | mm | +0.84 | 0.60-0.84 | 0.30-0.60 | 0.15-0.30 | -0.15 |
|  | wt% | 0 | 0 | 16 | 53 | 31 |
| VV-7 | US mesh | +40 | 40-70 | 70-100 | 100-200 | -200 |
|  | mm | +0.42 | 0.21-0.42 | 0.15-0.21 | 0.07-0.15 | -0.07 |
|  | wt% | 2 | 17 | 12 | 42 | 27 |

(Data from the product specification sheets provided by the Virginia Vermiculite LLC, 2006).

[00177] The VV-7 vermiculite is an exfoliated powder product produced by thermal exfoliation from vermiculite concentrate. It is also a tan, sheet platelet with a bulk density of 96-160 kg/m$^3$ (6-10 lb/ft$^3$), total moisture < 2.5% (free and intrinsic), aspect ratio up to 20,000, and cation exchange capacity is 50-150 mmol/100g (Data from the product specification sheet provided by the Virginia Vermiculite LLC, 2006).

Figure 11:
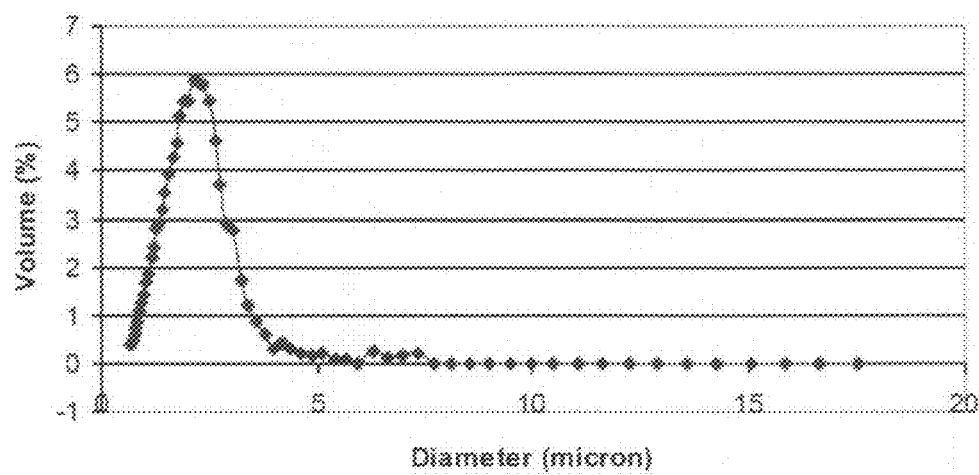

[00178] The micron-sized vermiculite (VV-CCE) was prepared with VV-5 particles, and jet milled by the CCE Technologies, Inc. MN. The jet-milled vermiculite powder shows a narrow particle size distribution, which is at the size level of clays. The particle size based on laser diffraction analysis is: maximum 7.34 micron, mean 2.058 microns, and 99% of the particles are less than 5.13 microns. (Fig. 11), Instrument: Beckman Coulter MULTI3; Electrolyte: ISOTON II; Dispersant: TX100/US; Total count: 50,000). The features of vermiculite particles are shown in Fig. 12.

Figure 13:
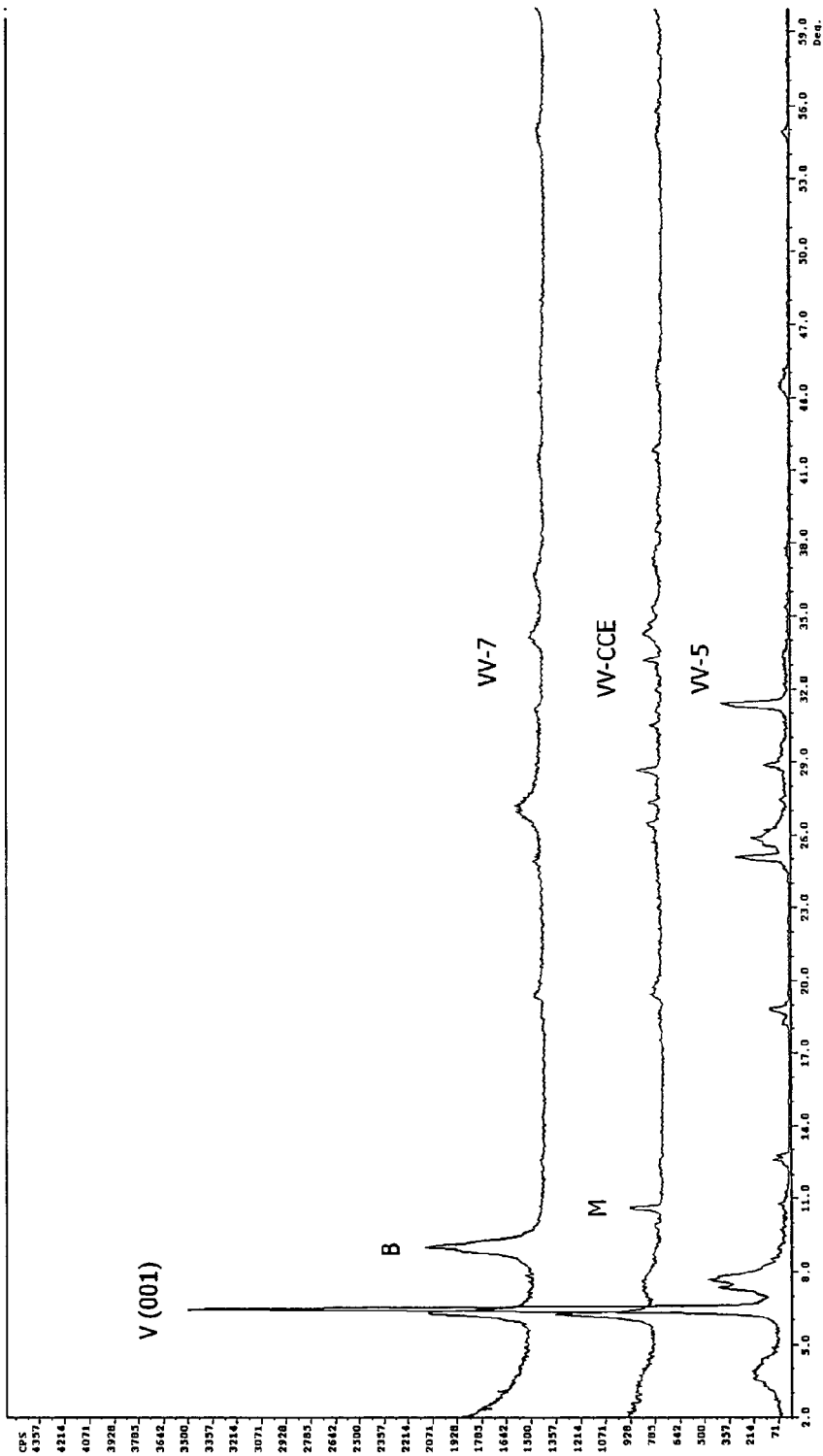
Figure 14:
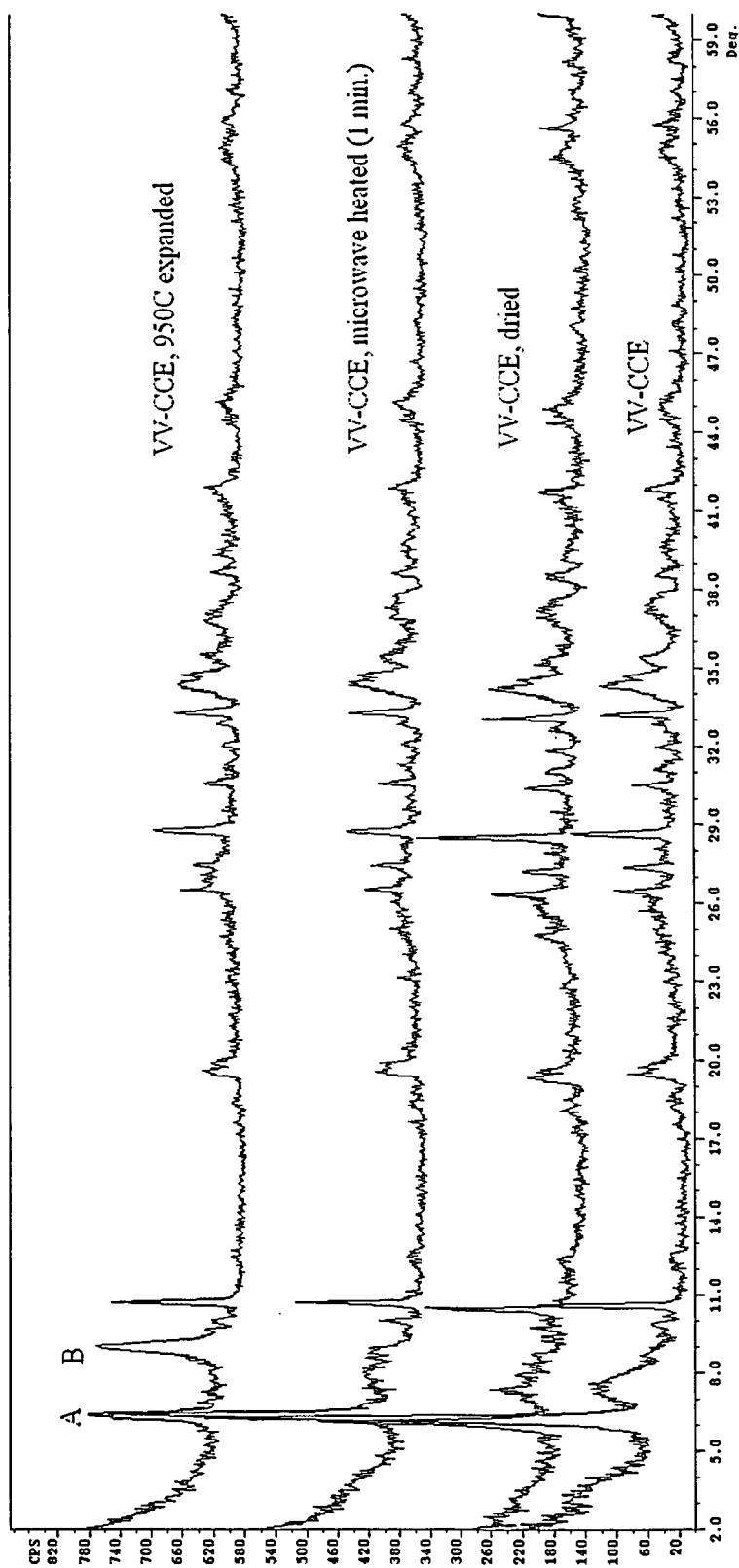
Figure 15:
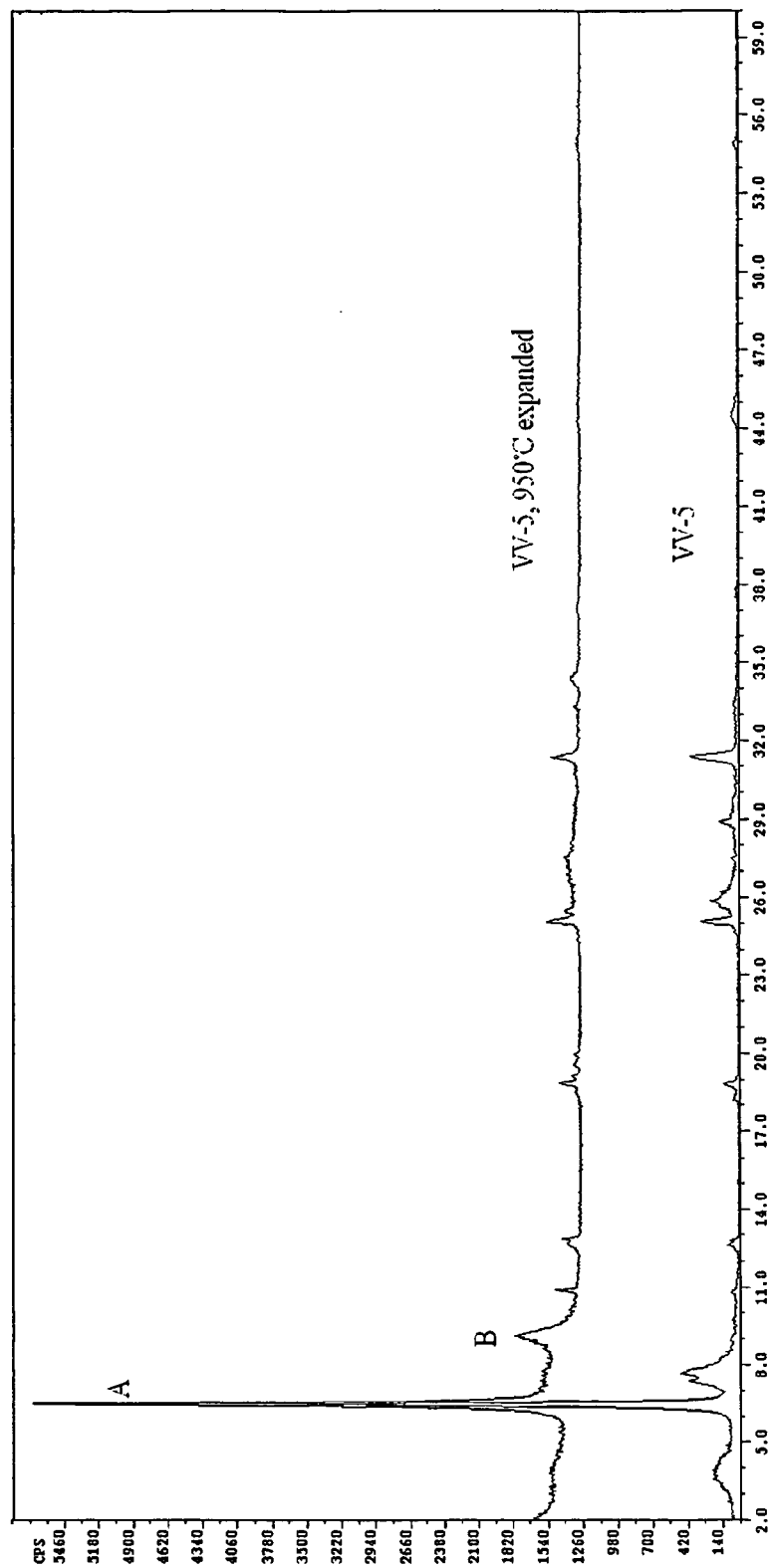

[00179] The X-ray patterns of vermiculite are very clean for the VV-5 and VV-7 powders and show the high level of purity (Fig. 13). VV-CCE powder contained a little magnesiohornblende. The $d_{001}$ of VV-5, VV-CCE, and VV-7 were 1.370, 1.413, and 1.404 nm, respectively. Although VV-7 has a peak with high intensity around $2\theta = 9.000$ ($d_{001}=0.9818$ nm), this peak results from the structural collapse of original (001) planes due to exfoliation process, rather than impurities from other minerals. This was verified by calcining VV-CCE and VV-5 at 950°C (Fig. 14 and 15).

2.1.2 Cation Exchange Capacities of Vermiculite

[00180] The chemical formula of typical vermiculite is:

$$(Mg, Ca)_{0.3 \sim 0.45} \cdot (H_2O)_n \{(Al, Mg, Fe^{2+})_3(Si, Al)_4O_{10}(OH)_2\} \qquad (2)$$

[00181] Where, $(Mg, Ca)_{0.3 \sim 0.45}$ represent the exchangeable interlayer cations. The simplified ideal cation exchange reaction would be $$B + A\text{-vermiculite} \rule{1cm}{0.4pt} A + B\text{-vermiculite} \qquad (3)$$

[00182] Where A represents exchangeable interlayer cations in vermiculite, and B is cation substitutes of A in vermiculite. In general, A in natural vermiculite mostly is $Mg^{2+}$, which could be partially replaced by $Ca^{2+}$, $Fe^{2+}$, etc. Generally, the equilibrium constant of the cation exchange reaction, $k$, can be described as $$k = \frac{[A^{2+}][B-vermiculite]}{[B^{2+}][A-vermiculite]} \qquad (4)$$

[00183] Here, [A-vermiculite] and [B-vermiculite] are concentrations of vermiculite before and after the reaction, respectively. [$B^{2+}$] is concentration of B atom in the solution before reaction; [$A^{2+}$] represents the concentration of A atom in the solution after reaction. However, B could also be replaced with 1+ ions, such as $NH^{4+}$.

[00184] The Cation Exchange Capacity (CEC) of vermiculite can be expressed two ways: 1) the number of cation adsorption sites per unit weight of vermiculite or, 2) the sum total of exchangeable cations that vermiculite can adsorb. The former can be theoretically calculated. The latter can be experimentally measured, which adopted in this study.

(1) Methodology

[00185] The CECs in this research are measured by ammonium acetate. This method is widely adopted by most soil testing laboratories [89]. After saturating exchangeable cation sites with ammonium cations, the ammonium-exchanged vermiculite is dispersed in sodium hydroxide solution to release the ammonium as dissolved ammonia gas. The signals of ammonia dissolved in solution can be detected by a specific-ion electrode. The ammonium concentration can be measured by the comparison of the signals from the unknown solution with a series of standard solutions. The cation exchange capacity is correspondingly calculated. [90]

(2) Instrumentation

[00186] The ammonia ion-selective electrode used in this measurement is a product of the Orion Research Incorporation (model 95-12) with a new ammonia membrane cap. The electrode was connected to an Orion electrode meter. Ammonia standards were made by diluting freshly prepared 0.1M ammonium chloride. All centrifugation was performed on an IECCentra-HN centrifuge (Produced by the International Equipment Company).

(3) Procedure of Sample Preparation

Figure 16:
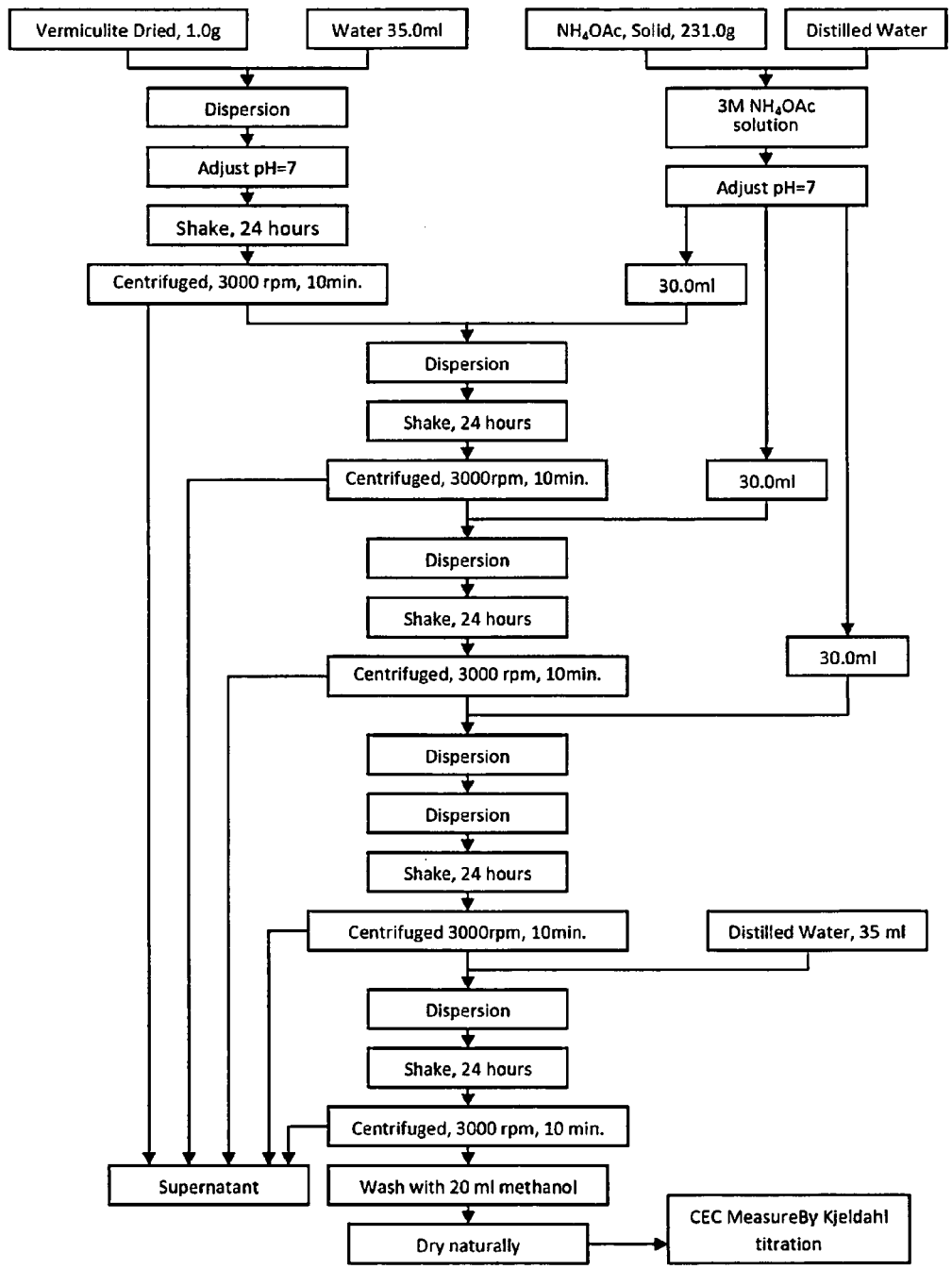

Fig. 16 shows the procedure of sampling for CEC. All of the sampling and measurements were performed at room temperature and triplicate.

(4) Determination of CEC

Figure 17:
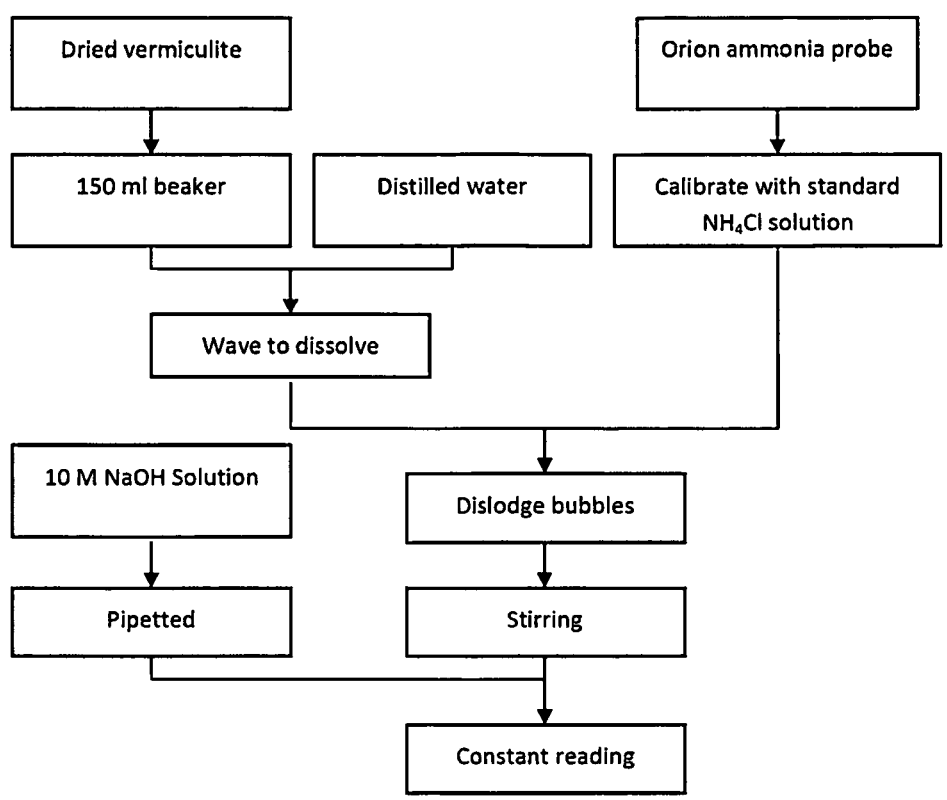
Figure 18:
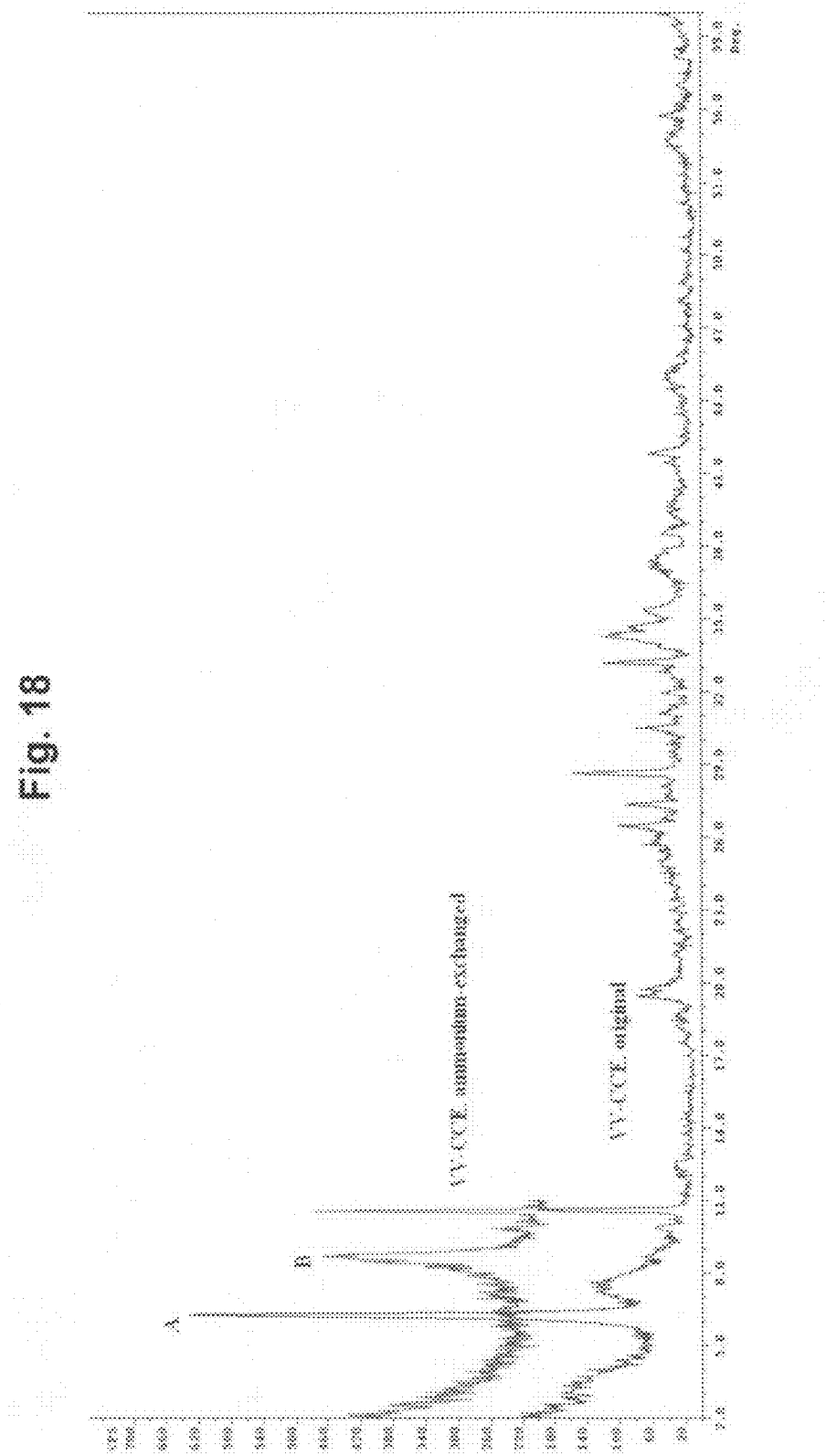

[00187] Referred to the Kjeldahl Titration, the procedure of measurement of CEC was implemented as show in Fig. 17 [90]. The determination of using 100 mg dried vermiculite samples was based on that it would be able to keep the final ammonia concentrations between $10^{-4}$ and $10^{-1}$ M, which is the range covered by the standard solutions.

(5) Results of CEC Measurement

[00188] The CEC measured by the concentrations of ammonia shows as Table 2. The cation exchange capacity (CEC) of typical vermiculite is between 100 mmol/100g and 150 mmol/100g [91-92]. These measured values are lower than that provided by Virginia Vermiculite LLC, especially for VV-5. This may be caused by the different procedures that measure CEC, since CEC value is very sensitive to measurement conditions.

Table 2. Cation Exchange Capacities of Virginia Vermiculite

| Sample No | Cation Exchange Capacity (CEC) (mmol/100g) | |
|---|---|---|
| | Measured in this study | Virginia Vermiculite LLC provided |
| VV-5 | 8.79 | 50~100 |
| VV-7 | 67.19 | 50~150 |
| VV-CCE | 42.24 | |

[00189] The cation exchange reaction by ammonia led to a phase transformation of the vermiculite. After the cation exchange with ammonium, the original layer structures of vermiculite were collapsed. The interlayer spacing of (001) planes of vermiculite reduced from 1.370-1.413 nm to 9.958-10.936 nm. The intensities of (001) planes were also significantly decreased (Fig.s 18, 19, 20).

[00190] To confirm if the washing process using methanol impact the structure and interlayer spacing, VV-5 and VV-7 particles were soaked in methanol concentrate (93.8%) for 48 hours, then the samples were dried and powder XRD were performed. The results show that methanol concentrate neither led to the collapses of interlayer structure nor made structure change of vermiculite (Fig. 21).

2.2 Synthesis of Copper Vermiculite

[00191] The synthesis of copper vermiculite can be chemically expressed by below reaction:

$$(Mg, Ca)_{0.3\sim0.45}\cdot(H_2O)_n\{(Al, Mg, Fe^{2+})_3(Si, Al)_4O_{10}(OH)_2\} + 0.3\sim0.45Cu^{2+} \text{-----}$$
$$(Cu^{2+})_{0.3\sim0.45}\cdot(H_2O)_n\{(Al, Mg, Fe^{2+})_3(Si, Al)_4O_{10}(OH)_2\} + 0.3\sim0.45\ (Mg^{2+}, Ca^{2+})$$

Where, $(Mg, Ca)_{0.3\sim0.45}$ represent the exchangeable interlayer cations in the interlayer regions of vermiculite before cation exchange reaction, and $(Cu^{2+})_{0.3\sim0.45}$ represent the exchangeable interlayer cations in the interlayer regions of vermiculite after the cation exchange reaction. The simplified ideal cation exchange reaction would be $$Cu^{2+} + Mg^{2+}\text{-vermiculite} \text{--------} Mg^{2+} + Cu^{2+}\text{-vermiculite} \tag{5}$$

[00192] According to previous optimizing experiments, copper vermiculite was prepared by the following steps:

(1) Vermiculite powder (VV-CCE, or VV-7) was dried in oven at 105°C for 24 hours.

(2) Preparation of CuCl$_2$ solution: CuCl$_2\cdot$2H$_2$O (molecular mass is 170.49) was mixed with distilled water to prepare a solution of 0.12 M concentration.

(3) Weighed 2.000g dried vermiculite powder and dispersed into 80.0 ml of CuCl$_2\cdot$2H$_2$O solution.

(4) Reaction was carried out by heating the suspension to 80°C and mixing the suspension with magnetic stirrer continuously for 3 hours.

(5) The suspension after reaction was filtered. The filter cake was washed with 50ml distilled water and the washing was repeated for 5 times.

(6) The filtered solutions were diluted into 500 ml solutions, and the final product was dried at 105°C for 24 hours.

[00193] The previously prepared vermiculite samples, VV-CCE and VV-7, were used to prepare copper vermiculite (MCV) and exfoliated copper vermiculite (MECV), respectively.

2.3 Characterization of Copper Vermiculite

2.3.1 Chemical Composition and Copper Content of Copper Vermiculite

[00194] The chemical composition and copper concentration of dried copper vermiculite were analyzed by Inductively Coupled Plasma spectroscopy (ICP), through the fusion method with lithium metaborate. The typical chemical composition of copper vermiculite (MCV) and exfoliated copper vermiculite (MECV) are shown in Table 3. Correspondingly, the copper concentrations in MCV and MECV were 2.55% and 2.34 wt%.

Table 3. Chemical Composition of Copper Vermiculite (wt%)

|      | $Al_2O_3$ | CuO  | $TiO_2$ | $Na_2O$ | MgO   | $SiO_2$ | $K_2O$ | CaO  | $Cr_2O$ | MnO  | $Fe_2O_3$ | LOI  |
|------|-----------|------|---------|---------|-------|---------|--------|------|---------|------|-----------|------|
| MCV  | 12.66     | 3.62 | 1.18    | 0.66    | 18.20 | 35.45   | 3.07   | 4.10 | 0.26    | 0.13 | 11.36     | 9.32 |
| MECV | 15.09     | 3.42 | 1.51    | 0.31    | 20.81 | 35.67   | 3.73   | 1.70 | 0.34    | 0.10 | 11.54     | 5.78 |

[00195] According to the theoretical loading capacity of copper in vermiculite, and the experimental resultes of cation exchange capacity, there is still a potential to increase the copper content in vermiculite by selecting crude vermiculite, purifying structure of vermiculite, and improving process of cation exchange, etc.

2.3.2 Microtopography of Copper Vermiculite

[00196] According to investigation via field emission scanning electronic microscopy (FESEM), the surface of the silicate sheet of vermiculite is smooth and clean. Fig. 22 is SEM image of the VV-CCE vermiculite. Fig. 23 shows the topography of MCV, which copper-exchanged vermiculite from VV-CCE. The figure clearly shows the lack of visible particles of copper metal or copper compounds at the nanometer scale on either the lamellas surface or the edge of the copper vermiculite. This demonstrated that copper atoms are homogenously dispersed in the vermiculite structure.

[00197] The SEM images of exfoliated copper vermiculite and exfoliated vermiculite are shown as Fig. 24 and Fig. 25. They also show no aggregated copper metal particles on the surfaces or edges of aluminum silicate sheets.

[00198] Since copper vermiculite (MCV) and exfoliated copper vermiculite (MECV) were washed thoroughly after cation exchange reaction, the copper atoms hosted in vermiculite are insolvable. This also verifies that the copper atoms hosted in vermiculite were stably bonded by the aluminum silicate sheets of vermiculite.

2.3.3 Layer Structure of Copper Vermiculite

Figure 27:
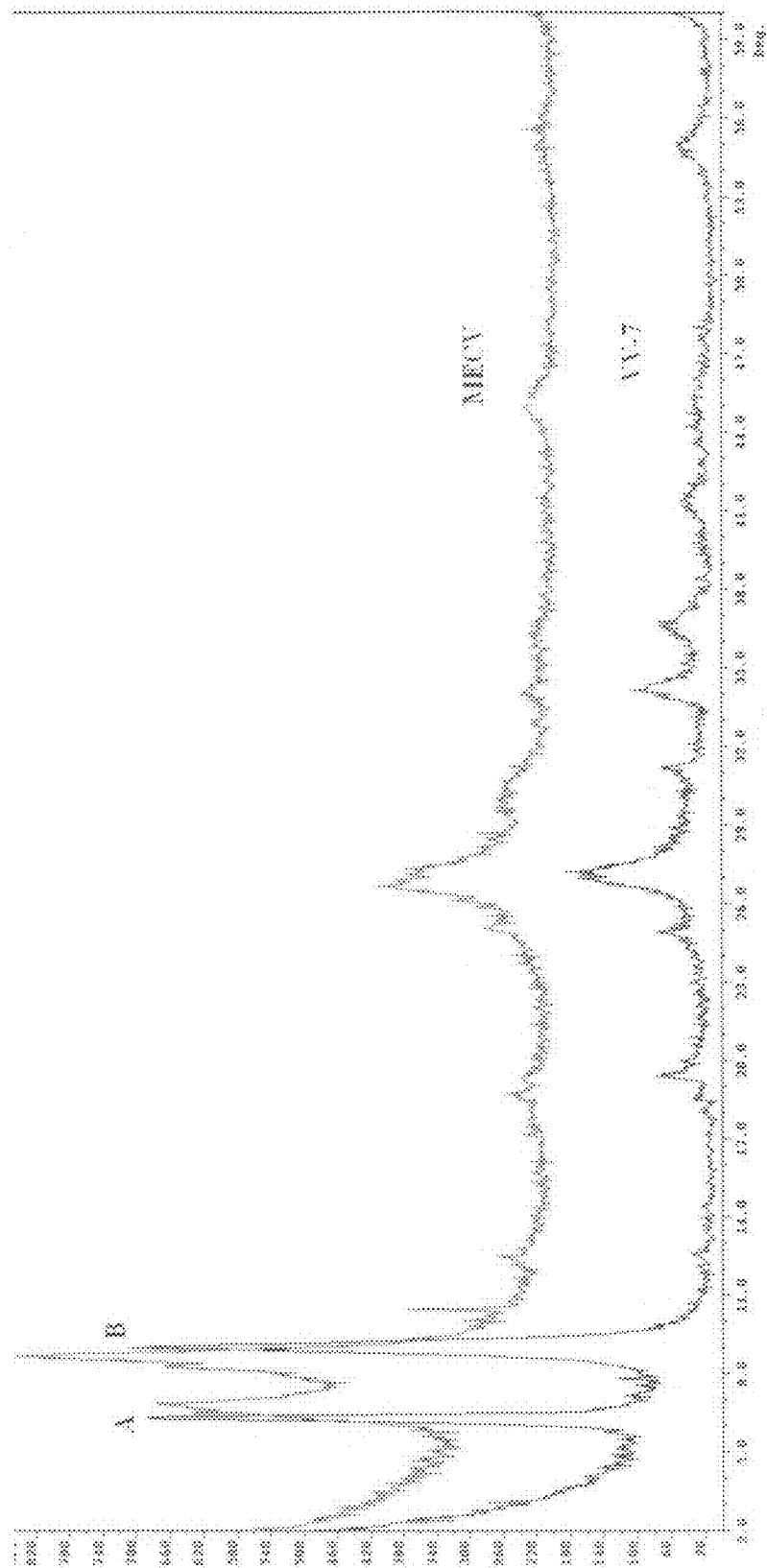

[00199] Fig. 26 is a comparison of XRD patterns of copper vermiculite (MCV) and jet-milled vermiculite (VV-CCE), which are with and without copper. The structure of the vermiculite did not change significantly after implantation of the copper ions into the interlayer regions, even though this was a phase transformation from Mg-vermiculite into Cu-vermiculite. The peak intensity of (001) planes did however a little decrease after the exchange reaction. This indicates that the copper vermiculite inherited the structure of magnesium vermiculite. Copper ions have appropriately substituted within the interlayer cation sites for magnesium. Fig. 27 shows the XRD patterns of MECV and VV-7, which are exfoliated vermiculite after and before copper implantation. The structure of the exfoliated copper vermiculite has similar characteristics to the non-exfoliated vermiculite (Fig. 26), except the intensity of the original (001) is now reduced. This may caused by the drying process followed cation exchange reaction, which result in partial dehydration of interlayer regions of vermiculite.

Figure 28:
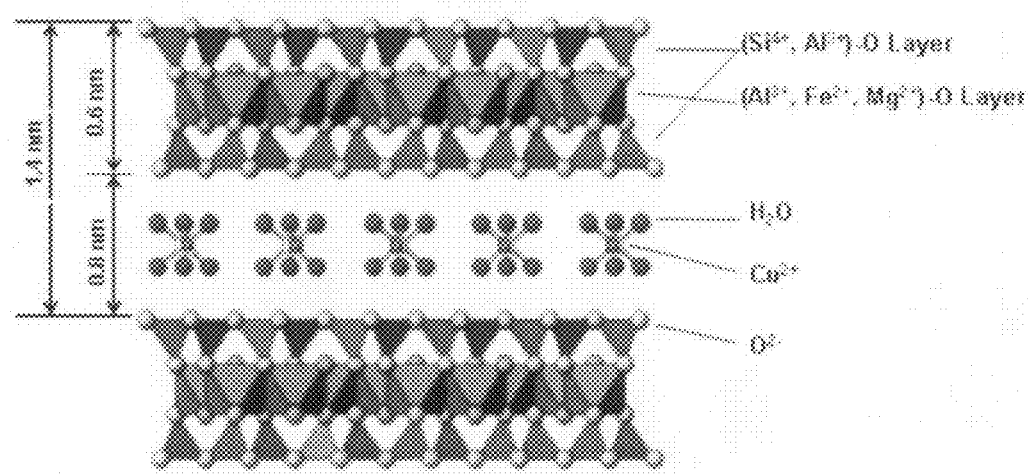

[00200] The structure model of copper vermiculite can be correspondingly established and is shown schematically in Fig. 28. Copper vermiculite maintains the structure of magnesium vermiculite. In the structure, the blue octahedral represent the Al-O octahedral layer, the red and brown triangles represent Si-O tetrahedral layers, which are comprised of 2:1 silicate sheets.

Additionally, the blue triangles represent that silicon ions were substituted by aluminum ions in the Si-O tetrahedrons. In the interlayer region, the hydrated copper cations were associated with water molecules at interlayer positions (Usually, the copper atom in the interlayer sites have six coordinates of water molecules as an octahedral coordination). The water molecules also lay between the layers of exchangeable copper ions and silicate layers, and consequently form two layers of water molecules. According to theoretical calculation, the thickness of silicate layer is 0.6 nm. From the results of XRD analysis, the interlayer spacing of copper vermiculite is kept at 1.4 nm. Thus the thickness of interlayer region is 0.8 nm.

2.4 Summary

[00201] Vermiculite is a naturally occurring magnesium-based layer-structured mineral. It is extensively distributed in the United States and worldwide. Most vermiculite is consumed in thermally exfoliated form.

[00202] In this study, micron-sized vermiculite was prepared by jet-milling. The jet-milled vermiculite powder has a narrow particle size distribution, which has the maximum particle size in 7.34 micron, and mean particle size in 2.058 micron.

[00203] The cation exchange capacities (CECs) of vermiculite were measured by ammonium acetate. The result shows that the Virginia vermiculite samples used has a lower CEC than that expected. The cation exchange reaction by ammonium led to a phase transformation of the vermiculite. After the cation exchange with ammonium, the original layer structures of vermiculite were collapsed. The interlayer spacing of (001) planes of vermiculite reduced from 1.370-1.413 nm to 9.958-10.936 nm. The intensity of (001) planes were also decreased.

[00204] Two types of copper vermiculite materials, micron-sized copper vermiculite (MCV) and exfoliated copper vermiculite (MECV), were synthesized by using jet-milled and exfoliated Virginia vermiculite, through a cation exchange process at 80°C. The characteristics of copper vermiculite were investigated.

[00205] The resulting atomic content of copper (as $Cu^{2+}$) was 2.55 wt% and 2.34 wt% in copper vermiculite, and exfoliated copper vermiculite, respectively. Copper vermiculite inherited the structure of magnesium vermiculite without aggregates of copper. Based on field emission scanning electron microscopy, the copper atoms were homogeneously dispersed in the vermiculite structure. The interlayer spacing of copper vermiculite is kept at 1.4 nm, and the thickness of interlayer region is 0.8 nm.

3 Antimicrobial Activities of Copper Vermiculite

3.1 Test Bacteria

[00206] The test microorganisms for this study were selected from the most common but pathogenic species from both gram-negative bacteria and gram-positive bacteria. They included three species: *Escherichia coli (E. coli)*, *Staphylococcus aureus (S. aureus)*, and *Klebsiella pneumoniae (K. pneumoniae)*.

[00207] *E. coli*, a gram-negative bacterium, is the principal food- and water-borne strain that can cause severe illness and death. This rod-shaped bacterium is responsible primarily for three types of infections in humans: urinary tract infections, neonatal meningitis, and intestinal diseases [93-94]. Some strains can cause severe food poisoning and life-threatening diarrhea. The toxic strains of this microbe are responsible for about half of all cases of traveler's diarrhea. Recently there has been an increase in disease since publicized outbreaks of strain 0157:H7 [95]. The optimal reproduction condition for *E. coli* is at 37°C of environment temperature, which is very close to the average temperature of the human body.

[00208] *E. coli* grows well on the usual laboratory media in both the presence and absence of oxygen. In both the natural environment and the laboratory, *E. coli* is the most extensively studied and most well-understood bacterium. Since it can respond to environmental signals (such as chemicals, pH, and temperature) in various ways, and easy to be detected and cultured, it has been used worldwide as the principal indicator of fecal contamination [94].

[00209] *S. aureus* is a gram-positive spherical bacterium, which is always considered as a pathogen of humans, causes various illnesses ranging from minor skin infections (such as boils, furunculosis, styes, and abscesses) to fatal disease (such as pneumonia, mastitis, phlebitis, meningitis, osteomyelitis, endocarditis, toxic shock syndrome, and septicemia) [96]. It also causes food poisoning by releasing enterotoxins into food, and toxic shock syndrome by release of superantigens into the blood stream. *S. aureus* is also a major cause of deadly hospital-acquired (nosocomial) infection of surgical wounds and infections [96].

[00210] *S. aureus* is a cluster-forming bacterium with an individual cell diameter of approximately 1 micron [97]. Staphylococci are anaerobes that grow by aerobic respiration or fermentation of glucose. *S. aureus* can grow at a temperature range of 15–45°C and at NaCl concentrations as high as 15%. Most strains of *S. aureus* produce the enzyme coagulase.

[00211] *K. pneumoniae* is a rod-shaped gram-negative bacterium. It commonly affects people with bacterial pneumonia due to aspiration, and implicates in hospital-acquired urinary tract and wound infections [98]. It is also a pathogen for patients with chronic pulmonary disease, diabetes, enteric pathogenicity, nasal mucosa atrophy, and rhinoscleroma. *K. pneumoniae* is an anaerobic microorganism. It is easy to be found in soil, water and plants. Feces and contaminated instruments are the mostly significant sources of patient infection.

3.2 Methodology for Antibacterial Assessment

[00212] There are several methods that have been developed for evaluation of antimicrobial activity (antibacterial and antifungal) of antimicrobial materials based on the testing requirements and states of testing samples. Many industrial standards for antibacterial assay have been established. The most recognized standards worldwide include those designed by the ASTM International (ASTM), the American Association of Textile Chemists and Colorists (AATCC), and Japanese Industrial Standards (JIS), etc.

[00213] Generally, the antimicrobial assessment methods developed can be classified into three types: diffusion methods, dissolving methods, and surface inoculating methods, which are compared in Table 4 [99-104]. The diffusion methods assess antimicrobial effect by examining the inhibitory zone around antimicrobial materials (disc, cycle, square, streak, or rectangle) after incubation for a desired period of time. The dissolving methods evaluate antimicrobial efficiency by measuring the reduction rates (death rates) of living microbial cells in the solution containing antimicrobial materials (soluble or insoluble) after a period of time. The surface inoculating methods assess antimicrobial effect by observing the growth or measuring the colony number of microbes on the surface of test materials after inoculation and incubation for a period of time. The specific procedure could be dynamic or static. Usually, the diffusion methods are static and qualitative; the dissolving methods are dynamical and quantitative; the surface inoculating methods could be qualitative or quantitative but static and mostly applicable to antimicrobial finishes.

Table 4. Comparison of Some Typical Antimicrobial Methods

| Testing Method | | Standards | Test Materials and Microbes Applied to | Testing Condition | Effect Assessment | Advantage/Disadvantage |
|---|---|---|---|---|---|---|
| Diffusion | Parallel Streak | AATCC 147 | Textile materials; antibacterial and antifungal | Place inoculated streaks on agar plates | Examine width of inhibitory zone. Qualitative | Simple and fast. Good for soluble and slowly releasable drugs; cannot apply to insoluble materials |
| | Halo (Hole) | ASTM E2149 Term 12 | Textile; paper; powder, etc.; antibacterial | Place antibacterial solution into a hole bored on inoculated media | Examine width of inhibitory zone. Qualitative | Simple and fast. Good for soluble drugs; not applicable to insoluble and slowly released materials |
| | Halo (Disc) | JIS L 1902 | Textile materials; antibacterial and antifungal | Place inoculated discs on agar plates | Examine width of inhibitory zone. Qualitative | Simple and fast. Good for soluble and slowly releasable drugs; not applicable to insoluble materials |
| | Plate | AATCC 30 | Textile sheet materials; antifungal | Static; inoculate on the surface of test materials | Observe growth of fungus on the surface; measure strength change. Semi-quantitative | Good for antimicrobial finishes. |
| Surface Inoculating | Plate | ASTM G21 | Polymeric sheets, films, tubs, rods; antifungal | Static; inoculate on the surface of medium and test materials | Observe visible growth on specimen. Semi-quantitative | Good for antimicrobial finishes. |
| | Plate | JIS Z 2801 | Plastic, metal, ceramic products; sheets, coatings; antibacterial and antifungal | Inoculating on surfaces of test materials and medium | Washing inoculated test sample, and measuring viable cells of bacteria. Quantitative | Good for antimicrobial finishes, and insoluble materials. |
| Dissolving | Shake Flask | AATCC 100 | Textile materials can absorb water; antibacterial | Dynamic, shake flask | Comparing results from test sample to simultaneously run controls by measuring bacteria reduction in suspension (inhibitory rate). Quantitative | Applicable to both soluble and insoluble specimens. Cumbersome and time consuming |
| | Shake Flask | ASTM E2149 | Fabric, paper, powder materials; antibacterial | Dynamic, shake flask | | |

[00214] Aside from the testing methods described above, the minimum inhibitory concentration (MIC) is another quantitative indicator of antimicrobial efficiency. It is defined as the lowest concentration of antimicrobial that will inhibit the visible growth of a microorganism after overnight incubation [105]. MIC has been considered as the most accurate standard for determining the susceptibility of organisms to antimicrobials and assessing the performance of all other testing methods.

[00215] In this study, both diffusion method and dissolving method were employed for antibacterial assessment.

3.3 Preparation of Materials and Microorganisms

(1) Preparation of Nutrient Media

[00216] There were three nutrient media prepared and used for antibacterial assessment in this study: Tryptone Glucose Extract Agar (TGEA), Tryptone Soy Agar (TSA), and Tryptone Soy Broth (TSB).

[00217] TGEA was made of agar (15.0g, Difco Agar Granulated, Becton, Dickinson and Company, Sparks, MD, Ref #214530), Pancreative digest of casein (5.0g, Difco Laboratories, Detroit, MI, Ref # 0259-17-9), Beef Extract (3.0g, Sigma Chemical Co. St. Louis, MO, Ref # B-4888), and Glucose (1.0g, Sigma Chemical Co. St. Louis, MO, Ref # G-8270) for every 1000 ml melting medium [106]. This medium has 7.0 of pH value at 25°C and is used for cultivating and enumerating microorganisms in water and dairy products. The procedure to prepare this media was as follows: add components to deionized water and bring volume to 1000 ml; mix thoroughly with magnetic stirring bar; gently heat and bring to complete boiling; autoclave at 15psi and 121°C for 25 minutes; cool to 45-50°C; pour into sterile petri dishes; condense for 10-15 minutes; turn upside down; incubate at 37°C for 24 hours; check contaminations. Every 1000 ml of boiling medium filled 45~50 dishes ($\phi$100×10 mm).

[00218] TSA is a universal medium used for culturing various microorganisms. It is mainly used as a growth medium to observe colony morphology, develop a pure culture, achieve sufficient growth for further biochemical testing, and culture storage. TSA was composed of agar granulated (15.0g, Difco Agar Granulated, Becton, Dickinson and Company, Sparks, MD, Ref #214530) and Tryptic Soy Broth (30.0g, Becton, Dickinson and Company, Sparks, MD, Ref #211825) for per 1000 ml melting medium. The procedure for preparing the TSA was the same as that used for TGEA.

[00219] TSB is a liquid medium, which typically used to generate bacterial suspension for determination of bacterial numbers. It was made by dissolving 30.0 grams of Tryptic Soy Broth into 1000 ml de-ionized water with boiling.

[00220] All of the media were autoclaved and incubated at 37°C for 24 hours to check for the presence of contamination.

(2) Preparation of Buffer Solution

[00221] The buffer solutions used in this study was $KH_2PO_4$ solution, which included stock solution (0.25 M $KH_2PO_4$) and working solution (0.3mM $KH_2PO_4$). The stock solution was prepared by dissolving 34.0g $KH_2PO_4$ into 1000 ml solution with distilled water. The pH value was adjusted to 7.2 with 1.0M NaOH. The stock buffer solution was stored at 4°C, and re-prepared every 6 months. The working buffer solution was diluted from the stock solution, autoclaved, incubated, stored at 4°C, and re-prepared every 2 months.

(3) Stock Cultures

[00222] In this study, all of the test bacteria, including *E. coli*, *S. aureus*, and *K. pneumoniae*, were originally cultivated from the stored pure cultures of bacterial species in Dr. Susan Bagley's Environmental Microbiology Laboratory in the Department of Biological Science at Michigan Technological University. The culture media used for growth and storage of the inoculants was Tryptone Soy Agar plates, which were prepared based on the procedure above. The stock cultures were kept in a biological refrigerating room that room temperature were maintained at 4°C, and routinely re-grown with the steak-plate method. Before experimentation, the stored culture was grown overnight in nutrient media at 36°C in a shaker.

(4) Determination of Populations of Inoculants

[00223] There are several methods had been well-recognized and used for quantitative measurement of microbial population (cell counts in bacterial suspension). These methods classified into four types including direct cell counts, viable cell counts, measuring biomass, and measuring cell product [107]. Among these methods, three typical measuring techniques, including direct microscopic count, plate count, and turbidity measurement, are mostly effective and broadly acceptable.

[00224] Direct microscopic count uses special slides (counting chambers) to determine total number of cells in the suspending medium under a microscope. It is rapid, but this technique can not distinguish living cells from dead cells, and is only effective when the cell population in the suspension is greater than $1 \times 10^7$ cells/ml.

[00225] Plate count (include pour-plate and spread-plate) is an indirect viable cell count technique, which measures the concentration of cells by spreading a sample of culture on a nutrient agar surface. If the medium is appropriate, each viable cell (or unit) grows and forms a colony, which is called colony forming unit (CFU). The number of CFU indicates the number of viable bacteria in the suspension. This technique has good sensitivity to detect even a single cell. This technique is time-consuming, and can only detect living cells raised colonies, and the suspension contains more than 100 cells/ml. Clusters and chains of cells may develop into a single colony.

[00226] Turbidity measurement determines the number of cells by measuring turbidity (cloudiness) of microbial suspension under a specific light wavelength with a spectrophotometer. It is fast and nondestructive, but the suspending medium or broth must have no other particles or clumps except the specific organism. In order to determine the cell numbers by measuring turbidity, a correlation between optical absorbance and cell concentration for the specific microbe must be previously established combined with other count methods. This method also can not determine cell numbers if less than $1 \times 10^6$ or $1 \times 10^7$ cells/ml.

[00227] In this study, turbidity measurement was used as a main method to pre-determine density of cells in the inoculated bacterial suspensions when the density is greater than $10^7$ CFU/ml. Standard plate count was employed for viable cell number counts in the suspension. The direct microscopic count technique was used to verify the cell numbers combinated with the turbidity measurement. The determinations of cell numbers of specific organisms were performed as following.

*(a) Staphylococcus aureus*

[00228] Transferred 50 ml of sterilized TSB into a sterile 200 ml Pyrex flask, plus 1 loop of culture; shaked at 35°C incubator overnight; transferred 1.0 ml turbid culture to a centrifuge tube, and centrifuged at 10,000 rpm for 5 min. Diluted the inoculants with 1.0 ml sterile working buffer solution, let the inoculants suspend. The dilution was transferred into a sterile glass tube with 3~4 ml working buffer solution (this is as the $10^0$ dilution). Made 10 folds of series dilutions ($10^0$, $10^{-1}$, $10^{-2}$, and $10^{-3}$).

[00229] Spectrophotometer (Thermo Electron Corporation, Model: Thermo 4001/4) was calibrated at 600 nm of wavelength with working buffer solution. The series solutions of inoculants were measured with the optical absorbance of dilutions, respectively. The correlation of optical absorption and bacterial density was correspondingly established.

[00230] The bacterial densities (in colony number) of the dilutions were measured by direct count technique (hemacytometer). The detailed procedure for measurement was: remove 1.0 ml of dilution into a sterile glass tube; add 1 drop of crystal violet; shake and transfer approximate amount into the hemacytometer chamber; let stand for 3 minutes; and take photos with image program, ImagePCb1a. For each dilution, count 30~36 small squares (the square volume is $\frac{1}{400} mm^2 \times \frac{1}{50} mm = 5 \times 10^{-8} ml$). Table 5 shows the relation of optical absorbance and bacteria density.

Table 5. Relation of Optical Absorbance and Bacteria Density of S. aureus

| Dilution | Absorbance | Counted Squares | Total Cells Counted | Average Cells Per Square | Bacterial Density (CFU/ml) |
|---|---|---|---|---|---|
| $10^0$ | 1.058 | | | | |
| $10^{-1}$ | 0.172 | 32 | 792 | 24.8 | $5 \times 10^8$ |
| $0.2 \times 10^{-1}$ | 0.037 | 36 | 151 | 4.2 | $8.4 \times 10^7$ |
| $10^{-2}$ | 0.024 | 30 | 85 | 2.83 | $5.7 \times 10^7$ |
| $10^{-3}$ | 0.018 | 36 | 18 | 0.5 | $1 \times 10^7$ |

Figure 29:
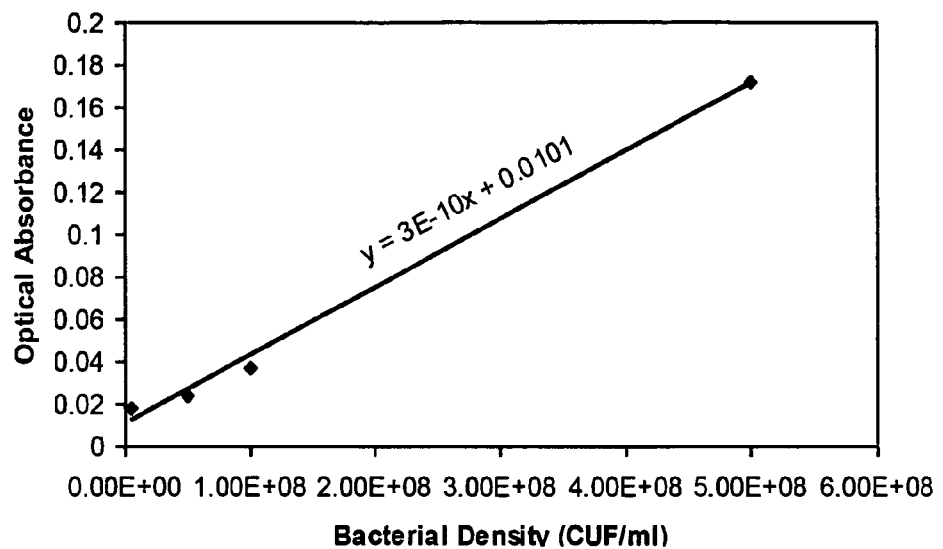

[00231] According to $1 \times 10^{-1}$ and $0.2 \times 10^{-1}$ dilutions, refer to the $1 \times 10^{-2}$ dilution, the calibrated bacteria density of $10^0$ dilution is approximately $5 \times 10^9$ CFU/ml. The calibrated working curve is shown in Fig. 29. The relationship of absorption versus bacterial density can be expressed as $$Y = 3 \times 10^{-10} X + 0.0101 \tag{6}$$

Where Y is optical absorption, X is bacterial density (CFU/ml).

(b) *Klebsiella pneumoniae*

[00232] According to ASTM E2149-01 [103], the $1.5 \times 10^5$ CFU/ml working dilution of *Klebsiella pneumoniae* can be prepared as follows: Grow a fresh 18 hours shake culture of *Klebsiella pneumoniae*; dilute the culture with the sterile working buffer solution until the solution get an absorbance of 0.28 ± 0.01 at wavelength of 475 nm, as measured spectrophotometrically. The cell concentration of *Klebsiella pneumoniae* in this solution will be $1.5 \sim 3.0 \times 10^8$ CFU/ml. Dilute appropriately into sterile buffer solution to obtain a final concentration of $1.5 \sim 3.0 \times 10^5$ CFU/ml.

(c) *E. coli*

[00233] The procedure and measured results were:

Transferred 50 ml sterilized TSB into a sterile 125 ml Pyrex flask, added 1 loopful of culture of *E. coli*; shook at 35°C incubator overnight; transferred 1.0 ml culture to a centrifuge tube, centrifuged at 10,000 rpm for 5 min; diluted the inoculants with 1.0 ml sterile 0.3 mM $KH_2PO_4$ buffer solution, let the inoculants suspended; transferred the dilution into a sterile glass tube with 5~7 ml buffer solution (this is set up as $10^0$ dilution).

[00234] Calibrated spectrophotometer at 600 nm of wavelength with working buffer solution; made series dilutions ($10^0$, $10^{-1}$, $10^{-2}$, $10^{-4}$, $10^{-5}$, $10^{-6}$, $0.5 \times 10^0$, and $0.2 \times 10^0$); measured the absorbance of dilutions, respectively.

Figure 30:
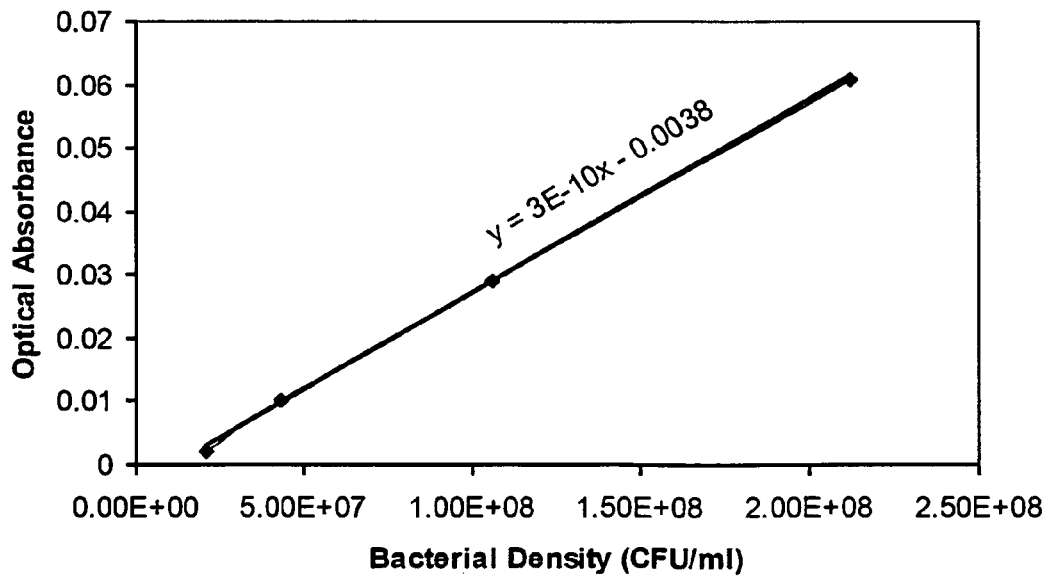

[00235] For each of the dilutions of $10^{-2}$, $10^{-4}$, $10^{-5}$, and $10^{-6}$, 100 μl were transferred to TSA plates, respectively, for standard plate culture; the inoculants were distributed by glass beads. The plates inoculated were sealed, inverted, and incubated at 37°C incubator. After 20 hours, the average colonies numbers of the dishes were counted. The plate culture was triplicate. According to the measurement above, the relation equation of absorbance and bacterial density of E. coli can be described as $$Y = 3 \times 10^{-10} X - 0.0038 \tag{7}$$

where Y is optical absorption, X is bacterial density of E. coli (CFU/ml). The calibrated cell density curve (working curve) is shown as Fig. 30.

3.4 Antibacterial Activities of Copper Vermiculite by Diffusion Method

3.4.1 Materials and Sampling

[00236] Test samples in this evaluation included copper vermiculite (MCV) and exfoliated copper vermiculite (MECV) prepared as shown in Chapter 2. For direct comparison, micron sized vermiculite (VV-CCE) and exfoliated vermiculite (VV-7) were employed as control samples to MCV and MECV, respectively. Distilled water was also used as a control sample with liquid diffusion procedure. All the samples were dried at 105°C, and gently ground into loose powder.

3.4.2 Assay Procedures

Figure 31:
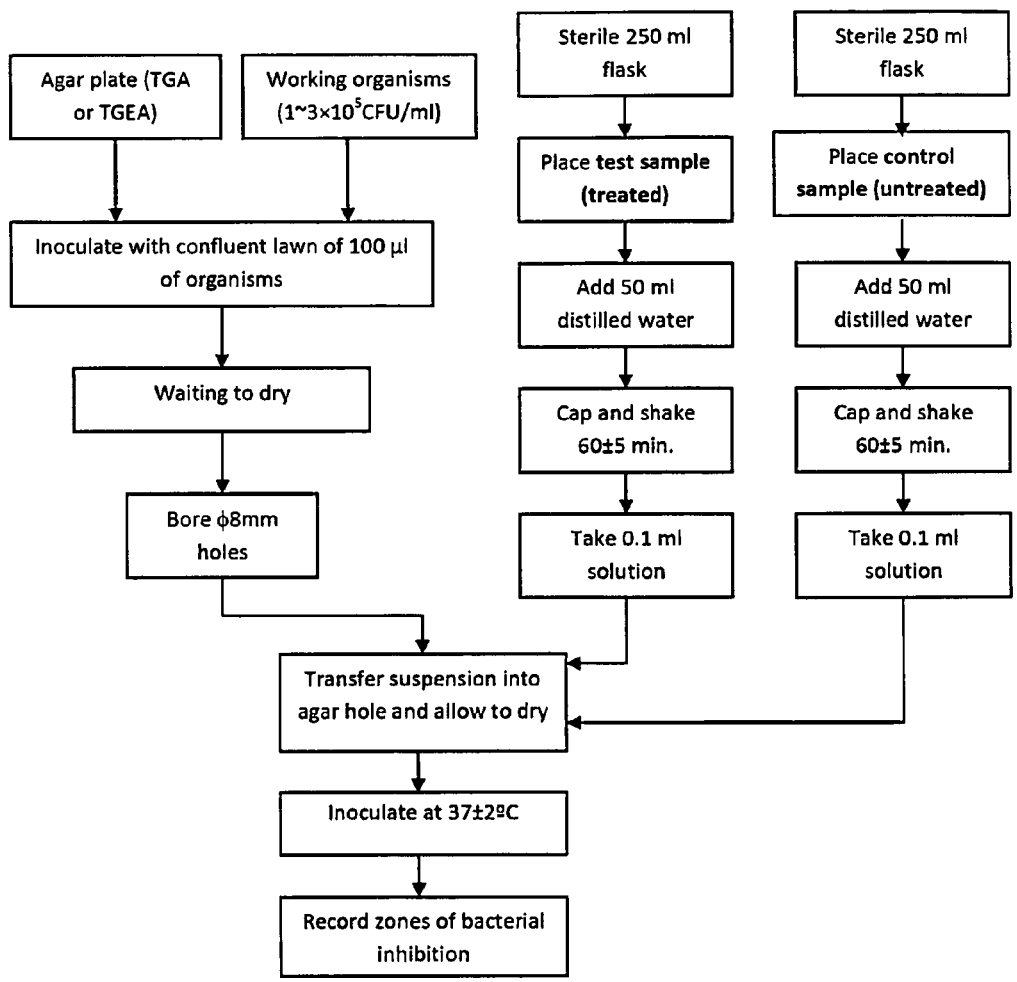
Figure 32:
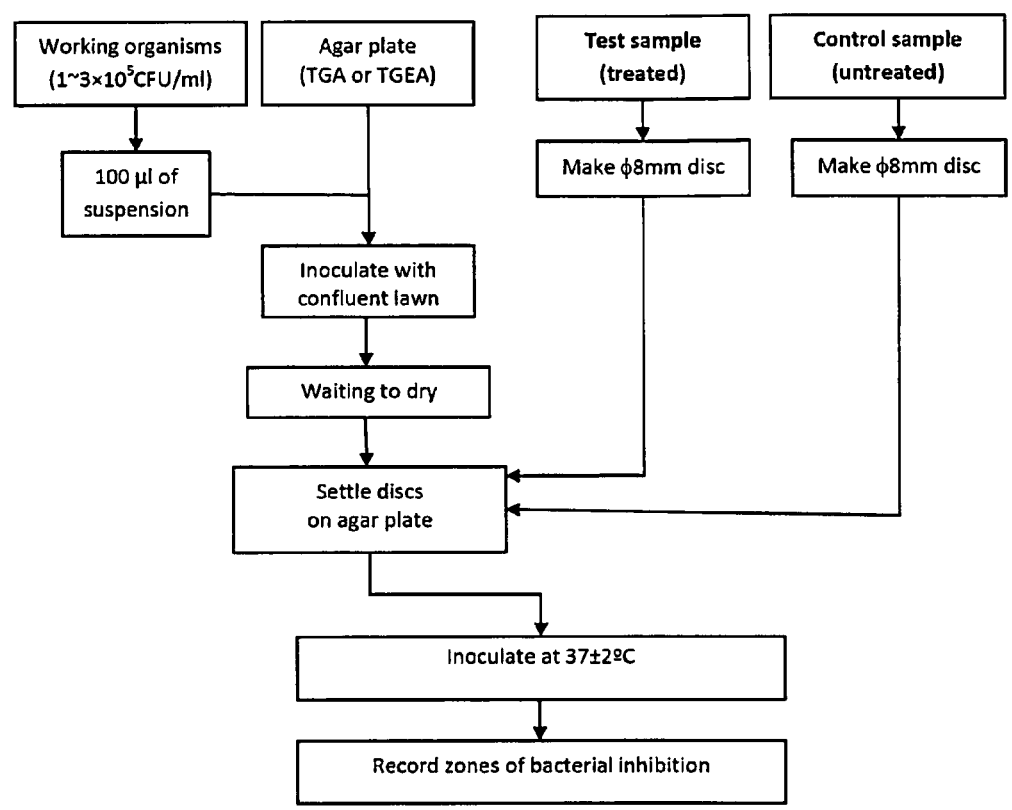

[00237] Both liquid diffusion method (supernatant method) and solid diffusion method (disc method) were used for the antibacterial tests. The liquid diffusion method used dissolved supernatant from test and control samples in holes bored in an agar media plate, while the solid diffusion method located sample discs directly on the agar plate. The procedures are shown as Fig. 31 and Fig. 32.

3.4.3 Results

3.4.3.1 Antibacterial Activity of Copper Vermiculite by Liquid Diffusion Method (Hole Method)

**(1) Testing against *Staphylococcus aureus* on media TGEA**

Figure 33:
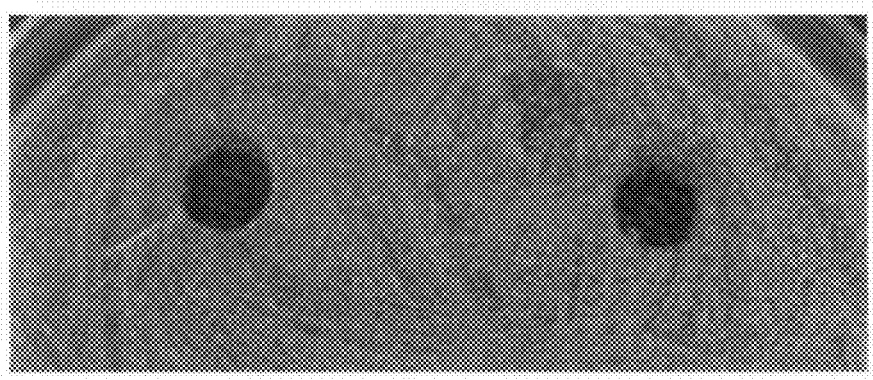
Figure 34:
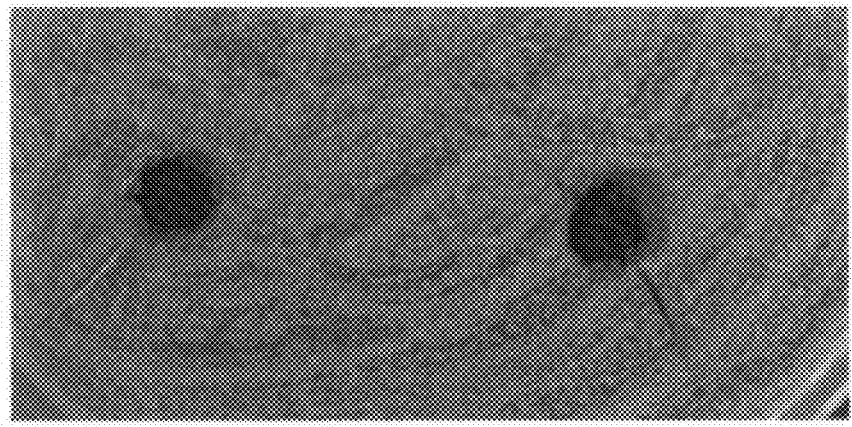

[00238] Fig. 33 and 34 show that the testing results of leaching solutions of copper vermiculite (MCV) and coarse copper vermiculite (MCCV, copper cation exchanged from VV-5) against *S. aureus* on media TGEA. Jet-milled vermiculite (VV-CCE) and coarse vermiculite (VV-5) were used as control samples, respectively.

[00239] Combined with 1 hour shaking, the leached solution of copper vermiculite (MCV) did not show any inhibiting zone around the holes against *S. aureus* (Fig. 33). The coarse copper vermiculite (MCCV) was similar (Fig. 34). However, there was no visible bacterial colony formed within the holes.

**(2) Testing against *Staphylococcus aureus* on media TSA**

Figure 35:
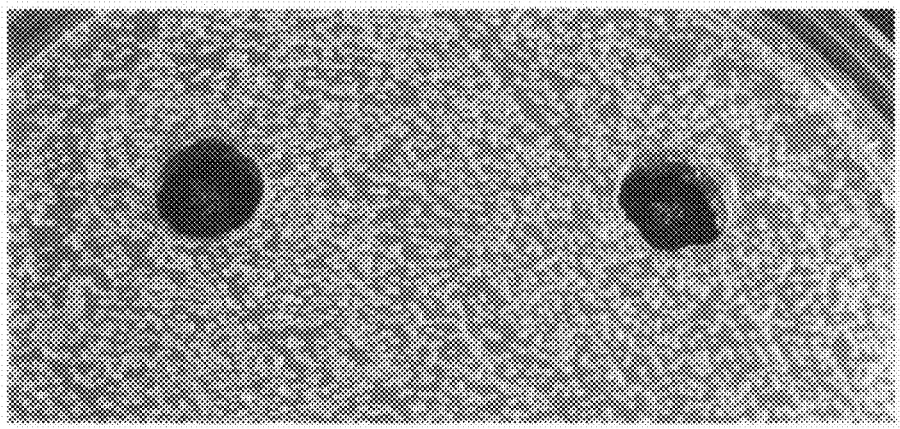
Figure 36:
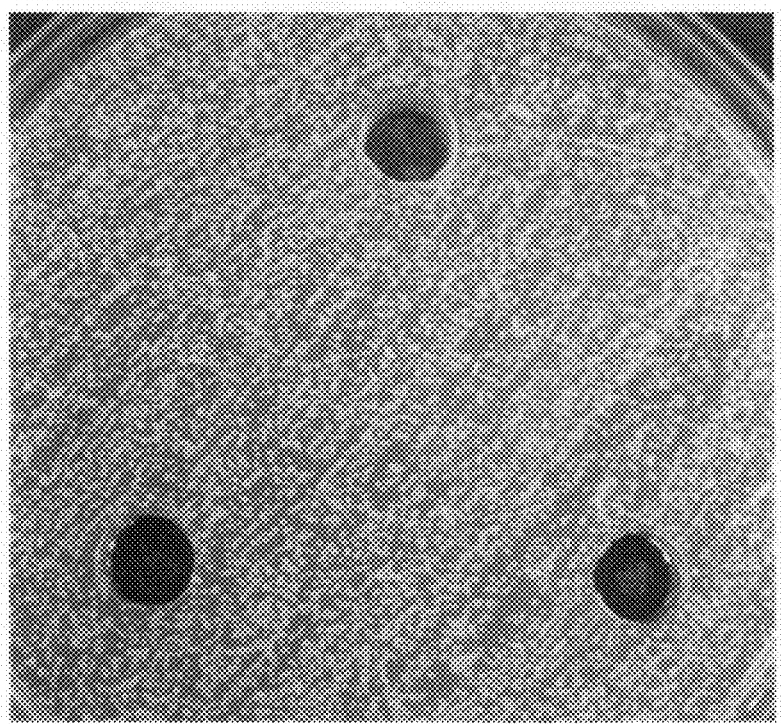

[00240] Fig. 35 and 36 show that the testing results of leaching solutions of MCV for 1 hour, MCV for 28 days, MECV for 1 hour against *S. aureus* on media TSA, respectively.

[00241] The leached solution of MCV and MECV also did not show significant antibacterial properties against *S. aureus* on media TSA (Fig. 35). Even the solution of MCV shaked for 28 days had not shown an improved effect (Fig. 36).

**(3) Testing against *Klebsiella pneumoniae* on media TSA**

Figure 37:
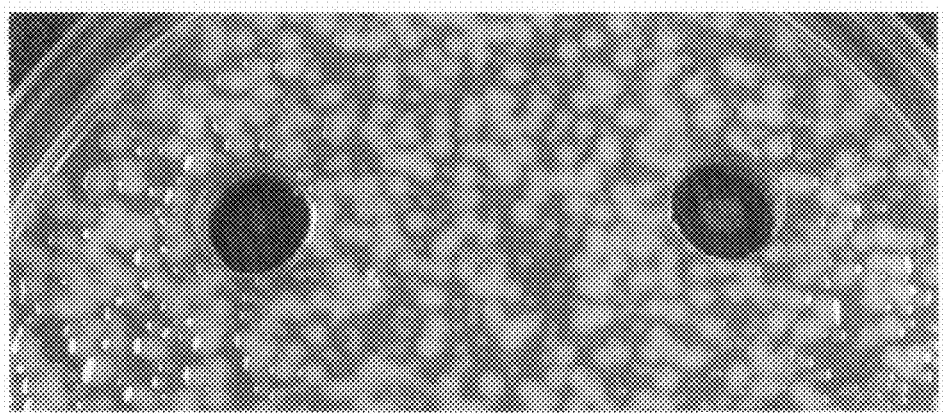

[00242] Fig. 37 shows that the testing results of 1 hour leaching solutions of MCV, and MECV against *K. pneumoniae* on media TSA. There were no inhibitory zone around the holes, and bacterial colony within the holes.

(4) Testing against *E. coli* on media TSA

Figure 38:
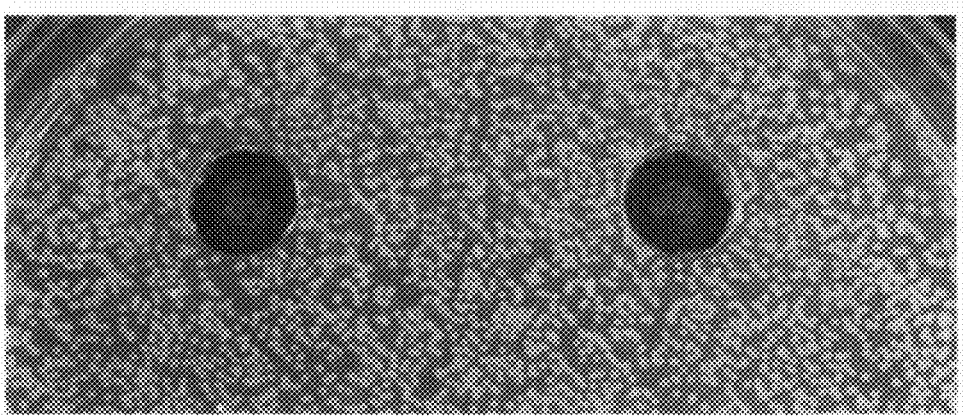
Figure 39:
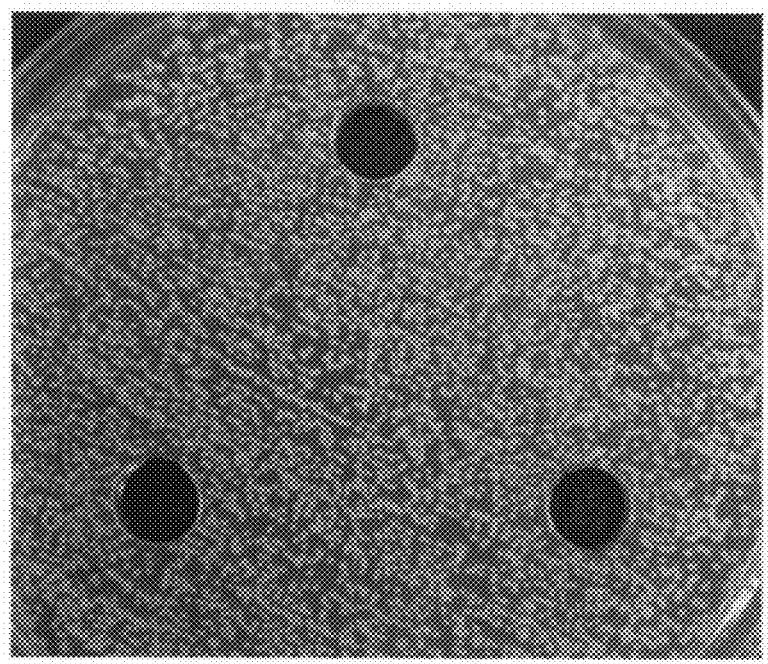

[00243]  Fig. 38 and 39 show that the testing results of 1 hour leaching solutions of MCV, MECV, and 28 day solution of MCV against *E. coli* on media TSA. The results were similar to that against *S. aureus* and *K. pneumoniae*.

3.4.3.2 Antibacterial Activity of Copper Vermiculite by Solid Diffusion (Disc Method)

[00244]  Since the liquid diffusion method could not distinguish the difference of antibacterial behaviors among copper vermiculite, exfoliated copper vermiculite, and control samples, the solid diffusion method (disc method) was employed for antibacterial evaluation of copper vermiculite and exfoliated copper vermiculite. The test results has exhibited that this method is applicable to test of copper vermiculite.

(1) Testing against *Staphylococcus aureus*

Figure 40:
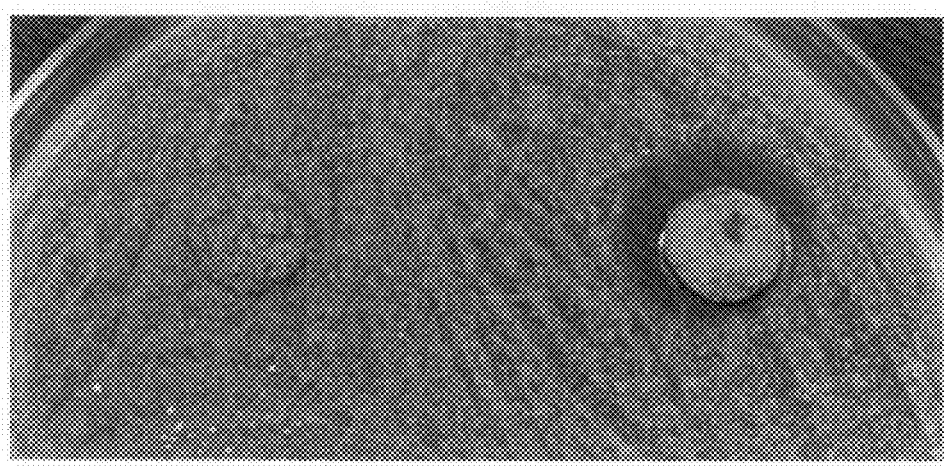
Figure 41:
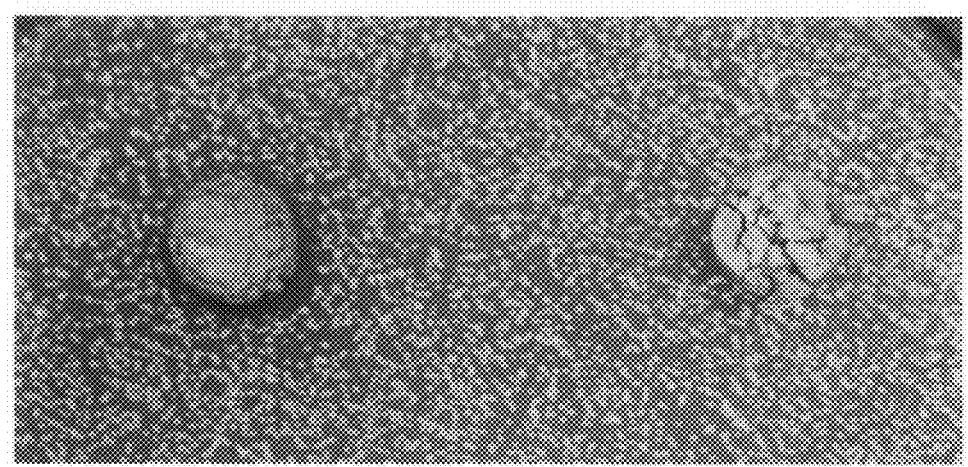
Figure 42:
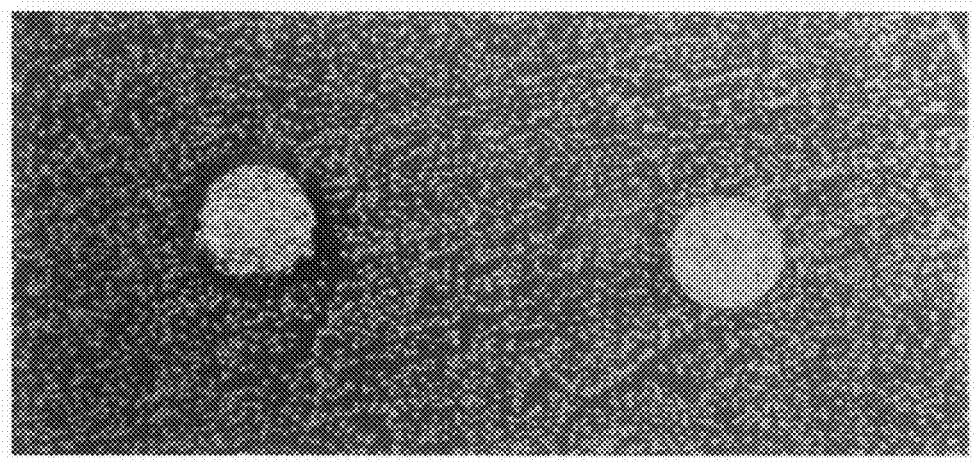

[00245]  Fig. 40, 41, and 42 show that the testing results of MCV and MECV against *S. aureus* on media TEGA and TSA, respectively. The amount of copper vermiculite used for each disc was 0.05g (containing 1.28 mg of copper atoms). The amount of exfoliated copper vermiculite used for each disc was 0.02g (containing 0.47 mg of copper atoms).

[00246]  By means of the disc method, copper vermiculite had clearly shown excellent antibacterial effect comparing to untreated vermiculite (VV-CCE) on media TGEA (Fig. 40). The inhibiting zone was as wide as 4 mm out from the edge of disc (The inhibiting zone of MCV was not symmetrical since the agar plate next to the lower edge of the disc was broken when place the disc on the inoculated plate). There was no bacterial colony occurred on the surfaces of both MCV and VV-CCE.

[00247]  On media TSA, both MCV and MECV displayed a smaller inhibitory zone than that on TGEA Fig. 41, 42). The inhibiting zones reduced to 2 mm away from the disc. This might be caused by that the copper has a faster diffusion speed in TEGA than that in TSA. However, MECV shown a similar width of zone to MCV, even the former has a higher copper concentration.

(2) Testing against *Klebsiella pneumoniae*

[00248] Fig. 43, and 44 show that the testing results of MCV and MECV against *K. pneumoniae* on media TSA, respectively. The amount of copper vermiculite used for a disc was 0.04g (containing 1.02 mg of copper atoms). The amount of exfoliated copper vermiculite used for each disc was 0.03g (containing 0.70 mg of copper atoms). Although the inhibiting zones were not regular in shape, the colony size and colony number of *K. pneumoniae* were significantly reduced around the discs of MCV and MECV. The colors of the colonies were become light. This also shows good antibacterial effect of copper vermiculite, whereas the untreated vermiculite (VV-CCE and VV-7) had no impact on the bacteria (Fig. 43, 44). The efficient zones with antibacterial impact were as wide as 3-6 mm away from the edges of discs. Also, there was colony formed on the surface of the disc of VV-CCE.

(3) Testing against *E. coli*

Figure 45:
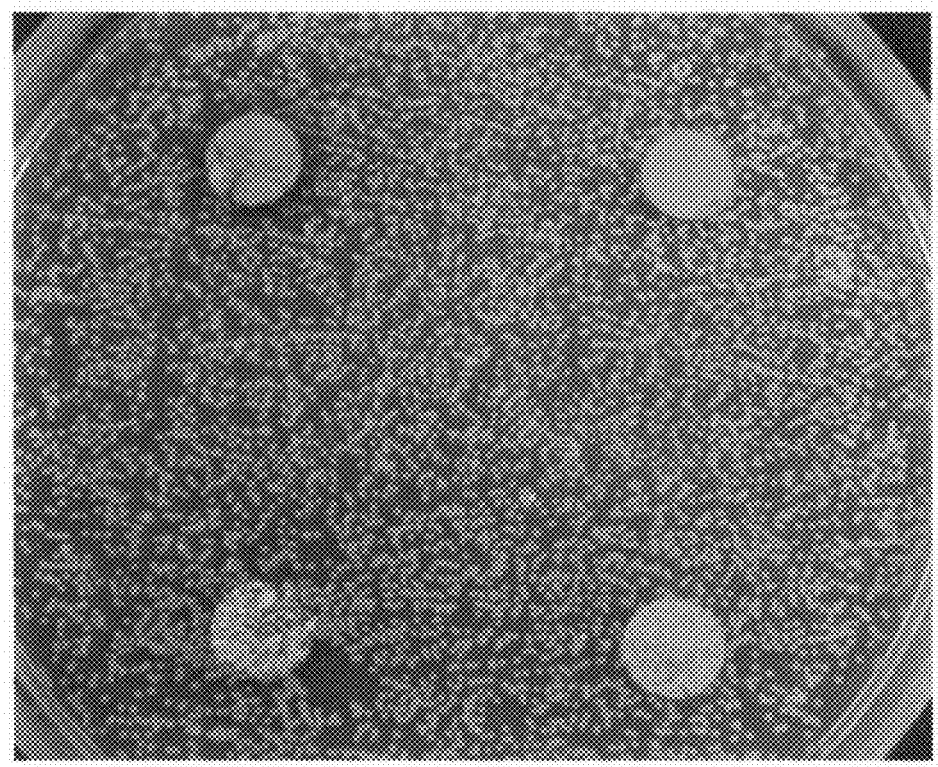

[00249] Fig. 45 shows that the testing results of MCV and MECV against *E. coli* on media TSA, respectively. The amount of copper vermiculite used for the disc was 0.05g (containing 1.28 mg of copper atoms). The amount of exfoliated copper vermiculite used for the disc was 0.02g (containing 0.47 mg of copper atoms). In this experiment, the colony size and colony number of *E. coli* were also reduced around the discs of copper vermiculite and exfoliated vermiculite, while the controls had no impact on bacteria. The efficient zones with antibacterial impact were 4-6 mm away from the edges of discs.

[00250] In summary, although the width of the inhibiting zone depends on various experimental factors, such as the test method, materials, specific species of organism, copper content, and the weight of the sample, the samples loaded copper have clearly shown antibacterial effects. By means of the disc method, copper vermiculite showed antibacterial efficiency to *S. aureus*, *K. pneumoniae* and *E. coli*. Antibacterial ability of copper vermiculite increases in the order: *E. coli*, *K. pneumoniae*, and the strongest antibacterial nature of copper vermiculite was its action against *S. aureus*. Table 6 shows the comparison of antibacterial effects based on the test results by solid diffusion method (disc method) above. The narrow inhibiting zones exhibited the slow release mechanism of copper vermiculite which is different from the antimicrobial drugs which mostly are soluble in a short time.

Table 6. Comparison of Antibacterial Effects based on Solid Diffusion (Disc) Method

| Test Bacterium | | S. aureus | K. pneumoniae | E. coli |
|---|---|---|---|---|
| MCV (on TSA) | Disc Weight (g)/Cu Contained (mg) | 0.05/1.28 | 0.04/1.02 | 0.05/1.28 |
| | Inhibiting Zone* (mm) | 2 | | |
| | Impacted Zone (mm) | | 3-6 | 4-6 |
| MCV (on TGEA) | Disc Weight (g)/Cu Contained (mg) | 0.05/1.28 | | |
| | Inhibiting Zone (mm) | 4 | | |
| MECV (on TSA) | Disc Weight (g)/Cu Contained (mg) | 0.02/0.47 | 0.03/0.70 | 0.02/0.47 |
| | Inhibiting Zone (mm) | 2 | | |
| | Impacted Zone (mm) | | 3-6 | 4-6 |
| Controls** | | No impact | No impact | No impact |

\* Impacted zone is the area where the colony number and size were reduced.

\*\* All controls did not show impact to the colonies of bacteria.

[00251] According to the test results by liquid diffusion method (hole), all the leaching solutions of copper vermiculite and exfoliated copper vermiculite have no inhibiting zones around the holes on TSA and TGEA. However, there was bacterial colony formed inside the holes. This implies that the release velocity of copper from copper vermiculite into the liquid is very slow.

Figure 46:
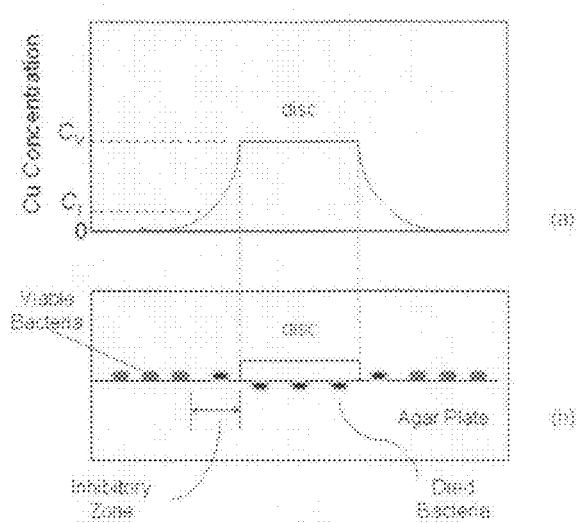
Figure 47:
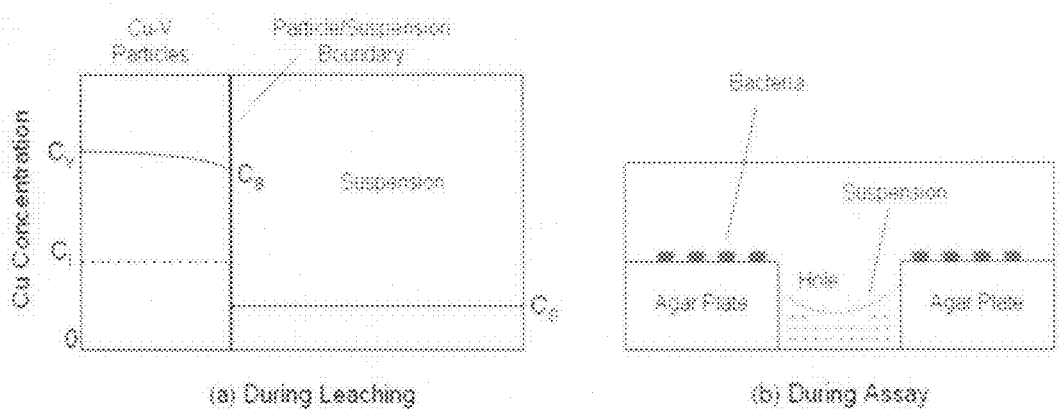

[00252] The difference of the antibacterial effects of copper vermiculite (and exfoliated vermiculite) by liquid diffusion and solid diffusion can be explained with the models in Fig. 46 and 47. When the test was performed via solid diffusion method and the disc was settled on the agar plate (Fig. 46), the copper ions in vermiculite would be released from the disc onto the surface of agar plate, due to the increased relative moisture around particles of copper vermiculite. The release activity would start from those particles located at the edge and bottom of the disc. Accordingly, the copper concentration maintained a constant at the center and top of the disc ($C_V$), but gradually reduced along with the distance away from the disc (Fig. 46a). If only the copper concentration on the surface of agar plate was greater than the concentration effective to inhibit bacterial replication ($C_I$), the bacterial colony in this area can not grow up, the inhibiting zone was formed at such area (Fig. 46b). In the area where copper ions were dispersed but the concentration was still lower than $C_I$, the colony number and size of bacteria would be reduced.

[00253] Liquid diffusion method provided a different approach for the diffusion of copper ions (Fig. 47). During leaching process, the copper ions were released from vermiculite particles into the solution. The copper concentration at the edge of vermiculite particle ($C_B$) would be lower than that at the center of the particle ($C_V$) due to the diffusion progress. $C_S$ was also much lower than $C_B$ due to the structural stability of copper in vermiculite (According to the investigation on chemical stability of copper in Chapter 4, this concentration was only 1-3 ppm). $C_I$, the concentration of copper in solution which required to high enough to be dispersed to the surface of agar plate, and further effective to inhibit bacterial growth, could be lower or higher than $C_B$, depended on the inhibiting need on agar surface (Fig. 47a).

[00254] During assay process, copper ions in the leached solution can be only dispersed through the body of agar plate toward the surface of agar plate, since the volume of solution transferred (100µl) was much smaller than that of the hole (150-200µl). Most of the copper ions would have been homogenously absorbed by the porous agar plate around the hole before they were able to reach the agar surface, unless the $C_S$ was at a very high level (Fig. 47). This is the reason why copper vermiculite and exfoliated copper vermiculite could not show inhibiting zone through the liquid diffusion method, while without bacterial colony formed inside the holes.

[00255] Comparably, exfoliated copper vermiculite (MECV) demonstrated more efficient antibacterial ability than un-exfoliated copper vermiculite (MCV). The copper content in each disc of copper vermiculite is approximately 1-1.3 mg, while exfoliated copper vermiculite contained only 0.5-0.7mg. This may be resulted from that the exfoliated copper vermiculite has much more free surface during exfoliation. Consequently, more copper ions were physically absorbed on the free surface of vermiculite sheets, which led to a rapid release rate of copper ions from vermiculite.

[00256] TGEA appears to have a fast diffusion rate of copper than TSA. The reason needs more investigation to be done. Term 12 in ASTM 2149-01 is not suitable to antibacterial testing for insoluble (or slow release) materials, such as copper vermiculite, as the high metal concentration requirement discussed above. The disc method is a more efficient method to evaluate the antibacterial effect of powder materials, like vermiculite.

3.5 Quantitative Assessment of Antibacterial Effects of Copper Vermiculite

[00257] To quantitatively evaluate the antibacterial effects of copper vermiculite and exfoliated copper vermiculite, the reduction rate (death rate) of bacteria were investigated.

3.5.1 Test organism

[00258] The microorganism selected for this assay is *E. coli*, since it is well-recognized indicator of antibacterial efficiency.

3.5.2 Procedure (1) Preparation of Bacterial Inocula

[00259] The microorganism stocks were maintained on TSA plates and stored at 4°C. For each new experiment, fresh cultures were grown on TSA at 37°C for 15-18 hours before use (as they entered stationary phase). During experiment, stock cultures were transferred into a 125 ml Pyrex flask containing 50 ml sterilized TSB, and the fresh culture was grown by shaking at 37°C for 12~18 hours (as they entered stationary phase). The culture was centrifuged at 10,000 rpm for 5 min, then diluted, transferred and suspended in autoclaved phosphate buffer solution (0.3mM $KH_2PO_4$).

[00260] Calibrated spectrophotometer at a 600 nm wavelength with the buffer solution. The culture was diluted with the sterile buffer solution until the solution had an absorbance of 0.058±0.001 at 600 nm, based on the correlation curve measured in Section 3.3. This has a concentration of 1~2 ×10$^8$ CFU/ml as previous assay. The final concentration was adjusted to 1~2×10$^7$ CFU/ml before use.

(2) Procedure of Determining Antibacterial Activity

[00261] Six sterilized 250 ml glass flasks was prepared and poured with 99.0 ml sterilized buffer solution (0.3mM KH$_2$PO$_4$), respectively. Among these flasks, four were used for adding various weights of copper vermiculite, and other two were used for controls (control 1 had no vermiculite; control 2 had untreated vermiculite powder). The buffer solution had been pre-warmed to 37°C to prevent any temperature shock to bacteria cells. 1.0 ml 1~2×10$^7$ CFU/ml of bacteria dilution were transferred into each flask, then continuously shaken at 37°C and instantly added the test samples into the flasks. After shaken in 37°C incubator for 5 minutes, set the time as "0" contact time. At "0" and other desired contact time, performed series dilutions and standard plate count to determine the cell number in the flasks.

[00262] A 100 μl of aliquot of each dilution was pipetted onto a TSA plate which had been pre-warmed to room temperature (21°C). The inoculant was then spread over the surface of the plate using 4 sterilized, disposable glass beads. Agar plates were inverted by turning lid down and incubated at 37°C for 15~24 hours before the colonies were counted. All the inoculations were replicated with 3 plates for each dilution.

3.5.3 Results and Discussions

[00263] Results show that the copper vermiculite has strong antibacterial activity against *E. coli*. (Table 7 and Fig. 48). In untreated vermiculite suspension (Control 2), bacteria density remained constant during 12 hour contact time. However, within the suspensions of copper vermiculite, the viable bacteria were significantly decreased. With 20.0 mg copper vermiculite in 100.0 ml bacteria dilution (containing 200 ppm copper vermiculite, or 5.10 ppm of copper atoms), the reductions of viable bacteria are 94.8% at 1 hour, 99.6% at 2 hours, and >99.9% at 4 hours.

Table 7. Viability of *E. coli* Exposure to Copper Vermiculite

| Incubabed Time (h) | Copper Vermiculite Added in 100.0 ml Buffer Solution | | | | | |
|---|---|---|---|---|---|---|
| | Control 1 (Inocula only) | Control 2 (Vermiculite 10.0mg, without Cu) | Copper Vermiculite (Cu content) | | | |
| | | | 1.0 mg (0.03ppm) | 5.0 mg (0.13ppm) | 10.0 mg (0.26ppm) | 20.0 mg (5.10ppm) |
| 0 | $1.66 \times 10^5$ | $1.52 \times 10^5$ | $1.56 \times 10^5$ | $1.43 \times 10^5$ | $1.46 \times 10^5$ | $1.20 \times 10^5$ |
| 1 | $1.34 \times 10^5$ | $1.55 \times 10^5$ | $9.15 \times 10^4$ | $6.18 \times 10^4$ | $2.57 \times 10^4$ | $6.20 \times 10^3$ |
| 2 | $1.17 \times 10^5$ | $1.42 \times 10^5$ | $4.50 \times 10^4$ | $1.13 \times 10^4$ | $1.02 \times 10^4$ | $5.10 \times 10^2$ |
| 4 | $7.45 \times 10^4$ | $1.76 \times 10^5$ | $6.70 \times 10^3$ | $1.46 \times 10^3$ | $1.41 \times 10^3$ | <20 |
| 8 | $3.85 \times 10^3$ | $1.49 \times 10^5$ | <70 | <10 | | |
| 12 | <10 | $1.28 \times 10^5$ | | | | |

Figure 48:
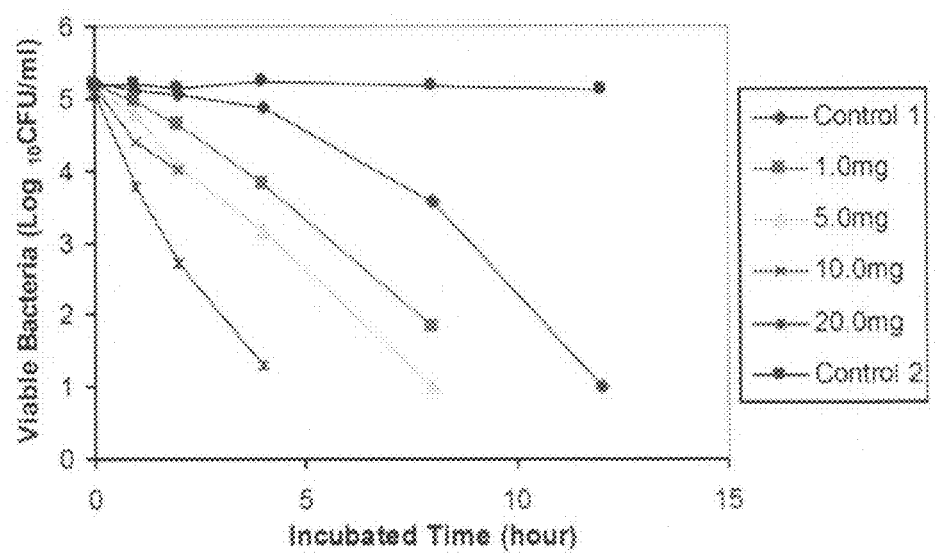

[00264] Since the phosphate buffer saline used can only maintain the pH value of the bacteria suspension at 7.0 rather than provide nutrient substance to *E. coli*, the shortage of nutrition in media resulted in the death of *E. coli* cells, and the reduction of cell population gradually, shown as the curve of control 1 in Fig. 48. There are only 2.32% of inoculums remaining viable after 8 hours of contact time.

[00265] Addition of copper vermiculite in the bacteria suspensions accelerated the death of *E. coli* cells due to the inhibition of copper ions to metabolism of bacteria. This made a sharp reduction curve of cell numbers during incubating process. The more copper vermiculite added, the rapider the death of bacteria was. It was clear that the viable population of *E. coli* was effectively reduced by adding even 1.0 mg of copper vermiculite in the suspension (as containing 0.255 ppm of Cu). This result showed that copper vermiculite has strong antibacterial ability against *E. coli* even at a low concentration level. Compared to the antibacterial results by diffusion methods, copper vermiculite exhibited a stronger antibacterial ability in liquid media than on solid media. The solution suspending with both copper vermiculite particles and bacterial cells enhanced interaction between cells and copper vermiculite particles. Direct contact of copper ions with bacterial cells played a critical role to antibacterial efficiency of copper-based materials.

[00266] It should be mentioned that some documents described vermiculites as having natural antimicrobial properties [108]. All the experiment in this study demonstrated that untreated vermiculite actually had no antibacterial activity on $E.\ coli$. This may be caused by the leaching of some elements, such as iron, magnesium, or absorption of vermiculite to anions of phosphate.

[00267] According to the assay showed in Table 7, the reduction curves of different solutions can be mathematically expressed as:

Control 1: $X = -0.0858t + 5.2221$ (during 0-4 hour) (8)

$X = -0.484t + 7.0247$ (during 4-12 hour) (9)

Control 2: $X = -0.0054t + 5.1992$ (10)

1.0mg: $X = -0.4276t + 5.3786$ (11)

5.0mg: $X = -0.5234t + 5.203$ (12)

10.0mg: $X = -0.5779t + 5.1055$ (13)

20.0mg: $X = -0.929t + 4.8458$ (14)

Where $X$ is cell number of bacteria in logarithmic scale, $t$ is process time (hour). The specific death rates can be described as [93]

$$dX/dt = -k'\Delta X \quad (15)$$

Where $k'$ is specific death rate (1/hour), $dX$ is the difference of cell number of bacteria during a time interval $dt$. $\Delta X$ is reduction of bacterial population over $dt$ in logarithm. For the case reduction rate of 99% of bacterial population, the specific death rate will be $$k' = -(dX/dt)/\Delta X = -(dX/dt)/\log_{10}(\frac{1}{100})$$

or, $$k' = \frac{1}{2}\left(dX/dt\right) \tag{16}$$

[00268] Consequently, the specific death rates of *E. coli* in the different solutions containing copper vermiculite are showed as Table 8.

Table 8. Specific Death Rates of *E. coli* in the Solutions Treated with Copper Vermiculite

| Sample Solution | Control 1 (0-4 hour) | Control 1 (4-12 hour) | Control 2 | 1.0mg | 5.0mg | 10.0mg | 20.0mg |
|---|---|---|---|---|---|---|---|
| Specific Death Rate (1/hour) | -0.0429 | -0.0242 | -0.0027 | -0.2138 | -0.2617 | -0.2889 | -0.4645 |

Figure 49:
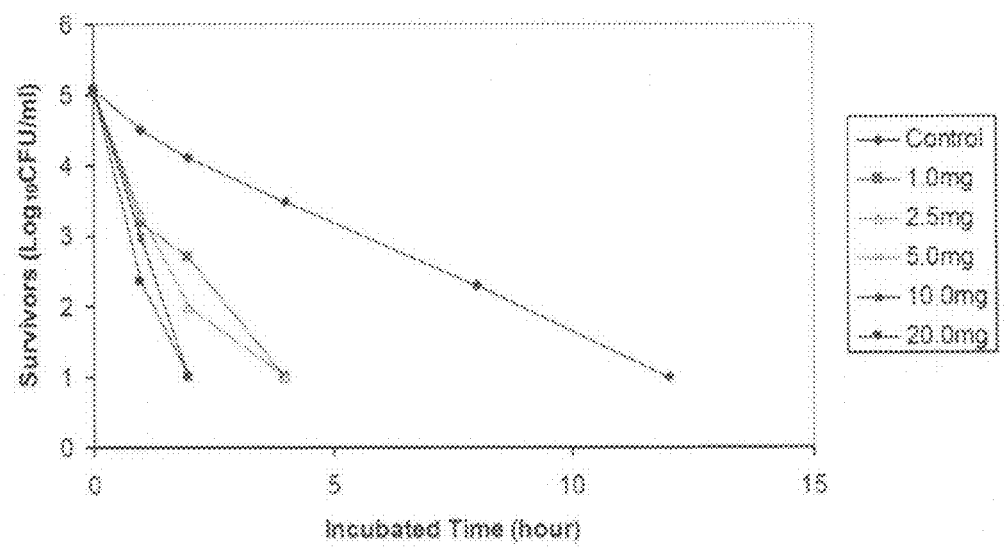

[00269] Further experiments show that the exfoliated copper vermiculite (MECV) even has stronger antibacterial activity than copper vermiculite (MCV) against *E. coli*. (Table 9 and Fig. 49). With 20.0 mg exfoliated copper vermiculite in 100.0 ml bacteria dilution (containing 200 ppm copper vermiculite, or 4.68 ppm of copper atoms), the reduction of viable bacteria are 99.8% at 1 hour, and >99.9% at 2 hours. With 1.0 mg exfoliated copper vermiculite in 100.0 ml bacteria dilution (containing 10 ppm copper vermiculite, or 0.234 ppm of copper atoms), the reduction of viable *E. coli* reached 98.7% at 1 hour, and >95.6% at 2 hours.

[00270] According to the assay showed in Table 9, the reduction curves of different solutions of exfoliated copper vermiculite can be mathematically expressed as:

| | |
|---|---|
| Control: $X = -0.3261t + 4.8794$ | (17) |
| 1.0mg: $X = -0.9501t + 4.6466$ | (18) |
| 2.5mg: $X = -0.9808t + 4.5568$ | (19) |
| 5.0mg: $X = -2.0303t + 5.0506$ | (20) |
| 10.0mg: $X = -2.0303t + 5.0432$ | (21) |
| 20.0mg: $X = -2.7183t + 5.0607$ | (22) |

Where $X$ denotes cell number of bacteria in logarithmic scale, $t$ denotes process time (hour).

Table 9. *E. coli* Counts by Plate Culture Method (CFU/ml)
(Exfoliated Copper Vermiculite)

| Shaking Time At 37°C (hours) | Exfoliated Cu-vermiculite in 100 ml of solution | | | | | |
|---|---|---|---|---|---|---|
| | 0 (Control) | Exfoliated Copper Vermiculite Added (mg) (Cu content, ppm) | | | | |
| | | 1 (0.23) | 2.5 (0.59) | 5 (1.17) | 10 (2.34) | 20 (4.68) |
| 0 | $1.15 \times 10^5$ | $1.15 \times 10^5$ | $1.15 \times 10^5$ | $1.15 \times 10^5$ | $1.15 \times 10^5$ | $1.15 \times 10^5$ |
| 1 | $3.3 \times 10^4$ | $1.5 \times 10^3$ | $2 \times 10^3$ | $<1 \times 10^3$ | 950 | 220 |
| 2 | $1.3 \times 10^4$ | <500 | <100 | <10 | <10 | <10 |
| 4 | $3 \times 10^3$ | <10 | <10 | <10 | <10 | |
| 8 | <200 | <10 | <10 | <10 | | |
| 12 | <10 | <10 | | | | |

[00271] Similar to Table 8, the specific death rates of *E. coli* in the different solutions containing exfoliated copper vermiculite are showed in Table 10.

Table 10. Specific Death Rates of *E. coli* in the Solutions Treated with Exfoliated Copper Vermiculite

| Sample Solution | Control | 1.0mg | 2.5mg | 5.0mg | 10.0mg | 20.0mg |
|---|---|---|---|---|---|---|
| Specific Death Rate (1/hour) | -0.1631 | -0.4751 | -0.4904 | -1.0152 | -1.0152 | -1.3592 |

3.6 Antifungal Activity of Copper Vermiculite

[00272] Molds have the potential to cause health problems, such as allergic reactions, irritations, and mycotoxins, and damages to buildings, historic relics, properties, etc. [109]. Since copper has better antifungal property, an initial antifungal activity of copper vermiculite was evaluated in this study.

(1) Test procedure

[00273] Placed dried test sample into an ultraviolet disinfected round polyethylene case with screwed lid; pipetted the Jilbert Fat-Free SkimMilk (Commercial product of Jilbert's Dairy Inc. Marquette, Michigan, USA) into the case until the test sample was saturated with the milk; placed the test sample into incubator to naturally develop molds; maintain the temperature of incubator at 36°C; watch the changes of the test sample.

[00274] In this assay, copper vermiculite (MCV) and exfoliated copper vermiculite (MECV) were tested. Untreated jet-milled vermiculite (VV-CCE), untreated exfoliated vermiculite (VV-7), white bentonite, and kaolin were used as control samples. All samples were 1.0 gram except MECV and VV-7 which were 0.5 gram in weight. According to the previous chemical analysis of copper concentration, the total weights of metallic copper in MCV and MECV placed were 25.5mg and 23.4mg, respectively.

(2) Results

[00275] After incubated for 24 hours, the untreated vermiculite (VV-CCE), exfoliated vermiculite (VV-7), like white bentonite, kaolinite, dwelled with foams, which indicated growth of molds. By 48 hours, all of the surfaces of VV-CCE, VV-7, bentonite, and kaolin have been covered by thick mold films (Fig. 50). However, the copper vermiculite and exfoliated copper vermiculite only shown the color of milk changed into green-gray, which indicated that copper had been released into the milk from vermiculite. Even after the incubation was lasted for 21 days, copper vermiculite and exfoliated copper vermiculite did not show any mold on the surface. These results exhibited copper vermiculite and exfoliated copper vermiculite have excellent antifungal activities against mold. The more detail antifungal assay for copper vermiculite is necessary.

3.7 Antimicrobial Mechanism of Copper Vermiculite

[00276] Although several metallic ions have extensive applications to antimicrobial purposes and a number of antimicrobial mechanisms of metals have been developed, the detail interaction mechanisms of microbe-metal are still remaining uncertain.

[00277] Metallic ions on the surface of an appliance or utensil that comes in contact with bacteria and other microbes disrupt the normal metabolism and replication functions of these cells. This typically results in microbial death [110].

[00278] Copper is both an essential micronutrient and a toxic heavy metal for most living cells. As an essential micronutrient is usually at very low concentrations of the metal (in the order of 1-10 µM)[111]. Antimicrobial activity of copper could be achieved through several different mechanisms. In general, the antimicrobial mechanism of copper is considered that results from its strong ionic nature. Once the metallic ion of copper diffuses across cell membrane of pathogenic microbe by various pathways, it inhibits the enzymatic activity by replacing other local metal ions within an enzyme. This substitution would render the enzyme misfunctional and the metabolism of microbe is disrupted [112-117]. Consequently, the replication of microbe is terminated. Several other mechanisms were also proposed based on ionic action of copper, such as disordering helical structures of nucleic acids [118], alteration of proteins and inhibition of their biological activity, oxidation of membrane components [119], generation of toxic hydroxyl free-radicals [120]. The most important is the interactions of copper with nucleic acids. The antimicrobial mechanisms were also considered as changeable against specific class of microorganisms [112]. Copper may also affect the redox reaction on the exterior surface of microbial cell. Organic complexes of copper are relatively nontoxic to microorganisms [121].

[00279] Cupric copper at higher levels in free ionic form is toxic to microbial cells [122]. Copper provided by copper vermiculite is cupric, and can be released from the interlayer regions of vermiculite continually. This resulted in strong antimicrobial property of copper vermiculite. In addition, according to characteristics of copper vermiculite, the copper atoms are homogenously dispersed in vermiculite structure. Vermiculite is insoluble in water and inorganic solvents. But the metal ions in interplane regions are exchangeable. This leads to a slow release rate of copper from the structure of copper vermiculite.

[00280] The copper vermiculite has similar structural and chemical stability to naturally occurring magnesium vermiculite. Vermiculite carrier is stable under industrial and environmental conditions, and free ions of copper automatically are made available at the surface due to the diffusion of copper ions. Vermiculite can therefore provide a consistent and effective delivery vehicle for antimicrobial agents. Copper ions in the interlayer of vermiculite can be slowly released via cation exchange and delivery to the surface by diffusion. Copper vermiculite releases copper ions when common environmental cations such as sodium, magnesium, calcium and potassium become available for exchange with the copper in the vermiculite. The environmental conditions favoring release of copper ions at the surface would precisely inhibit the survival or growth of biological pathogens on the surface. Copper elutes from vermiculite only in the presence of moisture, and only until the copper concentration reaches a local equilibrium value that happens to be in the right range of concentrations needed to kill microbes. The ion delivery mechanism is so efficient that the total amount of copper needed is very small, rendering such substances extremely safe. The ion concentration at the surface can be reliably maintained within an effective killing range for many years. In very dry conditions in which microorganisms do not survive long or propagate, copper is not released. The duration of antimicrobial efficacy is thus enhanced because the active ingredient is not consumed when it is not needed. This should also greatly reduce the possibilities for development of microbial copper resistance.

Figure 51:
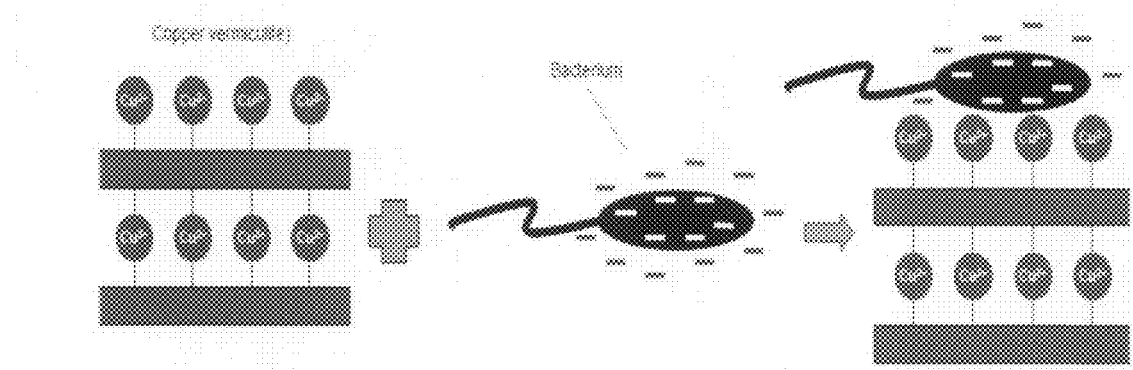

[00281] In addition, since the surfaces of particles of copper vermiculite are positively charged, and the surfaces of microbial cells are negatively charged, this will result in physical absorption once microorganisms come close to the surfaces of copper vermiculite particles (Fig. 51).

[00282] In copper vermiculite and exfoliated copper vermiculite, the concentrations of other heavy metals were significantly lower than copper (Table 11). These heavy metals could not perform significant antimicrobial efficiency. For example, the concentrations of silver and zinc in VV-CCE were 4.25ppm and 1475ppm, respectively, but VV-CCE did not show up antimicrobial activity.

Table 11. Concentration of Trace Elements with Antimicrobial Ability in Copper Vermiculite (MCV) and Exfoliated Copper Vermiculite (MECV) (ppm)

|  | V | Ni | Zn | As | Ag | Cd | Hg | Pb |
| --- | --- | --- | --- | --- | --- | --- | --- | --- |
| VV-CCE | 278.75 | 650 | 1475 | <0.37 | 4.25 | 0.55 | <2.5 | 46.63 |
| MCV | 243.75 | 487.50 | 228.75 | <0.37 | 7.63 | 7.91 | <2.5 | 49.88 |
| MECV | 227.5 | 646.25 | 167.5 | <0.37 | 5.25 | 8.18 | <2.5 | 30.63 |

3.8 Summary

[00283] The antibacterial efficiency of copper vermiculite was qualitatively evaluated by the diffusion method (both liquid diffusion method and solid diffusion method) against the most common but seriously pathogenic species: *E. coli*, *S. aureus*, and *K. pneumoniae*. The result showed that the release velocity of copper from copper vermiculite is very slow. However, copper vermiculite clearly has excellent antibacterial efficiency to *S. aureus*, *K. pneumoniae* and *E. coli*. The antibacterial ability of copper vermiculite is against *S. aureus*. Exfoliated copper vermiculite demonstrated more efficient antibacterial ability than un-exfoliated copper vermiculite, even when less sample amounts were utilized.

[00284] The antibacterial efficiency of copper vermiculite was also quantitatively evaluated by determining the reduction rate (death rate) of *E. coli*. Copper levels of 10 ppm to 200 ppm copper vermiculite (as 0.255 to 5.10 ppm in metal copper) were examined with all experiments repeated three times. In the control vermiculite suspensions, *E. coli* densities remained constant during the 12 hour contact time; in contrast, bacteria levels with copper vermiculite significantly decreased. In the experiment with 200 ppm copper vermiculite (5.10 ppm Cu), viable *E. coli* levels were reduced by 94.8% at 1 hour, 99.6% at 2 hours, and >99.9% at 4 hours. Even 10 ppm of copper vermiculite in solution can resulted in the reduction of cell population of *E. coli*, while the untreated vermiculite had no antibacterial activity. The slow release of copper revealed that the antimicrobial effect of copper vermiculite was due to the strong interactions between copper ions and bacteria cells.

[00285] Exfoliated copper vermiculite has even stronger antibacterial activity than copper vermiculite against *E. coli*. With 200 ppm exfoliated copper vermiculite in bacteria suspension (4.68 ppm of copper atoms), the reduction of viable bacteria are 99.8% at 1 hour, and >99.9% at 2 hours. With 10 ppm exfoliated copper vermiculite in bacteria dilution (0.234 ppm of copper atoms), the reduction of viable *E. coli* reached 98.7% at 1 hour, and >95.6% at 2 hours.

[00286] Antifungal activity of copper vermiculite was investigated against mold. Incubated at 36°C for 48 hours, all of the surfaces of untreated control samples, including micron-sized vermiculite, exfoliated vermiculite, bentonite, and kaolin, have been covered by thick mold films. However, there were no mold showed on copper vermiculite and exfoliated copper vermiculite. Even after the incubation was lasted for 21 days, copper vermiculite and exfoliated copper vermiculite did not show any mold on the surface. These results exhibited copper vermiculite has excellent antifungal activities against mold.

[00287] The antimicrobial mechanism of copper vermiculite was discussed. Antimicrobial activity of copper could be achieved through several different mechanisms. In general, antimicrobial mechanism of copper is considered that results from its strong ionic nature. Once the metallic ion of copper diffuses across cell membrane of pathogenic microbe by various pathways, it inhibits the enzymatic activity by substituting native metal ions within an enzyme. This substitution would render the enzyme nonfunctional and the metabolism of microbe is disrupted. Consequently, the replication of microbe is terminated. The most important is the interactions of copper with nucleic acids. Cupric copper at higher levels in free ionic form is toxic to microbial cells. Copper ions in the interlayer of vermiculite can be slowly released via cation exchange and delivery to the surface by diffusion. This resulted in strong antimicrobial property of copper vermiculite.

[00288] In copper vermiculite, the concentrations of other heavy metals were greatly lower than copper. These heavy metals could not have significantly antimicrobial efficiency.

4 Assessment of Chemical Stability of Copper Vermiculite

4.1 Goals

[00289] Stability and durability are important factors for applications and lifetime prediction of antimicrobial materials. To understand the antibacterial and antifungal activities of copper vermiculite, the leaching rates of copper metal from copper vermiculite were investigated.

4.2 Procedures of Measurement of Leaching Rate

[00290] The copper vermiculite used in this measurement included copper vermiculite (MCV) and exfoliated copper vermiculite (MECV).

[00291] The samples were previously dried at 105°C for 24 hours, and blended in a rolling chamber for 5 minutes to be uniformly mixed.

[00292] Weighed 2.0 grams mixed sample, and placed into 250 ml flask, added 100 ml distilled water, then sealed with Kimfilm. Then the flask was put into a horizontal-motioned mechanic shaker for a certain period of shaking at room temperature. The shaking periods were set for each sample were 1 hour, 24 hours, 3 days, 7 days, and 28 days, respectively.

[00293] After shaking for a desired time, the leached solutions were centrifuged at 3600 rpm for 10 minutes, and the supernatants were diluted to 100 ml, and taken to chemical analysis. For comparison, equivalent of samples were prepared by soaking procedure, which statically placed sample within distilled water for a desired period, and centrifuged to obtain soaked leaching solution.

[00294] The concentrations of metals in the solutions including copper, iron, calcium, magnesium, silicon, barium, zinc, titanium, strontium, were measured with ICP.

[00295] To compare the leaching velocity of copper ions, equal amounts of copper vermiculite samples were prepared by soaking procedure, which statically placed samples within distilled water for a desired period, and centrifuged to obtain soaked leaching solution for chemical analysis.

4.3 Leaching Rate of Copper Vermiculite

[00296] According to the chemical analytic results from leaching solutions of copper vermiculite, the major metals released were copper, magnesium, iron, silicon, and aluminum. There were few trace elements, such as barium, titanium, were also released. Under this dynamic leaching condition, all the major elements shown near linear leaching rates, and concentrations slowly increased along with the leaching time. The trace elements kept only very lower concentration in the solution. The appropriate leaching rate equations are:

$$Cu: Y = 0.0276X + 2.69 \quad (23)$$
$$Mg: Y = 0.0552X + 3.60 \quad (24)$$
$$Fe: Y = 0.0559X + 2.51 \quad (25)$$
$$Ti: Y = 0.006X + 0.33 \quad (26)$$

Where, X is the lasting time of leaching processing, Y is the metal concentration corresponding element in the solution.

Figure 52:
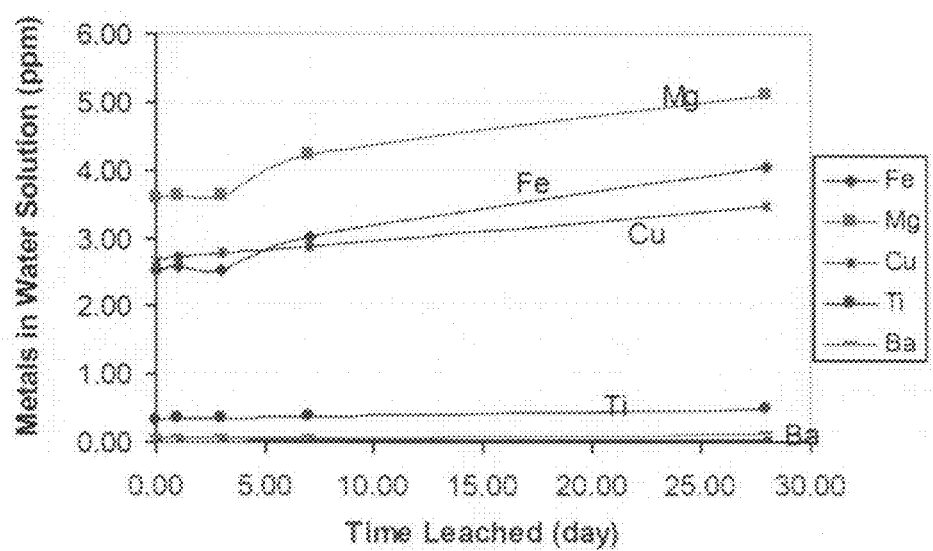

[00297] Copper concentrations in leached solutions extracted for 1 hour was 2.68 ppm, and 3.46 ppm for 28 days (Table 12, Fig. 52). According to the test results and discussions in Sections 3.4 and 3.5, such concentrations of copper are sufficient to inhibit the replication of bacteria in aqueous solution. This demonstrated that the copper vermiculite is able to release sufficient copper ions, in a period of 1 hour, to inhibit the replication of *E. coli*.

Table 12. Concentration of Major Metals in Solution Leached from Copper Vermiculite

| Sample | Leaching Time (d) | Concentration of Metals (ppm) | | | | | | | |
|---|---|---|---|---|---|---|---|---|---|
| | | Fe | Mg | Al | Cu | Ti | Ca | Sr | Ba |
| LMCV-1h | 0.04 | 2.54 | 3.59 | 4.24 | 2.68 | 0.32 | 0.09 | 0.01 | 0.06 |
| LMCV-24h | 1 | 2.58 | 3.63 | 4.41 | 2.73 | 0.34 | 0.10 | 0.01 | 0.06 |
| LMCV-3d | 3 | 2.52 | 3.63 | 2.81 | 2.80 | 0.34 | 0.09 | 0.01 | 0.07 |
| LMCV-7d | 7 | 3.02 | 4.22 | 4.81 | 2.87 | 0.37 | 0.12 | 0.02 | 0.07 |
| LMCV-28d | 28 | 4.06 | 5.11 | 5.40 | 3.46 | 0.49 | 0.10 | 0.02 | 0.10 |

[00298] For copper vermiculite, the maximum concentration of copper, 3.46 ppm, in the leached solution is the sample shaken for 28 days. That is, 1 gram of copper vermiculite could only release out 173 μg (173 ppm) of copper by the shaking leaching approach for 4 weeks (or 185μg for 1 month). Assume copper atoms can be leached averagely and constantly in this velocity, it would need at least 138 months (11.5 years) to exhaust the copper atoms in copper vermiculite (average copper content in vermiculite is 2.55wt%). In other words, the lifetime of copper vermiculite is longer than 11 years.

Figure 53:
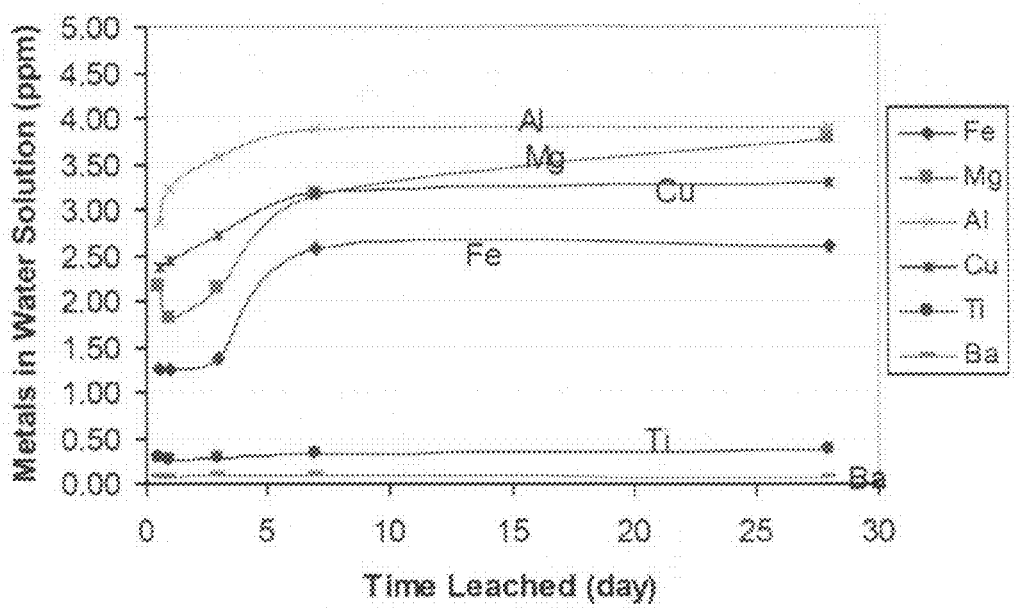

[00299] By the soaked leaching approach, the concentrations of major metals in the solution shown rapidly increase in the first week, and then kept a constant concentration (Fig. 53, Table 13). However, the release speed of the metals was much lower than that in the solutions by the leaching processing. The processing type had no impact to the concentrations of the track elements in the solutions. By 28 days, 1 gram of copper vermiculite can release out 165μg of copper (or 177μg for 1 month). In such rate, the lifetime of copper vermiculite would be longer than 144 months (or 12 years).

Table 13. Concentration of Major Metals in Soaked Solution from Copper Vermiculite

| Sample | Leaching time (d) | Concentration of Metals in Solution (ppm) | | | | | | | |
|---|---|---|---|---|---|---|---|---|---|
| | | Fe | Mg | Al | Cu | Ti | Ca | Sr | Ba |
| SMCV-12h | 0.5 | 1.26 | 2.16 | 2.86 | 2.38 | 0.28 | 0.12 | 0.02 | 0.08 |
| SMCV-24h | 1 | 1.26 | 1.81 | 3.23 | 2.43 | 0.26 | 0.11 | 0.01 | 0.07 |
| SMCV-3d | 3 | 1.38 | 2.13 | 3.58 | 2.72 | 0.27 | 0.11 | 0.01 | 0.08 |
| SMCV-7d | 7 | 2.59 | 3.17 | 3.89 | 3.18 | 0.32 | 0.13 | 0.02 | 0.10 |
| SMCV-28d | 28 | 2.61 | 3.79 | 3.91 | 3.30 | 0.37 | 0.13 | 0.01 | 0.08 |

4.4 Leaching Rate of Exfoliated Copper Vermiculite

Figure 54:
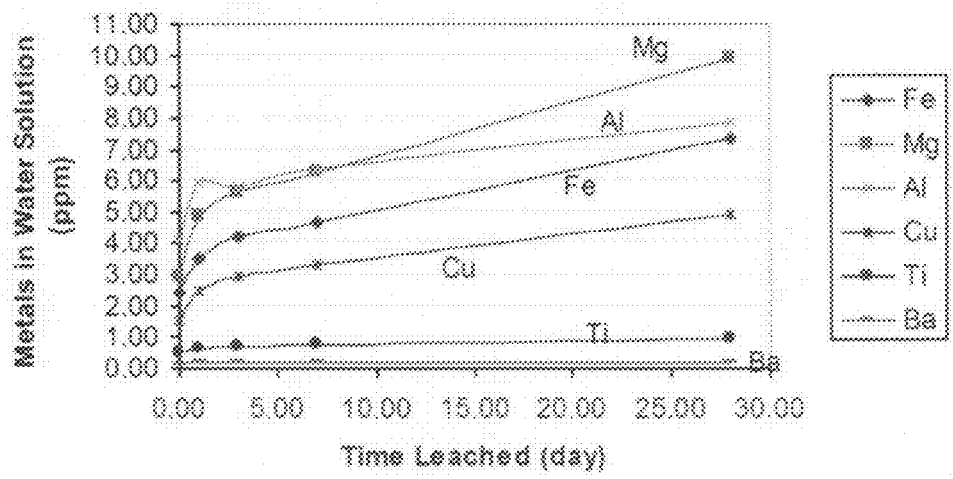

[00300] Table 14 and Fig. 54 have shown that the major metals in exfoliated copper vermiculite (MECV) have faster release velocities than the release velocity of copper vermiculite (MCV). It also shows the metal concentrations in the solutions had a large increment in the first 24 hours, and then reduced to another linear increase. The release rate of copper ions is appropriately:

$$Y = 0.1003X + 2.27 \tag{27}$$

Here, X is the time length of leaching processing; Y is copper concentration in the solution. The slope of MECV solution is greater than that of MCV. This fact demonstrates that MECV particle has both a faster release rate and a larger increase in releasing copper ions, while its concentration of copper is lower than MCV. This fact also explains why the smaller amount of MECV had better antibacterial effect comparing to MCV. This fact is consistent to the difference of structural features of copper vermiculite and exfoliated copper vermiculite. Within copper vermiculite, copper ions were mostly bonded in the interlayer sites as the substitutes of magnesium ions, resulted in copper ions were relatively stable, and slow- released; in exfoliated copper vermiculite, a higher percentage of copper ions were absorbed on the exfoliated free surface of aluminum silicate sheet, which resulted in a lower bonded energy, and relative faster release rate compared to copper ions.

[00301] For exfoliated copper vermiculite, the maximum concentration of copper, 4.94 ppm, in the leached solution was shaken for 28 days. That is, 1 gram of copper vermiculite can release 247 μg of copper by shaked leaching approach for 4 weeks (or 265μg for 1 month). Provided copper atoms can be leached constantly in this velocity, it would need at least 88 months (7.4 years) to exhaust the copper atoms in copper vermiculite (average copper content in vermiculite is 2.34 wt%). In other words, the lifetime of copper vermiculite is longer than 7.4 years.

Table 14. Concentration of Major Metals in Solution Leached from Exfoliated Copper Vermiculite

| Sample | leaching Time (d) | Concentration of Metals in Solution (ppm) | | | | | | | |
|---|---|---|---|---|---|---|---|---|---|
| | | Fe | Mg | Al | Cu | Ti | Ca | Sr | Ba |
| LMECV-1h | 0.04 | 2.43 | 2.97 | 4.09 | 1.56 | 0.51 | 0.09 | 0.03 | 0.14 |
| LMECV-24h | 1 | 3.51 | 4.89 | 5.97 | 2.48 | 0.65 | 0.10 | 0.04 | 0.17 |
| LMECV-3d | 3 | 4.24 | 5.65 | 5.83 | 2.94 | 0.68 | 0.13 | 0.04 | 0.17 |
| LMECV-7d | 7 | 4.69 | 6.29 | 6.40 | 3.33 | 0.74 | 0.14 | 0.04 | 0.17 |
| LMECV-28d | 28 | 7.37 | 9.92 | 7.85 | 4.94 | 0.98 | 0.18 | 0.04 | 0.20 |

Figure 55:
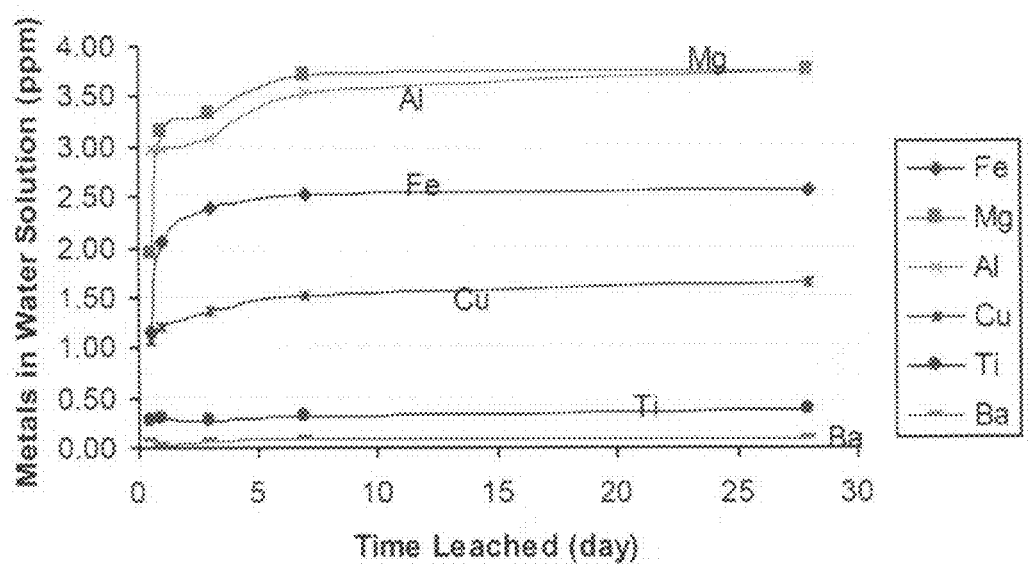

[00302] Like MCV, the release rate of MECV was also slowed down with the static soaking processing (Fig. 55, Table 15). By the soaked leaching approach, 1 gram of exfoliated copper vermiculite can release 83μg of copper after 28 days, (or 89μg for 1 month). The lifetime of copper vermiculite would be longer than 263 months (or 21.9 years).

Table 15. Concentration of Major Metals in Soaked Solution of Exfoliated Copper Vermiculite

| Sample | Leaching Time (d) | Concentration in Solution (ppm) | | | | | | | |
|---|---|---|---|---|---|---|---|---|---|
| | | Fe | Mg | Al | Cu | Ti | Ca | Sr | Ba |
| SMECV-12h | 0.5 | 1.16 | 1.95 | 2.98 | 1.07 | 0.27 | 0.08 | 0.02 | 0.07 |
| SMECV-24h | 1 | 2.05 | 3.16 | 2.96 | 1.21 | 0.28 | 0.08 | 0.00 | 0.03 |
| SMECV-3d | 3 | 2.38 | 3.33 | 3.09 | 1.35 | 0.28 | 0.10 | 0.01 | 0.06 |
| SMECV-7d | 7 | 2.52 | 3.72 | 3.52 | 1.53 | 0.30 | 0.11 | 0.01 | 0.09 |
| SMECV-28d | 28 | 2.56 | 3.75 | 3.76 | 1.66 | 0.38 | 0.13 | 0.02 | 0.10 |

Figure 56:
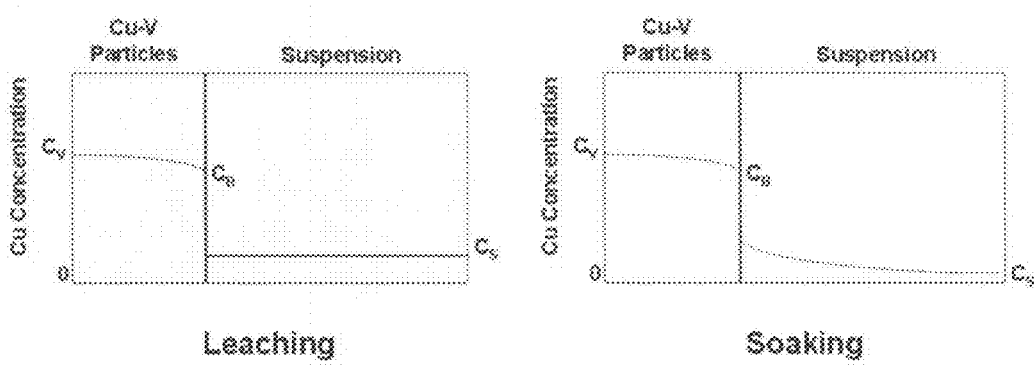

[00303] Leaching and soaking methods were based on two different principals (Fig. 56). In Fig. 56, the left side of each diagram represents a particle of copper vermiculite, while the right side is the suspension. Cv is the metal concentration at the center of vermiculite particle; $C_B$ is the metal concentration at the edge of vermiculite particles; Cs is the metal concentration in solution. During leaching process, the copper and other metal ions were extracted from the surface or near surface area of vermiculite particles into the solution. The metal concentration at the boundary of particle-solution ($C_B$) would be lower than that at the center of the particle (Cv). $C_S$ is also much lower than $C_B$ due to the structural stability of vermiculite. With motion of shaking, the metal concentration in the solution is homogenous. However, it is not even in the soaking solution, which results in concentration grads that metals have high concentration near particle, and low concentration far from the particles. Since the driving force of extracting metals from vermiculite is the difference of metal concentration between $C_B$ and Cs, soaking method has a relatively low extraction rate of metals. Once the concentration difference was minimized, the release of metals paused. From the leaching results (Fig. 52 and 54), the major metals of copper vermiculite were slowly released, and the concentrations in the solutions gradually increased along with the process time. The concentrations of trace elements in the solutions had no obvious change during entire leaching process due to the low content in vermiculite. However, soaked solution had a different curves of concentrations, which increased in the first week and kept steady values until the end of soaking process after 28 days (Fig. 53 and 55).

Figure 57:
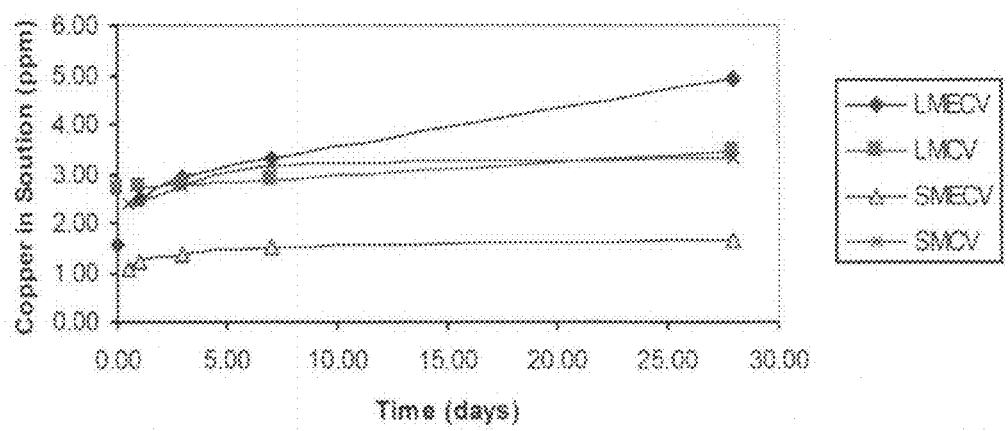

[00304] In comparison, the release rates of copper ions from vermiculite structure by the both methods are shown in Fig. 57. Clearly, leaching process provided rapider release speed of metal than soaking process. MECV took rapidest release rate of copper among these four measurements. In fact, the release speed of copper in actual application would be slower the velocities above, as the environments to mainly utilize copper vermiculite will be not in solution. The actual lifetime of copper vermiculite would much longer than that established above.

4.5 Summary

[00305] Stability and durability are important factors for applications and lifetime prediction of antimicrobial materials. Stability of copper ions in copper vermiculite was measured by aquatically leaching processes. Copper vermiculite and exfoliated copper vermiculite were put into water in a ratio of 2.0g/100ml, and then implemented leaching processes by continuously shaking (leaching) and statically storing (soaking) for desired periods of time, respectively. The chemical analytic results showed that the major metals released were copper, magnesium, iron, and aluminum. The release rate of copper depends on the environmental conditions. Under the dynamic leaching condition, all the major elements show linear leaching rates, and slowly increase along with the leaching time. Copper concentration in leached solutions at the 1st hour had exceeded the concentration needed to inhibit the replication of *E. coli* in aqueous solution. Lasting for 1 month, 1 gram of copper vermiculite only released out 185μg of copper. At this velocity, 11.5 years are required to completely exhaust the copper atoms from copper vermiculite. A soaking process provided a lower release rate than leaching process.

[00306] Comparably, exfoliated copper vermiculite has lower copper concentration, stronger antimicrobial effect, but faster release rate than copper vermiculite, due to their different structure characteristics.

[00307] The copper ions implanted in the interlayer regions of vermiculite are exchangeable. The release rate of copper from its host would vary along with the environmental conditions.

5 Expected Applications and Environment Impact of Copper Vermiculite

5.1 Potential Application of Copper Vermiculite Antimicrobial Materials

[00308] Antimicrobial copper vermiculite is expected to be applied on surfaces where humans will have contact. These materials should resist microbial corrosion, restrict growth of pathogenic biofilms and prevent the transfer of germs. Once the copper vermiculite is used, the surface of the products is expected to be biofilm-free. Since antimicrobial protection of the products containing copper vermiculite is built-in, it won't wash off or wear away, but provides continuous antimicrobial protection with self-decontamination for the life of many different types of surfaces and products. Therefore, the potential market for the material is enormous since many things involved with daily life could benefit from antibacterial properties.

[00309] Vermiculite is a clay mineral like kaolin. Since kaolin has been extensively utilized as fillers and extenders in paints, plastics, papers and many other applications, copper vermiculite should encounter low resistance as an additive to these applications. Examples for the daily life applications may include plastics for toys, cell phones, computer keyboard, toilet lids, tubs, furniture, automobile panels, bowling balls, golf balls, buoys, shoes, pens, rulers, folder binders, etc.

[00310] The expected usage of copper vermiculite antimicrobial materials is very extensive in hygienic-sensitive areas. The benefits of the products and technology are not only for human health protection but also other industrial applications (Table 16).

5.2 Environmental Impact of Copper Based Antimicrobial Materials

[00311] Copper is an essential trace element that is widely distributed in animal and plant tissues [123]. Like any other heavy metals, unbound ions of copper may have toxicity if the concentration of copper in solution exceeds a threshold value. In general, copper is considered safe to humans. A typical example is the widespread and prolonged use of copper intrauterine devices (IUD) [124-126]. Copper ions released by the IUD act as a prefertilization spermicide and as a postfertilization inhibitor of uterine implantation. Animal testing has also proven that copper fabrics have no skin-sensitizing properties. Thus, copper has very low risk of adverse skin reactions [127].

Table 16. Expected antimicrobial products for public facilities and family utilization

| Product Classification | Possible applications |
| --- | --- |
| Construction materials | Wall, ceiling, floor and basement paints, etc. Wall paper, flooring, resin tile, handrail for stairs, carpet, sealing materials, concrete, sanitary ceramics, tile, tubs, kitchen counter, door knob, plates, arms, etc. |
| Packing products | Packing papers, envelopes, tickets, boxes, case history, coating film, invoices, etc. |
| Transportation equipments and car industry | Ship hull paints, buses, trains, other vehicles, etc. Overhead strup, dashboards, steering wheel, handle and grip, seat, various levers, seat belt, etc. |
| Entertainment and sports goods | Swimming goods, bowling balls, golf balls, footballs, buoys, fitness equipment, wear and tools for various sports and martial art, caps, gloves, shoes, etc. |
| Daily necessities for kitchen and bath rooms | Chopping board, comer trash bag, cupboard, etc. Wash basin, stool, bathtub, interior bar, etc. Toilet seat, commodes, shower switches, curtains, etc. Wash stand, bowl, tooth brush, cup, cosmetics container, etc. |
| Furniture | Tables, desks, sofa, chairs, beds, etc |
| Daily necessities for office | Computer keyboards, telephones, microphones, cameras, devices, smell avoidance, touch panel for copier, ATM, DVD case, antimicrobial work surfaces |
| Home electrical appliances | Refrigerator, washing machine, microwave oven, vacuum cleaner, air conditioner filters, humidifier, air cleaner, dish water, coffee-makers, telephone, etc. |
| Toys | Toy blocks, dolls, stuffed animals, puzzles, etc. |
| Medical products | Casing touch panel of medical instrument, gypsum, arm, etc. |
| Textile and relative products | Clothes, socks, towels, gloves, cap and hat, wig, curtain, mattress, carpets, sheets, etc. |
| Leather products | Chair seat, shoes, etc |
| Stationery | Pens, rulers, folder binders, eraser, desk mat, CD/DVD boxes, etc. |

[00312] Concerning the applications of copper vermiculite from the view of environmental protection, some factors should be considered: (1) The toxicity of copper depends on the concentration of unbound ions. In copper vermiculite, the copper is ionic but the ions are loosely bonded by the mineral structure, rather than those unbound to flow in various solutions. This is significantly different from those antimicrobial materials containing copper that have been previously reported. (2) The transfer of copper atoms depends on the diffusion conditions and cation exchange activity. (3) Copper vermiculite is a solid material, and it will be utilized as solid filler material in most cases. (4) Natural magnesium vermiculite has long term stability in a geological time sense, and this is expected to be the case for making copper vermiculite. This can be circumstantial evidence for chemical stability of copper vermiculite as well. (5) The amount of copper within plastics and paints depend on the quantity of copper vermiculite added. This is easily controllable and adjustable to various products and processes. (6) Both copper compounds and vermiculite have been used as fertilizer, pesticide and others in agriculture field for decades. For example, $CuSO_4$ is commonly utilized in dairy hoof baths. Total copper concentrations in the baths ranged from 0.8 to 1.5% Cu (2.5% Cu is recommended) [128]. (7) Many countries have regulated the critical concentration of copper in drinking water or other solution products. For example, the U.S. Environmental Protection Agency (EPA) set the MCLG of copper level in drinking water at 1.3 ppm [129]. However, there is no regulation on the concentration of copper in solids for environmental protection purpose, since copper is not a hazardous atom. (8) The expected applications in this research is mainly focused on hygienic applications, which have a potentially immense market.

[00313] Recently, the U.S. Environmental Protection Agency (EPA) has approved the registration of copper as an antimicrobial agent able to reduce specific harmful bacteria linked to potentially deadly microbial infections. Copper is the first solid surface material to receive this type of EPA registration [130].

6 Conclusions

[00314] Copper vermiculite is a new type of synthetic antimicrobial agent having functional potential as an additive in products such as plastics, paints, leathers, and woods to reduce microbial persistence and biofilm formation. In this study, two types of copper vermiculite materials, micron-sized copper vermiculite and exfoliated copper vermiculite were synthesized by a cation exchange process at 80°C, using jet-milled and exfoliated Virginia vermiculite. The characteristics, antimicrobial effects, and chemical stability of copper vermiculite were investigated. The resulting atomic content of copper (as $Cu^{2+}$) was 2.55 wt% and 2.34 wt% in copper vermiculite, and exfoliated copper vermiculite, respectively. Copper vermiculite inherited the structure of magnesium vermiculite without particles of metal copper. Copper atoms were homogeneously dispersed in the vermiculite structure.

[00315] The antibacterial efficiency of copper vermiculite was qualitatively evaluated by the diffusion methods (both liquid and solid diffusion) against the most common pathogenic species: *Escherichia coli*, *Staphylococcus aureus*, and *Klebsiella pneumoniae*. The result showed that the release velocity of copper from copper vermiculite is very slow. However, copper vermiculite clearly has excellent antibacterial efficiency to *S. aureus*, *K. pneumoniae* and *E. coli*. Exfoliated copper vermiculite demonstrated more efficient antibacterial ability than un-exfoliated copper vermiculite, even when smaller sample amounts were utilized.

[00316] The antibacterial efficiency of copper vermiculite was also quantitatively evaluated by determining its impact on the reduction rate (death rate) of *E. coli*. In the experiment with 200 ppm copper vermiculite (5.10 ppm Cu), viable *E. coli* levels were reduced by 94.8% at 1 hour, 99.6% at 2 hours, and >99.9% at 4 hours. Even 10 ppm of copper vermiculite had demonstrated sufficient inhibition against *E. coli*, while the untreated vermiculite had no antibacterial activity.

[00317] Exfoliated copper vermiculite has even stronger antibacterial activity than copper vermiculite against *E. coli*. With 200 ppm exfoliated copper vermiculite in bacteria suspension (4.68 ppm Cu), the reduction of viable bacteria are 99.8% at 1 hour, and >99.9% at 2 hours. With 10 ppm exfoliated copper vermiculite in bacteria dilution (0.234 ppm of copper atoms), the reduction of viable *E. coli* reached 98.7% at 1 hour, and >95.6% at 2 hours.

[00318] Antifungal activity of copper vermiculite was investigated against naturally developed mold. Incubated at 36°C for 48 hours, all of the surfaces of untreated control samples have been covered by thick mold layers. However, there were no mold showed on copper vermiculite and exfoliated copper vermiculite. Even after the incubation was lasted for 21 days, copper vermiculite and exfoliated copper vermiculite did not show any mold on the surface. These results exhibited copper vermiculite has excellent antifungal activities against mold.

[00319] Stability of copper ions in copper vermiculite was measured by continuously shaking (leaching) and statically storing (soaking) for desired periods of time. According to chemical analysis, the major metals released were copper, magnesium, iron, and aluminum. Under the dynamic leaching condition, all the major elements had shown linear leaching rates, and slowly increases along with the leaching time. The 1 hour leached solution had sufficient concentration to inhibit *E. coli* in aqueous solution. Lasting for 1 month, 1 gram of copper vermiculite only released out 185μg of copper. A soaking process provided a lower release rate than leaching process.

[00320] Comparably, exfoliated copper vermiculite had lower copper concentration, stronger antimicrobial effect, but a faster release rate than copper vermiculite, due to their different structure characteristics.

[00321] The suggestions for further work are to quantitatively test the antifungal activities of copper vermiculite and exfoliated copper vermiculite, and to investigate the difference of surface chemistry of copper vermiculite and exfoliated copper vermiculite.

References

[1] J. W. DenBoer, Ed. P. Yzerman and J. Schellekens, et al. A Large Outbreak of Legionnaires' Disease at a Flower Show, the Netherlands, 1999. *Emerging Infectious Diseases*, 2002, 8(1): 37-43

[2] U.S. Centers for Disease Control and Prevention (CDC). *Escherichia coli* O157:H7. http://www.cdc.gov/ncidod/dbmd/diseaseinfo/escherichiacoli_g.htm, as showed by Nov.20, 2006

[3] James M. Hughes. Emerging Infectious Diseases: A CDC Perspective. *Emerging Infectious Diseases*, 2001, 7(3): 494-496

[4] Global Health Council. Infectious diseases. http://www.globalhealth.org/view_top.php3?id=228. As showed by Nov.20, 2006

[5] World Health Organization, State of the art of new vaccines Research & Development. Geneva: WHO, 2003

[6] U.S. Centers for Disease Control and Prevention webpage. http://www.cdc.gov/ncidod/dbmd/diseaseinfo/foodborneinfections_g.htm, as showed by Nov. 20, 2006

[7] S. Hooper. Dishing the dirt on office germs. http://edition.cnn.com/2004/WORLD/europe/02/09/globaloffice.germs/, as showed by Nov.20, 2006

[8] David Williams. Is your desk making you sick? November 13, 2006 http://www.cnn.com/2004/HEALTH/12/13/cold.flu.desk/, as showed by Nov.20, 2006

[9] BBC News. March 12, 2004. Lifting the lid on computer filth. http://news.bbc.co.uk/1/hi/health/3505414.stm, as showed by Nov.20, 2006

[10] Arthur H. Rotstein. Bacteria, viruses lurk in washing machine. http://www.laundry-alternative.com/lurking.htm, as showed by Nov.20, 2006

[11] ABC News Nov. 11, 2006, Germs, bacteria lurk in your car. http://www.abcnews.go.com/Health/OnCall/story?id=2644212&page=1, as showed by Nov. 20, 2006.

[12] ABC News, Feb. 15, 2006. Germs are lurking in your office. http://www.abcnews.go.com/GMA/OnCall/story?id=1617306, as showed by Nov. 20, 2006.

[13] ABC News, Oct. 3, 2006. Schools Can Be a Hotbed of Bacteria, http://www.abcnews.go.com/GMA/OnCall/story?id=2455073&page=1, as showed by Nov.20, 2006

[14] ABC News, Aug. 4, 2006. What's dirtier, cell phone or toilet seat. http://www.abcnews.go.com/GMA/Health/story?id=2273311, as showed by Nov.20, 2006

[15] ABC News, March 30, 2006. Your Hospital Stay Could Kill You. http://www.abcnews.go.com/GMA/OnCall/story?id=1785701&page=1, as showed by Nov.20, 2006

[16] C. Feied. Novel antimicrobial surface coating and the potential for reduced fomite transmission of SARS and other pathogens. 2004

[17] J. Kaneda, S. Sawada and M. Kudo. Antibacterial metal phosphonates with aromatic ring and antibacterial resin compositions. Japan Kokai Tokkyo Koho, JP2006008588, Jan. 2006

[18] K. Miyashita, S. Himeno. Antibacterial, fungicidal compositions containing heteropoly acid salts and their use in coatings. Japan Kokai Tokkyo Koho, JP2005281299, Jan. 2005

[19] N. Inoue. Polymers with good safety and retention of antibacterial properties, and products using them. Japan Kokai Tokkyo Koho, JP 2005053973, March 3, 2005

[20] X. Wang, Q. Yu and H. Sun, et al. Method for preparing antibacterial polyester. Faming Zhuanli Shenqing Gongkai Shuomingshu, CN1425704A, June 25, 2003

[21] Y. Kimura, M. Nogami. Antibacterial coating materials containing hybrid compounds containing metal oxide polymers and polyphenols. Japan Kokai Tokkyo Koho, JP2003026921, Jan. 29, 2003

[22] R. R. Rudalal, I. J. Patel and A. G. Mehta. Studies on some metal complexes of thiosemicarbazone. *Journal of the Institution of Chemists* (India), 2001, 73(1): 13-15

[23] Y. Watanabe. Antibacterial cellular resin particles for food packagings and containers. Japan Kokai Tokkyo Koho, JP11335481, Dec. 7, 1999

[24] M. Yamazaki, K. Harada and M. Yoshida. Manufacture of antibacterial sewer pipe. Japan Kokai Tokkyo Koho, JP11172747, June 29, 1999

[25] H. Naka, M. Kobayashi and S. Kawasaki. Washfast antibacterial anionic-dyeable acrylonitrile polymer fibers and their manufacture. Japan Kokai Tokkyo Koho, JP08027621, Jan. 30, 1996

[26] T. Saeki. Antibacterial films and antibacterial gloves. Japan Kokai Tokkyo Koho, JP07138384, May 30, 1995

[27] Microban International, Ltd, Antibacterial paint, http://www.microban.com/europe/manufacturers/technology, as showed by Nov.20, 2006

[28] S.P. Yazdankhah, A.A. Scheie, E.A. Hoiby, et al. Triclosan and antimicrobial resistance in bacteria: an overview. Microbial Drug Resistance, 2006, 12 (2):83-90.

[29] H.D. Kusumaningrum, M.M. van Putten and F. M. Rombouts, et al. Effects of Antibacterial Dishwashing Liquid on Foodborne Pathogens and Competitive Microorganisms in Kitchen Sponges. *Journal of Food Protection*, 2002, 65(1): 61-65

[30] X. Wang, X. Qiao and J. Chen, et al. Advancement in research on inorganic antibacterial materials. *Journal of Ceramics*, 2003, 24(4): 239-244

[31] N. Wang, B. Li, H. Li, et al. Application of non-metallic minerals in antibacterial materials. *Journal of China Universities*, 2000, 6(2): 306-309

[32] M.T.E. Suller and A.D. Russell. Triclosan and antibiotic resistance in *Staphylococcus aureus*. Journal of Antimicrobial Chemotherapy, 2000, 46: 11-18

[33] S. Silver and L.T. Phung. A bacterial view of the periodic table: genes and proteins for toxic inorganic ions. *Journal of Industrial Microbiology and Biotechnology*, 2005, 32 (11-12): 587-605

[34] R. M. Maaier, L. L. Pepper and C. P. Gerba. Environmental microbiology. Academic Press, San Diego, CA, 2000, p551-552

[35] F. Hu, B. Li and Z. Zheng, et al. Application and prospect of metal ion antibacterial agents. *Kuangchan Zonghe Liyong*, 2000, (4): 28-33

[36] U. Hipler, P. Elsner and J. W. Fluhr. Antifungal and antibacterial properties of a silver-loaded cellulosic fiber. *Journal of Biomedical Materials Research Part B: Applied Biomaterials*, 77B(1): 156-163

[37] SINTOV-CERAX, Ltd. Silver based inorganic antibacterial agent. http://vcerax.sinto.co.jp/English/products/koukin/koukin.htm, as showed by Nov.20, 2006

[38] Samsung Group. Silver Nano Health System. http://www.samsung.com/Products/Refrigerators/SidebySide/RS2630AWWXAA.asp, as showed by Nov.20, 2006

[39] Argentum Medical, LLC. SilverIon. http://www.silverlon.com/consumer_otc_products.html, as showed by Nov.20, 2006

[40] S. H. Jeong, Y. H. Hwang and S. C. Yi. Antibacterial properties of padded PP/PE nonwovens incorporating nano-sized silver colloids. *Journal of Materials Science*, 2005, 40(20): 5413-5418

[41] International Association of Nanotechnology, Inc. FinePolymer, Inc. Technical information of nanosilver powder. http://www.nano-silver.net/eng/data_view.php?page=1&idx_no=19, as showed by Nov.20, 2006

[42] AgION Technologies. AgION Antimicrobial Effective Against H5N1 Avian Flu Virus. http://www.agion-tech.co.uk/common/NewsDetail.asp?PressID=116, as showed by Nov.20, 2006

[43] M. Teruo, N. Kazuhiko and O. Toichi. Antibacterial zeolites. japan Kokai Tokkyo Koho, JP11246212, Sept.14, 1999

[44] F. Heidenau, W. Mittelmeier and R. Detsch, et al. A novel antibacterial titania coating: Metal ion toxicity and in vitro surface colonization. *Journal of Materials Science: Materials in Medicine*, 2005, 16(10): 883-888

[45] H. Fujitsuka. Manufacture of zeolite-based sintered porous ceramics for far-IR heaters, cookwares, adsorbents, and soil substitutes. Japan Kokai Tokkyo Koho, JP2003048788, Feb. 21, 2003

[46] http://www.zeomic.co.jp/english/10_otoi.html, as showed by Nov.25, 2006

[47] http://www.wipak.com/company/winpak_group.html, as showed by Nov.25, 2006

[48] http://www.toto.co.jp/index.htm, as showed by Nov.25, 2006

[49] http://www.nano-silver.net, as showed by Nov.25, 2006

[40] http://www.jrnanotech.com/antimicrobial.html, as showed by Nov.25, 2006

[51] http://www.cibasc.com/index/ind-index.htm, as showed by Nov.25, 2006

[52] http://www.troycorp.com/functions.asp, as showed by Nov.25, 2006

[53] T. J. Berger, J. A. Spadaro and R. Bierman, et al. Antifungal properties of electrically generated metallic ions. *Antimicrobial agents and chemotherapy*, 1976, 10(5): 856-860

[54] Q. Xiao, B. Li and N. Wang. Silver-carried inorganic antibacterial agents: a review. *China Non-metallic Mining Industry Herald*, 1999, (6): 5-7

[55] P. L. Taylor, A. L. Ussher and R. E. Burnell. Impact of heat on nanocrystalline silver dressings. Part I: Chemical and biological properties. *Biomaterials*, 2005, 26(35):7221-7229

[56] P. L. Taylor, O. Omotoso and J. B. Wiskel, et al. Impact of heat on nanocrystalline silver dressings. Part II: Physical properties. *Biomaterials*, 2005, 26(35): 7230-40

[57] P. J. Kuhn. Doorknobs: a source of nosocomial infection? *Diagn. Med.*, 1983, Nov/Dec Issue

[58] H. T. Michels. Copper alloys may be allies in fight against germs. http://www.copper.org/health/papers/alloys_against_germs/alloys_against_germs.html, as showed by Nov.21, 2006

[59] M.J. Domek, M.W. Le Chevallier and S.C. Cameron, et al. Evidence of the role of copper in the injury process of coliform bacteria in drinking water. *Applied and Environmental Microbiology*, 1984, 48(2): 289-293

[60] S. J. Brookes, R. C. Shore and C. Robinson, et al. Copper ions inhibit the demineralization of human enamel. *Archives of Oral Biology*, 2003, 48(1): 25-30

[61] McDonald, F. William and S. Wright, et al. Antimicrobial polymer, United States Patent 6,797,743, Sept.28, 2004

[62] H. Watanabe and K. Nakazawa. Copper-containing antimicrobial polyamide moldings with good mechanical strength. Japan Kokai Tokkyo Koho, JP10292107, Nov. 4, 1998

[63] M. Sondossi, V. F. Riha and H. W. Rossmoore. The potentiation of industrial biocide activity with copper. I. Synergistic effect of copper with formaldehyde. *International Biodeterioration*, 1990, 26(1): 51-61

[64] Y. Kurihara, J. Takahashi and Y. Kamiike. Antibacterial agent for concrete, concrete compositions and concrete products. US Patent 6,752,867 June 22, 2004

[65] J. Gabbay. Article of clothing having antibacterial, antifungal, and antiyeast properties, United States Patent 6,124,221, Sept.26, 2000

[66] S. Sakuma, K. Atsumi. Dentifrice containing antibacterial material. United States Patent 5,468,489, Nov.21, 1995

[67] A. Burgard. Antimicrobially active acesulfame complexes, process for their preparation and their use. United States Patent 6,759,544, July 6, 2004

[68] W. J. Yoon. Manufacture of antibacterial agent by growing crystals with calcium oxide and zeolite and adding copper ions. Republic of Korean Kongkae Taeho Kongbo, KR2000006675A

[69] J.O. Noyce, H. Michels, C.W. Keevil. Potential use of copper surfaces to reduce survival of epidemic meticillin-resistant *Staphylococcus aureus* in the healthcare Environment. *Journal of Hospital Infection*, (2006) 63: 289-297

[70] S.A. Wilks, H. Michels, C.W. Keevil. The survival of *Escherichia coli* O157 on a range of metal surfaces. *International Journal of Food Microbiology*, 2005, 105: 445– 454

[71] S. A. Wilks, H. T. Michels and C. W. Keevil. Survival of *Listeria monocytogenes* Scott A on metal surfaces: Implications for cross-contamination. *International Journal of Food Microbiology*, 2006, 111: 93–98

[72] H. T. Michels, S. A. Wilks and C. W. Keevil. Effects of Copper Alloy Surfaces on the Viability of Bacterium, *E. coli* O157:H7. Hygienic Coatings & Surfaces Conference Papers, Jan. 26-28, 2004, available on http://www.copper.org/health/papers/e_coli/e_coli.html, as showed by Nov.20, 2006

[73] G. Faundez, M. Troncoso and P. Navarrete, et al. Antimicrobial activity of copper surfaces against suspensions of Salmonella enterica and Campylobacter jejuni. *BMC microbiology* [electronic edition], 2004, 4:19

[74] H. T. Michels. Anti-microbial characteristics of Copper, *Standardization News*, 2006, 34(10): 3-6

[75] A. Esteban-Cbillo, C. Pecharroman and E. Aguilar, et al. Antibacterial activity of copper monodispersed nanoparticles into sepiolite. J. Mater Sci, 2006, 41:5208-5212

[76] J. R. Morones, J. L. Elechiguerra and A. Camacho, et al. The bactericidal effect of silver nanoparticles. Nanotechnology, 2005, 16: 2346–2353

[77] D. H. Nies. Microbial heavy-metal resistance. Applied Microbiology and Biotechnology, 1999, 51:730-750

[78] C. Borghouts, A. Werner and T. Elthon, et al. Copper-Modulated Gene Expression and Senescence in the Filamentous Fungus *Podospora anserine*. Molecular and Cellular Biology, 2001, 21(2): 390-399

[79] W. Lo, M. F.Wong, H. Chua, P. H. F.Yu andC. K.Leung. Removal and Recovery of Copper (II) Ions by Bacterial Biosorption. *Applied Biochemistry and Biotechnology*, 2001, 92(1-3): 447-457

[80] M. C. Romero, E. H. Reinoso and M. I. Urrutia, et al. Biosorption of heavy metals by *Talaromyces helicus*: a trained fungus for copper and biphenyl detoxification. Electronic Journal of Biotechnology, 2006, 9(3), Special Issue.

[81] M. N. V. Prasad, K. Drej and A. Skawińska, et al. Toxicity of Cadmium and Copper in Chlamydomonas reinhardtii Wild-Type (WT 2137) and Cell Wall Deficient Mutant Strain (CW 15). *Bulletin of Environmental Contamination and Toxicology*, 1998, 60(2):306-311

[82] W. M. Antunes, A. S. Luna, C. A. Henriques and A. C. A. da Costa. An evaluation of copper biosorption by a brown seaweed under optimized conditions. Electronic Journal of Biotechnology, 2003, 6(3):

[83] H. T. Michels, S. A. Wilks, J. O. Noyce, et al. Copper alloys for human infectious disease control. Material Science & Technology Conference, Pittsburgh, PA, USA, Sept. 25-28, 2005.

[84] B. Li, S. Yu, J.Y. Hwang, et al. Antibacterial vermiculite nano-material. *Journal of Minerals & Materials Characterization & Engineering*, 2002, 1(1): 61-68

[85] Z. Pan, Applied mineralogy. Wuhan: Wuhan Technology University Press, 1993: 206

[86] W. D. Nesse. Introduction to mineralogy. New York: Oxford University Press, Inc. 2000: 253

[87] J. J. Deborah, R. Jacques and O. Pascual, et al. Local environment of intercalated lanthanide ions in vermiculite. *J. Chem. Soc., Faraday Trans.*, 1991, 87: 3077-3081

[88] J. E. Kogel, et al. Industrial Minerals and Rocks (7th ed.). Society for Mining, Metallurgy, and Exploration Inc., Littleton, CO, 2006, p.1015-1026.

[89] E. Busenberg, and C. V.Clemency. 1973, Determination of the cation exchange capacity of clays and soils using an ammonia electrode: Clays and Clay Minerals, 21, no. 4, p. 213-217.

[90] D. Borden and R. F. Giese. Baseline studies of the clay minerals society source clays: cation exchange capacity measurements by the ammonia-electrode method. Clays and clay minerals, 2001, 49(5): 444-445.

[91] Z. Pan, Applied mineralogy. Wuhan: Wuhan Technology University Press, 1993: 206

[92] D. Rigji, H. Dinel and H.R. Schulten, et al. Characterization of clay–organic-matter complexes resistant to oxidation by peroxide. European Journal of Soil Science, 1995, 46: 463

[93] R. M. Maier, I. L. Pepper, and C. P. Gerba, Environmental Microbiology. San Diego, CA: Academic Press, 2000: 447-451, 43-52.

[94] E. W. Nester, D. G. Anderson, C. E. Roberts, et al. Microbiology (4th), New York: McGraw-Hill, 2004: 612-616, 86-93

[95] The *Escherichia coli* O157:H7 Risk Assessment Team. Risk Assessment of the Public Health Impact of Escherichia coli O157:H7 in Ground Beef. U.S. Department of Agriculture Food Safety and Inspection Service, Sept.. 2001, p165

[96] T. D. Brock, M. T. Madigan, J. M. Martinko, et al. Biology of Microorganisms ($7^{th}$ ed.). Englewood Cliffs, NJ: Prentice Hall, 1994: 524-530, 561-562

[97] T. D. Brock, M. T. Madigan, J. M. Martinko, et al. Biology of Microorganisms ($7^{th}$ ed.). Englewood Cliffs, NJ: Prentice Hall, 1994: 789-807

[98] E. W. Nester, D. G. Anderson, C. E. Roberts, et al. Microbiology (4th), New York: McGraw-Hill, 2004: 576-581.

[99] AATCC Test Method 147-2004 Antibacterial Activity Assessment of Textile Materials: Parallel Streak Method

[100] AATCC Test Method 30-2004 Antifungal Activity, Assessment on Textile Materials: Mildew and Rot Resistance of Textile Materials.

[101] AATCC Test Method 100-2004 Antibacterial Finishes on Textile Materials: Assessment of.

[102] ASTM G21-96 (2002) Standard Practice for Determining Resistance of Synthetic Polymeric Materials to Fungi.

[103] ASTM E2149-01 Standard Test Method for Determining the Antimicrobial Activity of Immobilized Antimicrobial Agents Under Dynamic Contact Conditions.

[104] JIS Z 2801:2000 Antimicrobial Products-Test for Antimicrobial Activity and Efficacy. Japanese Standards Association, 2000, Tokyo, Japan

[105] E. W. Nester, D. G. Anderson, C. E. Roberts, et al. Microbiology (4th), New York: McGraw-Hill, 2004: 518-520.

[106] Ronald M. Altas, Handbook of Microbiological Media. $2^{nd}$ Edition. Boca Raton, Florida: CRC Press, 1997, p1301.

[107] E. W. Nester, D. G. Anderson, C. E. Roberts, et al. Microbiology (4th), New York: McGraw-Hill, 2004: 96-101.

[108] Z, Pan, P. Wan, et al. Applied Mineralogy. Wuhan: Wuhan University of Technology Press, 2993: 266-271

[109] L. Curtis, A. Lieberman, M. Stark, et al. Adverse health effects of indoor moulds. Nexus, 2006, 13 (4): 19-23.

[110] S. Silver. Baterial resistances to toxic metal ions-a review. Gene, 1996, 179: 9-19.

[111] R. A. Macleod, S. C. Kuo, and R. Gelinas. Metabolic injury to bacteria. 11. Metabolic injury induced by distilled water or Cu2+ in the plating diluent. J. Bacteriol. 1967, 93, 961-969.

[112] D. H. Nies. Microbial heavy-metal resistance. Applied Microbiology and Biotechnology, 1999, 51:730-750

[113] C. Borghouts, A. Werner and T. Elthon, et al. Copper-Modulated Gene Expression and Senescence in the Filamentous Fungus *Podospora anserine*. Molecular and Cellular Biology, 2001, 21(2): 390-399

[114] W. Lo, M. F.Wong, H. Chua, P. H. F.Yu andC. K.Leung. Removal and Recovery of Copper (II) Ions by Bacterial Biosorption. *Applied Biochemistry and Biotechnology*, 2001, 92(1-3): 447-457

[115] M. C. Romero, E. H. Reinoso and M. I. Urrutia, et al. Biosorption of heavy metals by *Talaromyces helicus*: a trained fungus for copper and biphenyl detoxification. Electronic Journal of Biotechnology, 2006, 9(3), Special Issue

[116] M. N. V. Prasad, K. Drej and A. Skawińska, et al. Toxicity of Cadmium and Copper in *Chlamydomonas reinhardtii* Wild-Type (WT 2137) and Cell Wall Deficient Mutant Strain (CW 15). Bulletin of Environmental Contamination and Toxicology, 1998, 60(2):306-311

[117] W. M. Antunes, A. S. Luna, C. A. Henriques and A. C. A. da Costa. An evaluation of copper biosorption by a brown seaweed under optimized conditions. Electronic Journal of Biotechnology, 2003, 6(3):

[118] B. Lippert. From cisplatin to artificial nucleases. The role of metal ion-nucleic acid interactions in biology. Biometals 1992, 5, 195-208.

[119] J. A. Simpson, K. H. Cheeseman, S. E. Smith, et al. Free-radical generation by copper ions and hydrogen peroxide. Biochcm.,J. 1988, 254, 519-523.

[120] S. Kobayashi K.Ueda,and T. Komano. The effects of metal ions on the DNA damage induced by hydrogen peroxide. Agric. Biol. Chem. 1990, 54, 69-76.

[121] I. P. Zevenhuizen, J.Dolfing. and E. J. Eshuis. and Scholten-Koerselman, I. J. Inhibitory effect of copper on bacteria related to the free ion concentration. Microb. Ecol. 1979, 5, 139-146.

[122] M. J. Domek. M. W. LeChavallier, S. C. Cameron, et al. Evidence for the role of copper in the injury process of coliform bacteria in drinking water. Appl. Environ. Microbiol. 1984, 48. 289-293.

[123] Copper Development Association Inc. http://www.copper.org/health/homepage.html. As showed by Nov.25, 2006

[124] Copper IUDs, infection and infertility. *Drug Ther. Bull.* 2002, 40: 67–69

[125].X. Bilian. Intrauterine devices. *Best. Pract. Res. Clin. Obstet. Gynaecol.* 2002, 16, 155–168

[126]. D. Hubacher, R. Lara-Ricalde, D. J. Taylor, *et al.* Use of copper intrauterine devices and the risk of tubal infertility among nulligravid women. *N. Engl. J. Med.* 2001, 345, 561–567

[127]. J. J. Hostynek, and H. J. Maibach. Copper hypersensitivity: dermatologic aspects–an overview. *Rev. Environ. Health* 2003, 18, 153–183

[128] Application of sewage biosolids to agricultural soils in the Northeast: Long-term impacts and beneficial uses. NE 1001 Annual Meeting, July 8-9, 2004, Ithaca, NY. http://cwmi.css.cornell.edu/NERA/2004minutes.htm

[129] U.S. Environmental Protection Agency official website, http://nsdi.epa.gov/safewater/dwh/t-ioc/copper.html. as showed by Nov. 25, 2006

[130] International Copper Association. http://www.copper.org/about/pressreleases/2008/pr2008_March_25.html. Accessed March 30, 2008

End of Dissertation

Conclusion, Ramifications, and Scope

[00322] The results of the research show that the synthesized antimicrobial exfoliated copper vermiculite compound of the present invention possesses stronger antimicrobial properties than its unexfoliated counterpart while having less copper content. Therefore, the exfoliated vermiculite form containing single or multi-metal elements impregnated in its interlayers provides a safer, and more economical means for self-decontamination of various materials and products. When a mixture of various metal elements having antimicrobial properties are reacted in the cation exchange mix, the resulting product can provide protection against a broader spectrum of pathogenic organisms, each metal contributing its own antimicrobial properties to the product. The antimicrobial activity of this invention can include antibacterial, antifungal, antialgal, antiviral, anti-biofilm, anti-inflammatory, bactericidal, fungicide, microbicide, germicide, bacteriostatic, fungistatic, decontamination, degerm, disinfectant, sanitize, etc.

[00323] The antimicrobial exfoliated vermiculite compound can be in any desired form or formulation. It can be applied to the articles in any of a variety of ways, and in various amounts to be added, depending upon the form of the material applied and/or the location of the condition to be treated. For example, it can be dried powders or wettable powders. It can be mixed or dispersed into various products, such as plastics, paints, wood products, papers, leather, textiles, concretes, for antimicrobial treatments. It can also be dispersed in water or other liquid for antimicrobial utilization. It can be used as emulsifiable concentrates. It can also be mixed into soil, fertilizers or other powders for antimicrobial applications. It can be mixed into soil or garden materials to use as trace element supplier. It can be spread on common surfaces, such as room corners, ventilating channels, and plants. It can be sprinkled and adhered onto surfaces of any items using an adhesive, such as a powder adhesive. In some embodiments, this exfoliated vermiculite can be contained in an article in the form of a tape, a pill, a capsule, a tablet, a lozenge or a suppository.

[00324] As will be understood by one skilled in the art, for any and all purposes, particularly in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

[00325] As will be understood by one skilled in the art, all language such as "up to", "at least", "greater than", "less than", and the like includes the number recited and refers to ranges which can be subsequently broken down into sub-ranges as discussed above. Finally, as will be understood by one skilled in the art, a range includes each individual member.

[00326] While the above description contains many specificities, these should not be construed as limitations on the scope of the invention, but rather as examples of some of the various possible combinations of antimicrobial metal elements impregnated in the product as well as the various possible process/production conditions to obtain the product.

[00327] Accordingly, the scope of the invention should be determined not by the embodiments described herein but by the appended claims and their legal equivalents.

We claim:

1. A method of making an antimicrobial exfoliated vermiculite composite material comprising:
   a) providing unexfoliated vermiculite containing at least one selection from a group consisting of a metal species selected from of copper, silver, zinc, nickel, and manganese and
   b) exfoliating the unexfoliated vermiculite in (a) by heating to high temperatures
   wherein step (a) comprises
   i) preparing unexfoliated vermiculite of desired particle size distribution,
   ii) preparing a metal solution containing at least one metal selected from the group consisting of copper, silver, zinc, nickel, and manganese, wherein the metal concentration in said metal solution is between 0.01-1.0 moles of metal per liter of water,
   iii) dissolving the product of (i) into the product of (ii) in a ratio between 1:5 and 1:100 wherein said ratio is based on grams f dry vermiculite and ml of metal solution, and
   iv) adjusting the pH value of the resulting solution in step (iii) to between 1-6.

2. The method of claim 1 wherein step (a) further comprises:
   v) heating the resulting solution (iv) to at least 40° C. and for at least 0.5 hours accompanied by continuous blending,
   vi) filtering the product of (v),
   vii) washing the product of (vi),
   viii) drying the product of (vii) producing a vermiculite cake, and
   ix) transforming of said cake in (ix) into a form for desired application.

3. The method of claim 2 wherein step (ix) comprises grinding said vermiculite cake to powder form.

4. The method of claim 1 wherein a portion of said metal species are in ionic state.

5. The method of claim 1 wherein a portion of said metal species are nanometer particles.

6. The method of claim 1 wherein said selection is in a form that is at least one selection from a group consisting of metal oxides, metal hydroxides, metal sulfides, metal sulfates, metal chlorides, metal nitrates, metal carbonates, metal phosphates, metal hydrides, and metal sulfadiazines of said metal species.

7. The method of claim 2 wherein step (v) is carried out in a reactor.

8. The method of claim 1 wherein the pH value in step (iv) is in the range of 2.5 to 4.

9. A method of making antimicrobial exfoliated vermiculite composite material comprising:
   a) providing exfoliated vermiculite of desired particle size distribution,
   b) subjecting said exfoliated vermiculite to cation exchange reaction and surface absorption comprising:
      i) preparing a metal solution containing at least one selection from a group consisting of metal species of copper, silver, zinc, nickel, and manganese,
      wherein the metal concentration in said metal solution is between 0.01-1.0 moles metal per liter of water,
      ii) dissolving the product of (a) into the product of (i) in a desired ratio in the range of 1:5 to 1:100 wherein said ratio is based on grams of dry exfoliated vermiculite and ml of metal solution,
      iii) adjusting the pH value of the solution in step (ii) to a range of 1 to 6 with acid and alkaline solutions,
      iv) heating the resulting solution in (iii) to at least 40° C. and for at least 0.5 hours and accompanied by continuous blending,
      v) filtering the product of (iv),
      vi) washing the product of (v),
      vii) drying the product of (vi) producing a vermiculite cake, and
      viii) transforming of said cake in (vii) into a form for desired application.

10. The method of claim 9 wherein step (viii) comprises grinding said vermiculite cake to powder form.

11. The method in claim 9 wherein portions of said metal species in (i) are in ionic state.

12. The method in claim 9 wherein portions of said metal species in (i) are nanometer particles.

13. The method in claim 9 wherein said metal species in (i) is in a form that is at least one selection from a group consisting of: metal oxides, metal hydroxides, metal sulfides, metal sulfates, metal chlorides, metal nitrates, metal carbonates, metal phosphates, metal hydrides, and metal sulfadiazines of said metal species.

14. The method of claim 9 wherein step (iv) is carried out in a reactor.

15. The method of claim 9 wherein the pH value in step (iv) is in the range of 2.5 to 4.

* * * * *